(12) United States Patent
Kokotos et al.

(10) Patent No.: US 9,597,318 B2
(45) Date of Patent: Mar. 21, 2017

(54) 2-OXOTHIAZOLE COMPOUNDS AND METHOD OF USING SAME FOR CHRONIC INFLAMMATORY DISORDERS

(75) Inventors: George Kokotos, Athens (GR); Berit Johansen, Trondheim (NO); Victoria Magrioti, Athens (GR); Michael Tsakos, Athens (GR)

(73) Assignee: Avexxin AS, Trondheim (NO)

( * ) Notice: Subject to any disclaimer, the term of this patent is extended or adjusted under 35 U.S.C. 154(b) by 0 days.

(21) Appl. No.: 12/897,510

(22) Filed: Oct. 4, 2010

(65) Prior Publication Data
US 2011/0136879 A1 Jun. 9, 2011

Related U.S. Application Data

(60) Provisional application No. 61/248,338, filed on Oct. 2, 2009.

(51) Int. Cl.
*A61K 31/421* (2006.01)
*A61K 31/423* (2006.01)
(Continued)

(52) U.S. Cl.
CPC .......... *A61K 31/421* (2013.01); *A61K 31/423* (2013.01); *A61K 31/426* (2013.01);
(Continued)

(58) Field of Classification Search
None
See application file for complete search history.

(56) References Cited

U.S. PATENT DOCUMENTS 3,894,152 A * 7/1975 Pons et al. .................. 514/231.5
4,855,310 A 8/1989 Murase et al.
(Continued)

FOREIGN PATENT DOCUMENTS

AU 2006326548 A1 6/2007
CH WO 2008107335 A1 * 9/2008 ........... C07C 237/20
(Continued)

OTHER PUBLICATIONS

Garfunkle et al., J. Med. Chem. (2008), 51, 4392-4403.*
Marsilje, Thomas, et al. Bioorganic and Medicinal Chemistry (2003), 11(20), 4487-4501.*
Evans JACS 129(32), pp. 10029-10041 (2007).*
P. Allevi et al., "Enzymatic Resolution of (R)- and (S)-2-(1-Hydroxyalkyl)thiazoles, Synthetic Equivalents of (R)- and (S)-2-Hydroxy Aldehydes", Journal of Organic Chemicatry, vol. 61, pp. 4144-4147 (1995).
International Search Report and written Opinion mailed Jan. 17, 2011 in corresponding PCT Application No. PCT/EP2010/064687.
B. Maryanoff et al., "Inhibitors of proteases and amide hydrolases that employ an α-ketoheterocycle as a key enabling functionality", Bioorganic & Medicinal Chemistry, vol. 16, pp. 1562-1595 (2008).
M. Seierstad et al., "Discovery and Development of Fatty Acid Amide Hydrolase (FAAH) Inhibitors", Journal of Medicinal Chemistry, vol. 51, No. 23, pp. 7327-7343 (2008).

(Continued)

*Primary Examiner* — Nyeemah A Grazier
(74) *Attorney, Agent, or Firm* — Mintz Levin Cohn Ferris Glovsky and Popeo, P.C.; Peter F. Corless

(57) ABSTRACT

The invention provides compounds of formula (I)

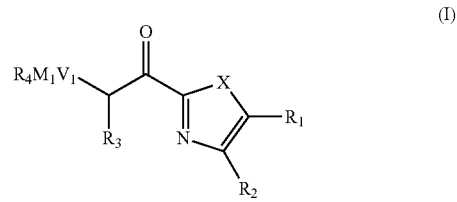

(I)

wherein X is O or S;

$R_1$ is H, OH, SH, nitro, $NH_2$, $NHC_{1-6}$alkyl, $N(C_{1-6}alkyl)_2$, halo, halo$C_{1-6}$alkyl, CN, $C_{1-6}$-alkyl, $OC_{1-6}$alkyl, $C_{1-6}$alkylCOOH, $C_{1-6}$alkylCOO$C_{1-6}$alkyl, $C_{2-6}$-alkenyl, $C_{3-10}$cycloalkyl, $C_{6-10}$aryl, $C_{1-6}$alkyl$C_{6-10}$aryl, heterocyclyl, heteroaryl, $CONH_2$, $CONHC_{1-6}$alkyl, $CON(C_{1-6}alkyl)_2$, $OCOC_{1-6}$alkyl, or is an acidic group, such as a group comprising a carboxyl, phosphate, phosphinate, sulfate, sulfonate, or tetrazolyl group;

$R_2$ is as defined for $R_1$ or $R_1$ and $R_2$ taken together can form a 6-membered aromatic ring optionally substituted by up to 4 groups $R_5$;

$R_3$ is H, halo (preferably fluoro), or $CHal_3$ (preferably $CF_3$);

each $R_5$ is defined as for $R_1$;

$V_1$ is a covalent bond, —O—, or a $C_{1-20}$alkyl group, or $C_{2-20}$-mono or multiply unsaturated alkenyl group; said alkyl or alkenyl groups being optionally interrupted by one or more heteroatoms selected from O, NH, $N(C_{1-6}$ alkyl), S, SO, or $SO_2$;

$M_1$ is absent or is a $C_{5-10}$ cyclic group or a $C_{5-15}$ aromatic group; and $R_4$ is H, halo, OH, CN, nitro, $NH_2$, $NHC_{1-6}$alkyl, $N(C_{1-6}alkyl)_2$, halo$C_{1-6}$alkyl, a $C_{1-20}$alkyl group, or $C_{2-20}$-mono or multiply unsaturated alkenyl group, said $C_{1-20}$alkyl or $C_{2-20}$alkenyl groups being optionally interrupted by one or more heteroatoms selected from O, NH, $N(C_{1-6}$ alkyl), S, SO, or $SO_2$;

with the proviso that the group $V_1M_1R_4$ as a whole provides at least 4 backbone atoms from the $C(R_3)$ group;

or a salt, ester, solvate, N-oxide, or prodrug thereof; for use in the treatment of a chronic inflammatory condition.

18 Claims, No Drawings

(51) Int. Cl.

| | | |
|---|---|---|
| *A61K 31/426* | (2006.01) | |
| *A61K 31/428* | (2006.01) | |
| *C07D 277/24* | (2006.01) | |
| *C07D 277/28* | (2006.01) | |
| *C07D 277/30* | (2006.01) | |
| *C07D 277/56* | (2006.01) | |
| *C07D 277/64* | (2006.01) | |

(52) U.S. Cl.
CPC .......... *A61K 31/428* (2013.01); *C07D 277/24* (2013.01); *C07D 277/28* (2013.01); *C07D 277/30* (2013.01); *C07D 277/56* (2013.01); *C07D 277/64* (2013.01)

(56) References Cited

U.S. PATENT DOCUMENTS

| | | | |
|---|---|---|---|
| 4,902,700 | A | 2/1990 | Hayasi et al. |
| 4,908,368 | A | 3/1990 | Murase et al. |
| 5,177,215 | A | 1/1993 | Murase et al. |
| 5,268,395 | A | 12/1993 | Simandl et al. |
| 5,272,986 | A | 12/1993 | Smart |
| 5,399,702 | A | 3/1995 | Holland et al. |
| 5,569,655 | A | 10/1996 | Dority, Jr. et al. |
| 5,569,665 | A | 10/1996 | Porter et al. |
| 5,658,909 | A * | 8/1997 | DeBernardis et al. .. 514/254.04 |
| 5,693,804 | A * | 12/1997 | DeBernardis et al. ....... 544/367 |
| 6,214,994 | B1 * | 4/2001 | DeBernardis et al. ....... 544/376 |
| 6,462,054 | B1 | 10/2002 | Boger |
| 7,056,917 | B2 | 6/2006 | Nakayama et al. |
| 2003/0055100 | A1 | 3/2003 | Uckun et al. |
| 2005/0272036 | A1 | 12/2005 | Barton et al. |
| 2006/0016218 | A1 | 1/2006 | Shapiro et al. |

FOREIGN PATENT DOCUMENTS

| | | | |
|---|---|---|---|
| DE | 2063901 | A1 | 7/1972 |
| DE | 2063901 | A1 | 7/1972 |
| DE | 2042504 | A * | 2/1975 |
| EP | 03/51194 | A2 | 1/1990 |
| EP | 03/51194 | A2 | 1/1990 |
| EP | 0577003 | A1 | 1/1994 |
| EP | 0577003 | A1 | 1/1994 |
| EP | 0735029 | A1 | 10/1996 |
| EP | 0735029 | A1 | 10/1996 |
| EP | 1201268 | A2 | 5/2002 |
| EP | 1201268 | A2 | 5/2002 |
| EP | 1748044 | A1 | 1/2007 |
| EP | 1748044 | A1 | 1/2007 |
| EP | 2116530 | A1 | 11/2009 |
| EP | 2116530 | A1 | 11/2009 |
| JP | 07036069 | A * | 2/1995 |
| JP | H11-509835 | A | 8/1999 |
| JP | H11255700 | A | 9/1999 |
| JP | 2001-240593 | A | 9/2001 |
| JP | 2002-531553 | A | 9/2002 |
| JP | 2005-128778 | A | 5/2005 |
| JP | 2006-502229 | A | 1/2006 |
| JP | 2007-533621 | A | 11/2007 |
| JP | 2009-527483 | A | 7/2009 |
| JP | 2006-502229 | A5 | 9/2010 |
| WO | 93/07140 | A1 | 4/1993 |
| WO | WO-93/07140 | A1 | 4/1993 |
| WO | 96/03392 | A1 | 2/1996 |
| WO | WO-96/03392 | A1 | 2/1996 |
| WO | 96/16052 | A2 | 5/1996 |
| WO | WO-96/16052 | A2 | 5/1996 |
| WO | WO 9615792 | A1 * | 5/1996 |
| WO | WO 9616052 | A2 * | 5/1996 |
| WO | 96-36617 | | 11/1996 |
| WO | 96/36617 | A1 | 11/1996 |
| WO | WO-96/36617 | | 11/1996 |
| WO | WO 9639399 | A1 * | 12/1996 |
| WO | WO 9832741 | A1 * | 7/1998 |
| WO | 00/09500 | A2 | 2/2000 |
| WO | 00-34254 | | 6/2000 |
| WO | 00/34254 | A1 | 6/2000 |
| WO | WO-00/34254 | | 6/2000 |
| WO | 01/00578 | A1 | 1/2001 |
| WO | 2004/016609 | A1 | 2/2004 |
| WO | 2004-033652 | | 4/2004 |
| WO | 2004/041264 | A1 | 5/2004 |
| WO | 2005-028456 | | 3/2005 |
| WO | 2006/016218 | A1 | 2/2006 |
| WO | 2006016218 | A1 | 2/2006 |
| WO | WO-2006/016218 | | 2/2006 |
| WO | 2006/057503 | A1 | 6/2006 |
| WO | 2007061862 | A2 | 5/2007 |
| WO | 2007-098142 | | 8/2007 |
| WO | 2008013963 | A2 | 1/2008 |
| WO | 2008107335 | A1 | 9/2008 |
| WO | WO-2008107335 | A1 | 9/2008 |
| WO | 2008/150492 | A1 | 12/2008 |
| WO | 2008150492 | A2 | 12/2008 |
| WO | 2011/039365 | A1 | 4/2011 |
| WO | 2012/070420 | A1 | 5/2012 |

OTHER PUBLICATIONS

English language version of Chinese communication dated Mar. 20, 2013 issued in corresponding Chinese Patent Application No. 2010800560338.

Garfunkle et al., "Optimization of the Central Heterocycle of a-Ketoheterocycle Inhibitors of Fatty Acid Amide Hydrolase", J. Med. Chem., vol. 51, pp. 4392-4403 (2008).

Walter Reid et al., 1-34, Liebigs Ann. Chem. J. Org. Chemistry, Nov. 1, 1957 (Nov. 1, 1957), pp. 2707-2711.

Angela M. Bernard et al: Palladium (0) Catalyzed Nucleophilic Substitution on 2-Cyclopropylidene-Phenoxy Ethanes, Synthetic Communications, vol. 27, No. 5, Mar. 1, 1997 (Mar. 1, 1997), pp. 709-723, XP055111880.

George A. Kraus et al: Halogen-Metal Exchange/Cyclization of Iodoketones: A Direct Synthesis of 3-Arylbenzofurans, Synlett, No. 16, Jan. 1, 2005 (Jan. 1, 2005), pp. 2504-2506.

Legrand G. Van Uitert et al: The Dissociation Constants of Beta-Diketones in Water-Diozane Solutions, The School of Chemistry and Physics, The Pennsylvania State College, Jan. 20, 1953, pp. 455-457.

Alfredo Ricci et al: Heteroacylsilanes: Synthesis and Synthetic Potentialities of New Nucleophilic Acylation Agents, The Journal of Organic Chemistry, vol. 50, No., Jan. 1, 1985, pp. 130-133.

Antonio Mete et al: Design of novel and potent cPLA2α inhibitors containing an α-methyl-2-ketothiazole as metabolically stable serine trap, Bioorganic & Medicinal chemistry Letters 21 (2011) 3128-3133.

Chemical Abstracts Service, XP002713472.
Chemical Abstracts Service, XP002713473.

Joie Garfunkle et al: Optimization of the Central Heterocycle of α-Ketoheterocycle Inhibitors of Fatty Acid Amide Hydrolase, Journal Medicinal Chemistry, 2008, vol. 51, No. 15, pp. 4391-4403.

Ahn, Kyunghye, et al., Novel Mechanistic Class of Fatty Acid Amide Hydrolase Inhibitors with Remarkable Selectivity, Biochemistry 2007, 46, 13019-13030.

Costanzo, Michael J., et al., Potent, Small-Molecule Inhibitors of Human Mast Cell Tryptase, Antiasthmatic Action of a Dipeptide-Based Transition State Analogue Containing a Benzothiazole Ketone, J Med. Chem 2003, 46, 3865-3876.

Myllymaki, Mikko J., et al., Design, Synthesis, and In Vitro Evaluation of Carbamate Derivatives of 2-Benzoxazolyl-and 2-Benzothiazolyl-(3-hydroxyphenyl)-methanones as Novel Fatty Acid Amide Hydrolase Inhibitors, J. Med. Chem. 2007, 50, 4236-4242.

Allevi, Pietro, et al., Enzymatic Resolution of (R)- and (S)-2-(1-Hydroxyalkyl)thiazoles, Synthetic Equivalents of (R)- and (S)-2-Hydroxy Aldehydes, J. Org. Chem. 1996, 61, 4144-4147.

Chikashita, Hidenori, et al., General Reactivity of 2-Lithiobenzothiazole to Various Electrophiles and the Use as a Formyl Anion Equivalent in the Synthesis of a-Hydroxy Carbonyl Compounds, Bull. Chem. Soc. Jpn., 61, 3637-3648 (1998).

(56) References Cited

OTHER PUBLICATIONS

Schmidt, U., et al., Synthesis of Optically Active 2-(1-Hydroxyalkyl)-thiazole-4-carboxylic Acids and 2-(1-Aminoalkyl)-thiazole-4-carboxylic Acids, Journal of Synthetic Organic Chemistry, 1986, No. 12, pp. 2-8.
Martin, Thibaut, et al., Highly Efficient Borylation Suzuki Coupling Process for 4-Bromo-2-ketothiazoles: Straightforward Access to Micrococcinate and Saramycetate Esters, American Chemical Society, 2001, vol. 11, No. 16, pp. 3690-3693.
Vasudevan, Anil, et al., "Heterocyclic Ketones as Inhibitors of Histone Deacetylase", Bioorganic & Medicinal Chemistry Letters 13 (2003) 3909-3913.
1-Propanone, 3-phenyl-1-(2-thiazolyl); Registry No. 1179358-89-4; Entered STN: Sep. 2, 2009.
4-Thiazoleacetic acid, 2-[2-(3-methylphenoxy)acetyl]; Registry No. 927980-02-7; Entered STN: Mar. 23, 2007.
4-Thiazoleacetic acid, 2-[2-(2-naphthalenyloxy)acetyl]; Registry No. 927980-00-5; Entered STN: Mar. 23, 2007.
4-Thiazoleacetic acid, 2-[2-(2-methylphenoxy)acetyl]; Registry No. 927979-98-4; Entered STN: Mar. 23, 2007.
4-Thiazoleacetic acid, 2-(2-phenoxyacetyl); Registry No. 927979-96-2; Entered STN: Mar. 23, 2007.
4-Thiazoleacetic acid, 2-[2-[4-(1,1-dimethylethyl)phenoxy]acetyl]; Registry No. 927979-88-2; Entered STN: Mar. 23, 2007.
4-Thiazoleacetic acid, 2-[2-(2-ethoxyphenoxy)acetyl]; Registry No. 927979-82-6; Entered STN: Mar. 23, 2007.
4-Thiazoleacetic acid, 2-[2[4-(1,1-dimethylpropyl)phenoxy]acetyl]; Registry No. 927979-42-8; Entered STN: Mar. 23, 2007.
4-Thiazoleacetic acid, 2-[2[2-(1,1-dimethylethyl)phenoxy]acetyl]; Registry No. 927979-42-8; Entered STN: Mar. 23, 2007.
4-Thiazoleacetic acid, 2-[2-(4-propylphenoxy)acetyl]; Registry No. 927979-33-7; Entered STN: Mar. 23, 2007.
4-Thiazoleacetic acid, 2-[2[2-(1-methylethyl)phenoxy]acetyl]; Registry No. 927979-27-9; Entered STN: Mar. 23, 2007.
4-Thiazoleacetic acid, 2-[2[4-(1-methylethyl)phenoxy]acetyl]; Registry No. 927979-21-3; Entered STN: Mar. 23, 2007.
4-Thiazoleacetic acid, 2-[2-(3-methoxyphenoxy)acetyl]; Registry No. 927979-15-5; Entered STN: Mar. 23, 2007.
4-Thiazoleacetic acid, 2-[2-(4-methoxyphenoxy)acetyl]; Registry No. 927979-12-2; Entered STN: Mar. 23, 2007.
4-Thiazoleacetic acid, 2-[2-(4-ethylphenoxy)acetyl]; Registry No. 927975-68-6; Entered STN: Mar. 23, 2007.
4-Thiazoleacetic acid, 2-[2-(4-methylphenoxy)acetyl]; Registry No. 927975-65-3; Entered STN: Mar. 23, 2007.
4-Thiazolecarboxylic acid, 2-[2-(3-methylphenoxy)acetyl]; Registry No. 927975-62-0; Entered STN: Mar. 23, 2007.
4-Thiazolecarboxylic acid, 2-[2-(2-naphthalenyloxy)acetyl]; Registry No. 927975-60-8; Entered STN: Mar. 23, 2007.
4-Thiazolecarboxylic acid, 2-[2-(2-methylphenoxy)acetyl]; Registry No. 927975-57-3; Entered STN: Mar. 23, 2007.
4-Thiazolecarboxylic acid, 2-(2-phenoxyacetyl); Registry No. 927975-54-0; Entered STN: Mar. 23, 2007.
4-Thiazolecarboxylic acid, 2-[2-[4-(1,1-dimethylethyl)phenoxy]acetyl]; Registry No. 927975-47-1; Entered STN: Mar. 23, 2007.
4-Thiazolecarboxylic acid, 2-[2-(2-ethoxyphenoxy)acetyl]; Registry No. 927975-41-5; Entered STN: Mar. 23, 2007.
4-Thiazolecarboxylic acid, 2-[2-[4-(1,1-dimethylpropyl)phenoxy]acetyl]; Registry No. 927975-25-5; Entered STN: Mar. 23, 2007.
4-Thiazolecarboxylic acid, 2-[2[2-(1,1-dimethylethyl)phenoxy]acetyl]; Registry No. 927975-13-1.
4-Thiazolecarboxylic acid, 2-[2-(4-propylphenoxy)acetyl]; Registry No. 927975-07-3; Entered STN: Mar. 23, 2007.
4-Thiazolecarboxylic acid, 2-[2-[2-(1-methylethyl)phenoxy]acetyl]; Registry No. 927975-03-9; Entered STN: Mar. 23, 2007.
4-Thiazolecarboxylic acid, 2-[2-[4-(1-methylethyl)phenoxy]acetyl]; Registry No. 927974-99-0; Entered Mar. 23, 2007.
4-Thiazolecarboxylic acid, 2-[2-(3-methoxyphenoxy)acetyl]; Registry No. 927974-94-5; Entered STN: Mar. 23, 2007.
4-Thiazolecarboxylic acid, 2-[2-(4-methoxyphenoxy)acetyl]; Registry No. 927974-91-2; Entered STN: Mar. 23, 2007.
4-Thiazolecarboxylic acid, 2-[2-(4-ethylphenoxy)acetyl]; Registry No. 927974-71-8; Entered STN: Mar. 23, 2007.
4-Thiazolecarboxylic acid, 2-[2-(4-methylphenoxy)acetyl]; Registry No. 927974-68-3; Entered STN: Mar. 23, 2007.
1-Propanone, 1,3-bis(2-benzothiazolyl); Registry No. 82605-58-1; Entered STN: Nov. 16, 1984.
Marsilje, T.H et al, "Design, synthesis, and biological evaluation of simplified ?-Keto heterocycle, trifluoromethyl ketone, and formyl substituted folate analogues as potential inhibitors of GAR transformylase and AICAR transformylase" Bioorganic & Medicinal Chemistry, 2003, vol. 11, No. 20, pp. 4487-4501.
Marsilje, T.H et al, "Design, synthesis, and biological evalutaion of simplified ?-Keto heterocycle, trifluoromethyl ketone, and formyl substituted folate analogues as potential inhibitors of GAR transformylase and AICAR transformylase" Bioorganic & Medicinal Chemistry, 2003, vol. 11, No. 20, pp. 4487-4501.
McGrath, M.E et al, "Structure-Guided Design of Peptide-Based Tryptase Inhibitors" Biochemistry, 2006, vol. 45, No. 19, pp. 5964-5973.
Registry, Sep. 2, 2009, RN 1179358-89-4.
Database Registry, Mar. 23, 2007, RN 927980-02-7, RN 927980-00-5, RN 927979-98-4, RN 927979-RN 96-2, 927979-88-2, RN 927979-82-6, RN 927979-60-0, RN 927979-42-8, RN 927979-33-7, RN 927979-27-9, RN 927979-21-3, RN 927979-15-5, RN 927979-12-2, RN 927979-68-6, RN 927975-65-3, RN 927975-60-8, RN 927975-57-3, RN 927975-54-0, RN 927975-47-1, RN 927975-41-5, RN 927975-25-5, RN 927975-13-1, RN 927975-07-3, RN 927975-03-9, RN 927974-99-0, RN 927974-99-0, RN 927974-99-0, RN 927974-94-5, RN 927974-91-2, RN 927974-71-8, RN 927974-68-3.
Registry, Nov. 16, 1984, RN-82605-58-1.

* cited by examiner

2-OXOTHIAZOLE COMPOUNDS AND METHOD OF USING SAME FOR CHRONIC INFLAMMATORY DISORDERS

CROSS-REFERENCE TO RELATED APPLICATION

This application claims the benefit of the following U.S. Provisional Application No. 61/248,338, filed Oct. 2, 2009, the entire contents of which are incorporated herein by reference.

BACKGROUND OF THE INVENTION

Field of the Invention

This invention relates to the use of various 2-oxothiazole or 2-oxooxazole compounds for use in the prevention or treatment of chronic inflammatory disorders such as glomerulonephritis, rheumatoid arthritis and psoriasis. The invention also relates to certain new 2-oxothiazole or 2-oxooxazole compounds, pharmaceutical compositions comprising said compounds and to new processes for the manufacture thereof.

Mammalian cells contain a large number of phospholipases that hydrolyse phospholipids in a structurally specific manner for production of a myriad of products, many of which have potent biological activity. There has been considerable interest in characterising these enzymes because of their role in production of lipid mediators of inflammation. Since the first studies 20 years ago showing that mammalian cells contain a cystolic calcium dependent phospholipase specific for arachidonic acid, an extensive amount of evidence has substantiated a primary role for $cPLA_2$ as the key enzyme that mediates the release of arachidonic acid for the production of eicosanoids.

The enzyme $cPLA_2$ contributes to the pathogenesis of a variety of diseases particularly those in which inflammation plays a primary role implicating a role for inflammatory lipid mediators in disease pathogenesis. The inhibition therefore of such lipase enzymes offers a potential therapy for inflammatory conditions in particular chronic inflammatory conditions such as those above, psoriasis and glomerulonephritis.

The phospholipases are a group of enzymes that release unsaturated fatty acids from the sn2 position of membrane phospholipids. Once released, the fatty acids are converted by various enzymes into biologically very important signalling molecules. Release of arachidonate initiates the arachidonate cascade leading to the synthesis of eicosanoids such as prostaglandins.

Eicosanoids are important in a variety of physiological processes and play a central role in inflammation. In Inflammation, Vol. 18, No. 1 1994, Andersen et al identify the presence of certain phospholipases in psoriatic human skin.

It is therefore believed that inhibition of phospholipase enzymes should have potential in curing some of the inflammatory symptoms, including epidermal hyperproliferation due to increased leukotriene production, related to eicosanoid production and cell activation in both epidermis and dermis in psoriasis.

Psoriasis is a common, chronic, inflammatory skin disorder. Psoriatic tissue is characterised by chronic inflammation in both epidermis and dermis, the disease being further characterised by hyperplasia of epidermal keratinocytes, fibroblast activation, alteration of eicosanoid metabolism, and leukocyte infiltration.

Glomerulonephritis, also known as glomerular nephritis, abbreviated GN, is a renal disease characterized by inflammation of the glomeruli, or small blood vessels in the kidneys. It may present with isolated hematuria and/or proteinuria or as a nephrotic syndrome, acute renal failure, or chronic renal failure. Glomerulonephritis is categorised into several different pathological patterns, which are broadly grouped into non-proliferative or proliferative types.

The glomerulus is a unique vascular network with three specialised types of cell: the endothelial cell, the mesangial cell and the visceral epithelial cell Mesangial cells (MC) serve a number of functions in the renal glomerular capillary including structural support of the capillary tuft, modulation of the glomerular hemodynamics and a phagocytic function allowing removal of macromolecules and immune complexes. The proliferation of MC is a prominent feature of glomerular disease including IgA nephropathy, membranoproliferative glomerulonephritis, lupus nephritis, and diabetic nephropathy.

Reduction of MC proliferation in glomerular disease models by treatment with, for example, a low protein diet has been shown to produce extracellular matrix expansion and glomerulosclerotic changes. MC proliferation inhibitors may therefore offer therapeutic opportunities for the treatment of proliferative glomerular disease.

Mesangial proliferative glomerulonephritis is a form of glomerulonephritis which involves inflammation at the kidney glomeruli. The mesangial cells which are a part of the glomerular capillaries increase in size giving the glomeruli a lumpy appearance. The disorder usually causes nephritic syndrome which represents protein loss in the urine. It may be present as acute, chronic or rapidly progressive glomerulonephritis and may progress to chronic renal failure.

The present inventors seek new treatments for, inter alia, chronic inflammatory conditions such as GN and psoriasis.

SUMMARY OF THE INVENTION

The present inventors have surprisingly found that certain 2-oxo-thiazoles or 2-oxo-oxazoles are ideal $cPLA_2$ inhibitors and offer new therapeutic routes to the treatment of chronic inflammatory disorders.

2-oxothiazole type structures are not new. In Bioorganic and Medicinal Chemistry 16 (2008) 1562-1595, there is a review of chemistry in this field. 2-oxo (benz)thiazoles carrying peptides or amino acids on the 2-position (i.e. where the 2-oxo group forms part of the backbone of an amino acid) are known in the art as thrombin inhibitors.

Also reported are certain hydrolase and transferase inhibitors in particular having a 2-oxo-oleyl side chain. Similar compounds as fatty acid amide hydrolase inhibitors are reported in J Med Chem. Vol. 51, No. 237329-7343. Their potential as inhibitors of $cPLA_2$ is not discussed.

A wider variety of 2-oxo-oxazole compounds are known from these papers. The majority of these compounds are either unsubstituted oxazole rings or they carry substituents in the position adjacent the oxygen atom. Their potential as inhibitors of $cPLA_2$ is not discussed.

Never before therefore, have the compounds claimed herein been identified as potential inhibitors of phospholipase enzymes and hence no link with chronic inflammatory conditions has been made.

Thus, viewed from one aspect the invention provides a compound of formula (I)

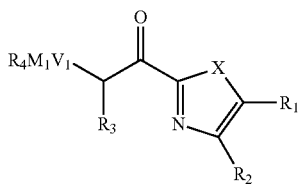

(I)

wherein X is O or S;

$R_1$ is H, OH, SH, nitro, $NH_2$, $NHC_{1-6}$alkyl, $N(C_{1-6}$alkyl$)_2$, halo, halo$C_{1-6}$alkyl, CN, $C_{1-6}$-alkyl, $OC_{1-6}$alkyl, $C_{2-6}$-alkenyl, $C_{3-10}$cycloalkyl, $C_{6-10}$aryl, $C_{1-6}$alkyl$C_{6-10}$aryl, heterocyclyl, heteroaryl, $CONH_2$, $CONHC_{1-6}$alkyl, $CON(C_{1-6}$alkyl$)_2$, $OCOC_{1-6}$alkyl, $C_{1-6}$alkylCOOH, $C_{1-6}$alkylCOO$C_{1-6}$alkyl or is an acidic group, such as a group comprising a carboxyl, phosphate, phosphinate, sulfate, sulfonate, or tetrazolyl group;

$R_2$ is as defined for $R_1$ or $R_1$ and $R_2$ taken together can form a 6-membered aromatic ring optionally substituted by up to 4 groups $R_5$;

$R_3$ is H, halo (preferably fluoro), or $CHal_3$ (preferably $CF_3$);

each $R_5$ is defined as for $R_1$;

$V_1$ is a covalent bond, —O—, or a $C_{1-20}$alkyl group, or $C_{2-20}$-mono or multiply unsaturated alkenyl group; said alkyl or alkenyl groups being optionally interrupted by one or more heteroatoms selected from O, NH, $N(C_{1-6}$ alkyl), S, SO, or $SO_2$;

$M_1$ is absent or is a $C_{5-10}$ cyclic group or a $C_{5-15}$ aromatic group (e.g. $C_{6-14}$ aromatic group); and $R_4$ is H, halo, OH, CN, nitro, $NH_2$, $NHC_{1-6}$alkyl, $N(C_{1-6}$alkyl$)_2$, halo$C_{1-6}$alkyl, a $C_{1-20}$alkyl group, or $C_{2-20}$-mono or multiply unsaturated alkenyl group, said $C_{1-20}$alkyl or $C_{2-20}$alkenyl groups being optionally interrupted by one or more heteroatoms selected from O, NH, $N(C_{1-6}$ alkyl), S, SO, or $SO_2$;

with the proviso that the group $V_1M_1R_4$ as a whole provides at least 4 backbone atoms from the $C(R_3)$ group;

or a salt, ester, solvate, N-oxide, or prodrug thereof;

for use in the treatment of a chronic inflammatory condition.

Viewed from another aspect the invention provides a compound of formula (II)

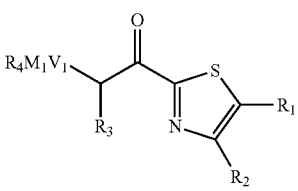

(II)

wherein $R_1$, $R_2$, $R_3$, $R_5$ and $R_4M_1V_1$ are as hereinbefore defined;

or a salt, ester, solvate, N-oxide, or prodrug thereof;

with the proviso that $R_4M_1V_1C(R_3)$ is not oleyl.

Viewed from another aspect the invention provides a compound of formula (III)

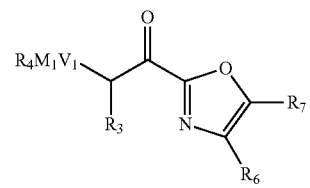

(III)

wherein $R_6$ is H, $C_{1-6}$alkyl, COOH, COO$C_{1-6}$alkyl, $CONH_2$, $CONHC_{1-6}$alkyl, $CON(C_{1-6}$alkyl$)_2$, $C_{1-6}$alkyl-COOH, $C_{1-6}$alkylCOO$C_{1-6}$alkyl;

$R_7$ is H;

wherein $R_3$ is as hereinbefore defined;

$V_1$ is a covalent bond, —O—, or a $C_{1-20}$alkyl group, or $C_{2-20}$-mono or multiply unsaturated alkenyl group;

$M_1$ is a covalent bond or is a $C_{5-10}$ cyclic group or a $C_{5-10}$ aromatic group; and $R_4$ is H, halo, OH, CN, nitro, $NH_2$, $NHC_{1-6}$alkyl, $N(C_{1-6}$alkyl$)_2$, halo$C_{1-6}$alkyl, a $C_{1-20}$alkyl group, or $C_{2-20}$-mono or multiply unsaturated alkenyl group, said alkyl or alkenyl groups being optionally interrupted by one or more heteroatoms selected from O, NH, $N(C_{1-6}$ alkyl), S, SO, or $SO_2$;

or a salt, ester, solvate, N-oxide, or prodrug thereof with the proviso that $R_4M_1V_1C(R_3)$ is not oleyl or —$(CH_2)_6$Ph.

Viewed from another aspect the invention provides a compound of formula (I')

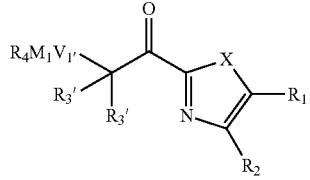

(I')

wherein X is O or S;

$R_1$ is H, OH, SH, nitro, $NH_2$, $NHC_{1-6}$alkyl, $N(C_{1-6}$alkyl$)_2$, halo, halo$C_{1-6}$alkyl, CN, $C_{1-6}$-alkyl, $OC_{1-6}$alkyl, $C_{2-6}$-alkenyl, $C_{3-10}$cycloalkyl, $C_{6-10}$aryl, $C_{1-6}$alkyl$C_{6-10}$aryl, heterocyclyl, heteroaryl, $CONH_2$, $CONHC_{1-6}$alkyl, $CON(C_{1-6}$alkyl$)_2$, $OCOC_{1-6}$alkyl, $C_{1-6}$alkylCOOH, $C_{1-6}$alkylCOO$C_{1-6}$alkyl or is an acidic group, such as a group comprising a carboxyl, phosphate, phosphinate, sulfate, sulfonate, or tetrazolyl group;

$R_2$ is as defined for $R_1$ or $R_1$ and $R_2$ taken together can form a 6-membered aromatic ring optionally substituted by up to 4 groups $R_5$;

each $R_{3'}$ is the same or different and is H, $C_{1-6}$alkyl-COO$R_a$ where $R_a$ is H or $C_{1-6}$ alkyl, halo (preferably fluoro), or $CHal_3$ (preferably $CF_3$);

each $R_5$ is defined as for $R_1$;

$V_{1'}$ is a covalent bond, —O—, —NHCO$C_{0-6}$alkyl- (i.e. where NH is adjacent the $CR_{3'}$ group), a $C_{1-20}$alkyl group, or $C_{2-20}$-mono or multiply unsaturated alkenyl group; said alkyl or alkenyl groups being optionally interrupted by one or more heteroatoms selected from O, NH, $N(C_{1-6}$ alkyl), S, SO, or $SO_2$;

$M_1$ is absent or is a $C_{5-10}$ cyclic group or a $C_{5-15}$ aromatic group (e.g. $C_{6-14}$ aromatic group); and $R_4$ is H, halo, OH, CN, nitro, $NH_2$, $NHC_{1-6}$alkyl, $N(C_{1-6}$alkyl$)_2$, halo$C_{1-6}$alkyl, a $C_{1-20}$alkyl group, or $C_{2-20}$-mono or multiply unsaturated alkenyl group, said $C_{1-20}$alkyl or $C_{2-20}$alkenyl groups being optionally interrupted by one or more heteroatoms selected from O, NH, N($C_{1-6}$ alkyl), S, SO, or $SO_2$;

with the proviso that the group $V_1'M_1R_4$ as a whole provides at least 4 backbone atoms from the $C(R_3')_2$ group; or a salt, ester, solvate, N-oxide, or prodrug thereof with the proviso that $R_4M_1V_1C(R_3')_2$ is not oleyl. It is also preferred if $R_4M_1V_1C(R_3')_2$ is not $CH_2Ph$.

The invention also concerns a compound of formula (I') as hereinbefore defined but without the disclaimer for use in the treatment of a chronic inflammatory condition.

Viewed from another aspect the invention provides a compound of formula (III')

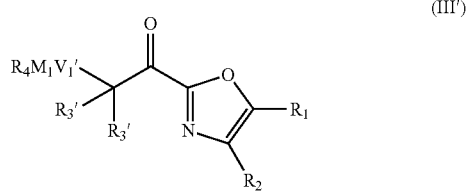

wherein $R_6$, $R_7$, $R_3'$, $V_1'$, $M_1$, $R_4$ are as hereinbefore defined;

with the proviso that $R_4M_1V_1C(R_3)$ is not oleyl or —$(CH_2)_6Ph$.

Viewed from another aspect the invention provides a pharmaceutical composition claim comprising a compound of formula (I'), (II), (III) or (III') as hereinbefore defined.

Viewed from another aspect the invention provides a compound of formula (I'), (II), (III) or (III') as hereinbefore defined for use in therapy.

Viewed from another aspect the invention provides use of the a compound of formula (I) or (I') as hereinbefore defined in the manufacture of a medicament for the treatment of a chronic inflammatory condition.

Viewed from another aspect the invention provides a method of treating a chronically inflammatory disorder comprising administering to a patient an effective amount of a compound of formula (I) or (I') as hereinbefore defined.

DEFINITIONS

In this specification, unless stated otherwise, the term "alkyl" includes both straight and branched chain alkyl radicals and may be methyl, ethyl, n-propyl, i-propyl, n-butyl, i-butyl, s-butyl, t-butyl, n-pentyl, i-pentyl, t-pentyl, neo-pentyl, n-hexyl or i-hexyl, t-hexyl.

The term "cycloalkyl" refers to an optionally substituted carbocycle containing no heteroatoms, including mono-, and multicyclic saturated carbocycles, as well as fused ring systems. Cycloalkyl includes such fused ring systems as spirofused ring systems. Examples of cycloalkyl include cyclopropyl, cyclobutyl, cyclopentyl, cyclohexyl and the like.

The term "alkenyl" includes both straight and branched chain alkenyl radicals. The term alkenyl refers to an alkenyl radicals one or more double bonds and may be, but is not limited to vinyl, allyl, propenyl, i-propenyl, butenyl, i-butenyl, crotyl, pentenyl, i-pentenyl and hexenyl.

The term "aryl" refers to an optionally substituted monocyclic or bicyclic hydrocarbon ring system containing at least one unsaturated aromatic ring. Examples and suitable values of the term "aryl" are phenyl, naphtyl, 1,2,3,4-tetrahydronaphthyl, indyl, indenyl and the like.

In this specification, unless stated otherwise, the term "heteroaryl" refers to an optionally substituted monocyclic or bicyclic unsaturated, aromatic ring system containing at least one heteroatom selected independently from N, O or S. Examples of "heteroaryl" may be, but are not limited to thiophene, thienyl, pyridyl, thiazolyl, isothiazolyl, furyl, pyrrolyl, triazolyl, imidazolyl, oxadiazolyl, oxazolyl, isoxazolyl, pyrazolyl, imidazolonyl, oxazolonyl, thiazolonyl, tetrazolyl and thiadiazolyl, benzoimidazolyl, benzooxazolyl, benzothiazolyl, tetrahydrotriazolopyridyl, tetrahydrotriazolopyrimidinyl, benzofuryl, thionaphtyl, indolyl, isoindolyl, pyridonyl, pyridazinyl, pyrazinyl, pyrimidinyl, quinolyl, phtalazinyl, naphthyridinyl, quinoxalinyl, quinazolyl, imidazopyridyl, oxazolopyridyl, thiazolopyridyl, pyridyl, imidazopyridazinyl, oxazolopyridazinyl, thiazolopyridazinyl, cynnolyl, pteridinyl, furazanyl, benzotriazolyl, pyrazolopyridinyl, purinyl and the like.

In this specification, unless stated otherwise, the term "heterocycle" refers to an optionally substituted, monocyclic or bicyclic saturated, partially saturated or unsaturated ring system containing at least one heteroatom selected independently from N, O and S, e.g. piperidinyl, morpholino, or piperazinyl.

Any cyclic group can be a cycloalkyl group, cycloalkenyl group or heterocyclic group.

Any aromatic group can be aryl or heteroaryl in nature, e.g. phenyl, naphthyl or pyridyl.

An acidic group is one comprising a carboxyl, phosphate, phosphinate, sulfate, sulfonate, or tetrazolyl group, e.g. an $C_{1-6}$alkyl linked to a carboxyl, phosphate, phosphinate, sulfate, sulfonate, or tetrazolyl group. Highly preferred acidic groups are COOH, COO$C_{1-6}$alkyl, or $C_{1-6}$alkyl substituted by COOH, COO$C_{1-6}$alkyl or $C_{6-10}$aryl group substituted by COOH, COO$C_{1-6}$alkyl.

DETAILED DESCRIPTION OF INVENTION

It is preferred if X is S and the ring system is a thiazole system.

It is preferred if $R_1$ is hydrogen.

It is preferred if $R_2$ is hydrogen or is an acidic group, e.g. a group comprising a carboxylic group or derivative thereof (i.e. a COO group). Thus, $R_2$ may be COOH, or an ester, e.g. alkyl ester thereof. The acid group may also be spaced apart from the ring by some form of linking chain such as an alkylene chain or an aromatic group. Highly preferred groups are COOH, COO$C_{1-6}$alkyl and $C_{1-6}$alkylCOOH.

It is believed that the presence of a carboxyl functional group attached to the heterocyclic ring enhances interaction of the compound with the active site of the phospholipase enzyme, in particular, the side chain of arginine 200. This arginine is believed to carry a free guanidine group so any substituent which can favourably interact with this guanidine is preferred at the $R_1$ and/or $R_2$ position.

In one embodiment $R_1$ and $R_2$ can be taken together to form a ring system such as a phenyl ring or pyridine ring. Where a pyridine ring system forms the N atom is preferably in the 4-position of the ring (S=1 position, N=3, N=4). Preferably the ring system will be a carbon ring system, e.g. forming a benzothiazole type structure. If such a ring system is formed, it may be substituted preferably by 1 or 2 groups $R_5$. Preferences for $R_5$ are the same as those for $R_2$. Preferably the $R_5$ group is positioned on the 5-position of the ring (where S is the 1-position and N is the 3-position). Ideally however such a ring system is unsubstituted.

Preferred compounds in this regard are of formula (VII)

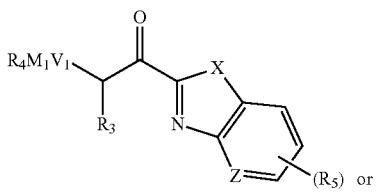

(VII)

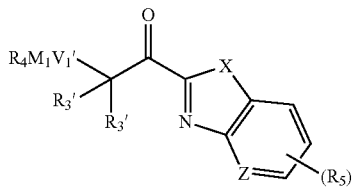

(VII')

where the substituents are as hereinbefore defined and Z is C or N.

It is especially preferred if at least one of $R_1$ and $R_2$ (especially $R_1$) is hydrogen. The heterocyclic ring is ideally only monosubstituted. In a further preferred embodiment both $R_1$ and $R_2$ are hydrogen.

$R_3$ is preferably hydrogen or, in a highly preferred embodiment, $R_3$ is halo, especially fluoro. It is believed that the presence of the F atom adjacent the carbonyl enhances the activity of the carbonyl group and may also interact favourably with the active site in the $cPLA_2$ enzyme, in particular IVa $PLA_2$.

It is preferred if one $R_{3'}$ is H. It is also preferable if one $R_{3'}$ is halo, especially fluoro. The presence of two fluoro atoms as $R_{3'}$ is also preferred. It is believed that the presence of the F atom adjacent the carbonyl enhances the activity of the carbonyl group and may also interact favourably with the active site in the $cPLA_2$ enzyme, in particular IVa $PLA_2$.

The discussion of the group $V_1M_1R_4$ which follows also applies to $V_{1'}M_1R_4$. The group $V_1M_1R_4$ as a whole provides at least 4 backbone atoms from the $C(R_3)$ group. Preferably, $V_1M_1R_4$ provides at least 5 backbone atoms, more preferably at least 7 backbone atoms especially at least 10 backbone atoms from the $C(R_3)$ group. For the avoidance of doubt, where there is an aromatic group in the backbone, the backbone is considered to follow the shortest route around the ring. Thus, for a 1,4-phenyl group, that would constitute 4 backbone atoms. A 1,3 linked 5 membered ring in the backbone would constitute 3 backbone atoms and so on.

$V_1$ (or $V_{1'}$) is preferably an $C_{1-15}$-alkyl group, $C_{2-20}$-alkenyl group or is a —$C_{1-6}$alkylO-group (i.e. where the O atom bonds to $M_1$). Any alkenyl group can have one or more than one double bond. Where more than one double bond is present, it is preferred if these are non conjugated. Double bonds will preferably take the cis form. Preferred alkyl groups for $V_1$ (or $V_{1'}$) include $C_{1-6}$-alkyl.

It is especially preferred if any alkyl or alkenyl group in $V_1$ (or $V_{1'}$) is linear.

$V_{1'}$ may also represent —O—, or an amide linkage NHCO which may then optionally carry an alkyl chain of up to 6 carbon atoms. That chain is preferably linear. The NH part of the linkage is adjacent the $CR_{3'}$ group.

Preferably $M_1$ is either absent or is an $C_{6-10}$aryl group, especially a phenyl group. Alternatively, $M_1$ may be a bicyclic aromatic group such as decalin. A further preferred embodiment is where $M_1$ represents a biphenyl group, i.e. a $C_{5-15}$ aromatic group in which two phenyl groups are directly linked. Where $M_1$ is a phenyl group, $V_1$ or $V_{1'}$ and $R_4$ are preferably attached in the 1 and 4 positions of the ring, i.e. they are para to each other.

$R_4$ is preferably an H atom, $C_{1-10}$alkyl group or an $C_{1-10}$alkoxy group.

In one embodiment it is preferred in any compound of the invention that $R_4M_1V_1C(R_3)$ or $R_4M_1V_{1'}C(R_{3'})_2$ is not oleyl or —$(CH_2)_6Ph$.

Thus, a still more preferred compound of the invention is of formula (VI)

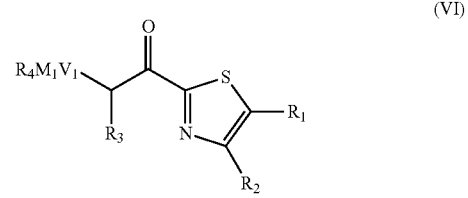

(VI)

wherein $R_1$ is H;
$R_2$ is H, COOH, $COOC_{1-6}$alkyl, $C_{1-6}$alkylCOOH, or $C_{1-6}$alkylCOOC_{1-6}alkyl;
$R_3$ is H or F;
$V_1$ is $C_{1-15}$-alkyl group, $C_{2-20}$-alkenyl group, —O—, or is a —$C_{1-6}$-alkylO-group;
$M_1$ is absent or is a phenyl group;
$R_4$ is H, $C_{1-10}$alkyl group or an $C_{1-10}$alkoxy group.

In further highly preferred combinations:
1. $V_1$ is $C_{1-15}$-alkyl group or $C_{2-20}$-alkenyl group, $M_1$ is absent and $R_4$ is H.
2. $V_1$ is $C_{1-6}$-alkyl group or is a —$C_{1-6}$alkylO group, $M_1$ is a phenyl group, and $R_4$ is H or $C_{1-6}$ alkoxy (where the O atom is adjacent the $M_1$ group);
3. $R_4V_1M_1$ represents a $C_{10-20}$ linear alkyl group.

Also preferred are options 1-3 above in which $V_1$ is $V_{1'}$.

In a highly preferred embodiment, the invention provides the compounds in the examples.

Synthesis

The manufacture of the compounds of the invention typically involves known literature reactions. For example, the formation of an 2-oxothiazole, the precursor to many of the claimed compounds, can be achieved by reaction of an aldehyde XCOH with thiazole in the presence of a base and subsequent oxidation of the hydroxyl to a ketone. The X group is obviously selected to form the desired $R_4M_1V_1$ or $R_4M_1V_{1'}$ group or a precursor thereof.

These reactions are summarised in Scheme 1 below.

Scheme 1.

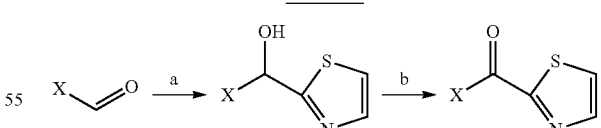

(a) thiazole, base; (b) oxidation, e.g. Dess-Martin periodinane.

It will be appreciated that in the scheme above and many of those below, specific reagents and solvents may mentioned to aid the skilled man in carrying out the reactions described. The skilled man will appreciate however that a variety of different conditions, reagents, solvents, reactions etc could be used to effect the chemistry described and the conditions quoted are not intended to be limiting on the reactions described.

An alternative strategy involves the reaction of an alkoxy amide XCON(Oalkyl) with thiazole in base which affords 2-oxothiazoles directly. This reaction is summarised in scheme 2.

Scheme 2.

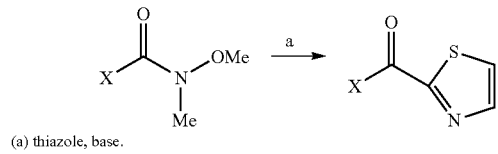

(a) thiazole, base.

The inventors have however found a new and preferred way of forming 2-oxothiazoles and this forms a still yet further aspect of the invention. The new process involves the reaction of an oxo-morpholino structure with thiazole, typically in the presence of a base. This reaction affords 2-oxo thiazoles directly and is a new reaction.

Thus viewed from another aspect the invention provides a process for the formation of a 2oxothiazole comprising reacting a compound of formula (IV) wherein Y is an organic group, e.g. a group $R_4M_1V_1CH(R_3)$,

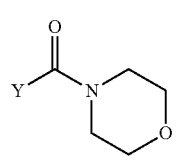

(IV)

with an optionally substituted thiazole in the presence of a base so as to form an optionally substituted compound of formula (V)

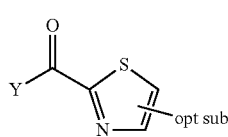

(V)

This reaction is effected in the presence of a base, e.g. nBuLi or the like. Ideally, the reaction is effected at low temperature, e.g. at 0° C. or below so in an ice bath, or other known cooling system, e.g. liquid ammonia.

It will be appreciated that this reaction is preferably used to form compounds of formula (I) or (II) or (III) or their (I')/(III') analogues and this forms a still further aspect of the invention. It will be preferred therefore if the definition if Y reflects the group $R_4M_1V_1CH(R_3)$ or $R_4M_1V_1C(R_3)_2$ or forms a precursor thereto. It will also be preferred if the thiazole used reflects the preferred thiazole reactant required to make a compound of the invention, i.e. carrying the necessary $R_1/R_2$ substituents etc. The reaction is however more generally applicable so variable Y is broadly defined and the thiazole may be optionally substituted.

It is believed that the morpholino intermediates used in this reaction are new and these form a further aspect of the invention. Thus, viewed from another aspect the invention provides an intermediate compound of formula (IX)

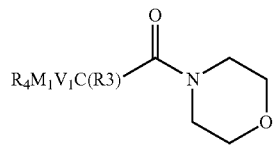

(IX)

wherein $R_4M_1V_1CH(R_3)$ is as hereinbefore defined.

Viewed from another aspect the invention provides an intermediate compound of formula (IX')

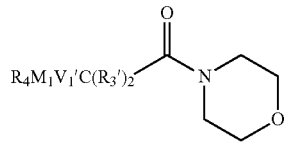

(IX')

wherein $R_4M_1V_1C(R_3)_2$ is as hereinbefore defined.

There are still further ways of developing a 2-oxo thiazole ring carrying a substituent. The ring itself can be generated from a thioamide as described in scheme 3.

Scheme 3.

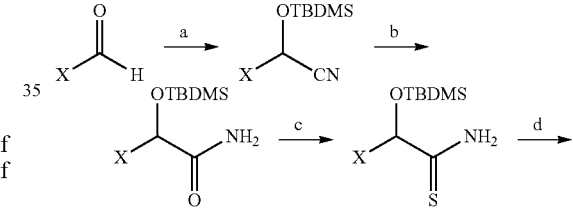

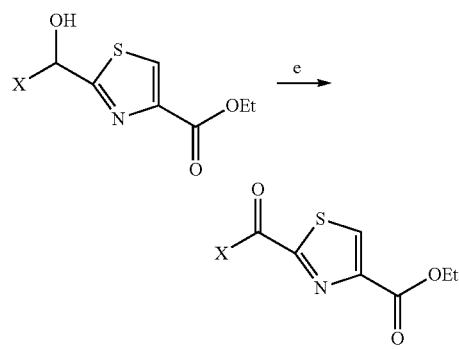

(a) TBDMSCN, KCN; (b) H$_2$O$_2$, Bu$_4$NHSO$_4$; (c) Lawesson's reagent; (d) BrCH$_2$COCOOEt; (e) Dess Martin periodinane.

As noted above, an interesting class of compounds of the invention are those having a fluoro atom adjacent the carbonyl. This is conveniently introduced before attachment of the ring system by conventional chemistry. A hydroxy group may be converted to a fluoro group using Diethylaminosulfur trifluoride (DAST) for example. This chemistry is elucidated below:

Scheme 4.

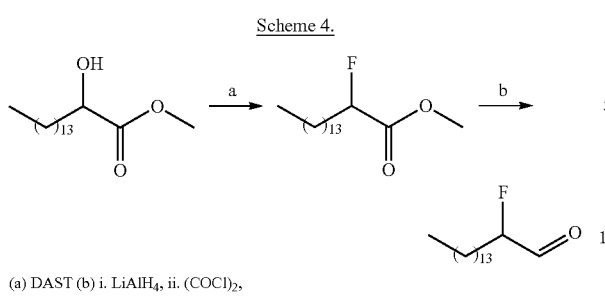

(a) DAST (b) i. LiAlH₄, ii. (COCl)₂,

The formed compound can react with thiazole as described above. Variations of the substituents on the heterocyclic rings and manipulation of the side chain binding the carbonyl can be achieved using all manner of synthetic techniques which the skilled man will know. Guidance is offered in the examples as to how to make a wide variety of compounds and the principles described can be extended to the compounds encompassed by the claims.

The principles described above for preparing thiazoles can be extended to the oxazole species.

Intermediates

Various intermediates are also new and form a further aspect of the invention. In particular, the invention covers the reduced analogue of the final 2-oxoheterocycle, i.e. a 2-hydroxy analogue. Thus, viewed from another aspect the invention provides a compound of formula (VIII)

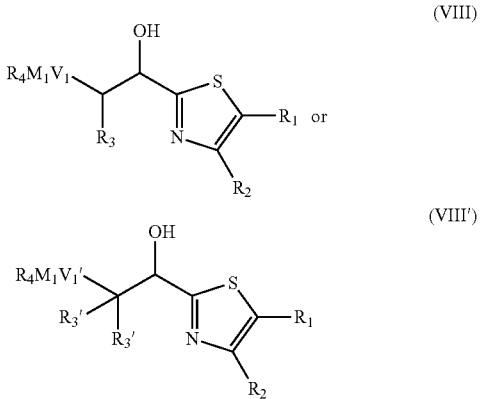

wherein $R_1$, $R_2$, $R_3$, $R_{3'}$, $R_5$ and $R_4M_1V_1/R_4M_1V_{1'}$ are as hereinbefore defined;

or a salt, ester, solvate, N-oxide, or prodrug thereof;

preferably with the proviso that $R_4M_1V_1C(R_3)$ or $R_4M_1V_1C(R_3)_2$ is not oleyl.

Chronic Inflammatory Disorders

The compounds of the invention are used in the treatment of chronic inflammatory disorders, in particular those associated with phospholipase inhibition.

Preferably, any compound of the invention will achieve 90% inhibition against IVa PLA₂.

Preferably, compounds of the invention inhibit IVa cPLA₂ at a low µM range such as 5 µM or less, preferably 4 µM or less.

It is further preferred that the compounds of the invention show greater inhibition of IVa cPLA₂ than iPLA₂ or sPLA₂ according to published assays for these enzymes (see, for example, Yang, H et al. (1999) *Anal. Biochem.* 269: 278).

Ideally, the compounds of the invention show limited or no inhibition of iPLA₂ or sPLA₂ and they are therefore highly specific for the IVa cPLA₂ enzyme.

Specific diseases of interest are glomerulonephritis, inflammatory dermatoses such as psoriasis and rheumatoid arthritis.

Further conditions of interest include other inflammatory dermatoses such as atopic dermatitis, allergic contact dermatitis, seborrheic dermatitis, pityriasis rosea, lichen planus and drug eruptions.

Furthermore the compounds of the invention may have use in the treatment of other types of arthritis and dermatoses, inflammatory CNS diseases, multiple sclerosis, chronic obstructive pulmonary disease, chronic lung inflammatory conditions, inflammatory bowel disease such as ulcerative colitis and crohns disease and cardiovascular disease.

Thus viewed from a further aspect the invention provides for the treatment of any of the conditions listed above using the compounds of the invention.

Formulation

The compounds of the invention are preferably formulated as pharmaceutically acceptable compositions. The phrase "pharmaceutically acceptable", as used in connection with compositions of the invention, refers to molecular entities and other ingredients of such compositions that are physiologically tolerable and do not typically produce untoward reactions when administered to a mammal (e.g. human). Preferably, as used herein, the term "pharmaceutically acceptable" means approved by a regulatory agency of the Federal or a state government or listed in the U.S. Pharmacopoeia or other generally recognized pharmacopoeia for use in mammals, and more particularly in humans.

The term "carrier" applied to pharmaceutical compositions of the invention refers to a diluent, excipient, or vehicle with which an active compound is administered. Such pharmaceutical carriers can be sterile liquids, such as water, saline solutions, aqueous dextrose solutions, aqueous glycerol solutions, and oils, including those of petroleum, animal, vegetable or synthetic origin, such as peanut oil, soybean oil, mineral oil, sesame oil and the like. Suitable pharmaceutical carriers are described in "Remington's Pharmaceutical Sciences" by E. W. Martin, 18th Edition, incorporated by reference. Particularly preferred for the present invention are carriers suitable for immediate-release, i.e., release of most or all of the active ingredient over a short period of time, such as 60 minutes or less, and make rapid absorption of the drug possible.

The compounds of the invention can be administered in salt, solvate, prodrug or ester form, especially salt form. Typically, a pharmaceutical acceptable salt may be readily prepared by using a desired acid. The salt may precipitate from solution and be collected by filtration or may be recovered by evaporation of the solvent. For example, an aqueous solution of an acid such as hydrochloric acid may be added to an aqueous suspension of a compound of formula (I) and the resulting mixture evaporated to dryness (lyophilised) to obtain the acid addition salt as a solid. Alternatively, a compound of formula (I) may be dissolved in a suitable solvent, for example an alcohol such as isopropanol, and the acid may be added in the same solvent or another suitable solvent. The resulting acid addition salt may then be precipitated directly, or by addition of a less polar solvent such as diisopropyl ether or hexane, and isolated by filtration.

Suitable addition salts are formed from inorganic or organic acids which form non-toxic salts and examples are hydrochloride, hydrobromide, hydroiodide, sulphate, bisulphate, nitrate, phosphate, hydrogen phosphate, acetate, trifluoroacetate, maleate, malate, fumarate, lactate, tartrate, citrate, formate, gluconate, succinate, pyruvate, oxalate, oxaloacetate, trifluoroacetate, saccharate, benzoate, alkyl or aryl sulphonates (eg methanesulphonate, ethanesulphonate, benzenesulphonate or p-toluenesulphonate) and isethionate. Representative examples include trifluoroacetate and formate salts, for example the bis or tris trifluoroacetate salts and the mono or diformate salts, in particular the tris or bis trifluoroacetate salt and the monoformate salt.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Solvates of the compounds of the invention are within the scope of the invention. The salts of the compound of Formula (I) may form solvates (e.g. hydrates) and the invention also includes all such solvates.

The term "prodrug" as used herein means a compound which is converted within the body, e.g. by hydrolysis in the blood, into its active form that has medical effects.

The compounds of the invention are proposed for use in the treatment of, inter alia, chronic inflammatory disorders. By treating or treatment is meant at least one of:
(i). preventing or delaying the appearance of clinical symptoms of the disease developing in a mammal;
(ii). inhibiting the disease i.e. arresting, reducing or delaying the development of the disease or a relapse thereof or at least one clinical or subclinical symptom thereof, or
(iii). relieving or attenuating one or more of the clinical or subclinical symptoms of the disease.

The benefit to a subject to be treated is either statistically significant or at least perceptible to the patient or to the physician. In general a skilled man can appreciate when "treatment" occurs.

The word "treatment" is also used herein to cover prophylactic treatment, i.e. treating subjects who are at risk of developing a disease in question.

The compounds of the invention can be used on any animal subject, in particular a mammal and more particularly to a human or an animal serving as a model for a disease (e.g. mouse, monkey, etc.).

An "effective amount" means the amount of a compound that, when administered to an animal for treating a state, disorder or condition, is sufficient to effect such treatment. The "effective amount" will vary depending on the compound, the disease and its severity and the age, weight, physical condition and responsiveness of the subject to be treated and will be ultimately at the discretion of the attendant doctor.

While it is possible that, for use in the methods of the invention, a compound of formula I may be administered as the bulk substance, it is preferable to present the active ingredient in a pharmaceutical formulation, for example, wherein the agent is in admixture with a pharmaceutically acceptable carrier selected with regard to the intended route of administration and standard pharmaceutical practice.

The term "carrier" refers to a diluent, excipient, and/or vehicle with which an active compound is administered. The pharmaceutical compositions of the invention may contain combinations of more than one carrier. Such pharmaceutical carriers can be sterile liquids, such as water, saline solutions, aqueous dextrose solutions, aqueous glycerol solutions, and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin, 18th Edition. The choice of pharmaceutical carrier can be selected with regard to the intended route of administration and standard pharmaceutical practice. The pharmaceutical compositions may comprise as, in addition to, the carrier any suitable binder(s), lubricant(s), suspending agent(s), coating agent(s), and/or solubilizing agent(s).

It will be appreciated that pharmaceutical compositions for use in accordance with the present invention may be in the form of oral, parenteral, transdermal, inhalation, sublingual, topical, implant, nasal, or enterally administered (or other mucosally administered) suspensions, capsules or tablets, which may be formulated in conventional manner using one or more pharmaceutically acceptable carriers or excipients.

There may be different composition/formulation requirements depending on the different delivery systems. Likewise, if the composition comprises more than one active component, then those components may be administered by the same or different routes.

The pharmaceutical formulations of the present invention can be liquids that are suitable for oral, mucosal and/or parenteral administration, for example, drops, syrups, solutions, injectable solutions that are ready for use or are prepared by the dilution of a freeze-dried product but are preferably solid or semisolid as tablets, capsules, granules, powders, pellets, pessaries, suppositories, creams, salves, gels, ointments; or solutions, suspensions, emulsions, or other forms suitable for administration by the transdermal route or by inhalation.

The compounds of the invention can be administered for immediate-, delayed-, modified-, sustained-, pulsed-or controlled-release applications.

In one aspect, oral compositions are slow, delayed or positioned release (e.g., enteric especially colonic release) tablets or capsules. This release profile can be achieved without limitation by use of a coating resistant to conditions within the stomach but releasing the contents in the colon or other portion of the GI tract wherein a lesion or inflammation site has been identified or a delayed release can be achieved by a coating that is simply slow to disintegrate or the two (delayed and positioned release) profiles can be combined in a single formulation by choice of one or more appropriate coatings and other excipients. Such formulations constitute a further feature of the present invention.

Pharmaceutical compositions can be prepared by mixing a therapeutically effective amount of the active substance with a pharmaceutically acceptable carrier that can have different forms, depending on the way of administration. Typically composition components include one or more of binders, fillers, lubricants, odorants, dyes, sweeteners, surfactants, preservatives, stabilizers and antioxidants.

The pharmaceutical compositions of the invention may contain from 0.01 to 99% weight-per volume of the active material. The therapeutic doses will generally be between about 10 and 2000 mg/day and preferably between about 30 and 1500 mg/day. Other ranges may be used, including, for example, 50-500 mg/day, 50-300 mg/day, 100-200 mg/day.

Administration may be once a day, twice a day, or more often, and may be decreased during a maintenance phase of the disease or disorder, e.g. once every second or third day instead of every day or twice a day. The dose and the administration frequency will depend on the clinical signs, which confirm maintenance of the remission phase, with the reduction or absence of at least one or more preferably more than one clinical signs of the acute phase known to the person skilled in the art.

It is within the scope of the invention for a compound as described herein to be administered in combination with another pharmaceutical, e.g. another drug with known efficacy against the disease in question. The compounds of the invention may therefore be used in combination therapy.

The invention will now be further described with reference to the following non limiting examples:

The chemistry described in the following schemes is used to manufacture the compounds described in the tables which follow. The starting materials in each scheme are readily available compounds. In general, molar equivalents of each reactant are employed.

The chemistry described in the following schemes is used to manufacture the compounds described in the tables which follow. The starting materials in each scheme are readily available compounds. In general, molar equivalents of each reactant are employed.

Experimental Procedures for the Formation of Compounds

A. To a solution of thiazole (1.1 mmol) in dry THF (2 mL) under argon atmosphere and at −78° C., n-BuLi solution (1.1 mmol, 2.5 M in hexanes) was added dropwise over a period of 5 min. After stirring at −78° C. for 30 min, a solution of the appropriate aldehyde (1 mmol) in dry THF (2 mL) was added and the mixture was stirred for additional 4 hours at −78° C. Then, $H_2O$ was added and the mixture was extracted thrice with EtOAc. The organic layer was dried ($Na_2SO_4$) and concentrated under reduced pressure. Purification by flash eluting with the appropriate mixture of EtOAc: petroleum ether (40-60° C.) afforded the desired product.

B. To a solution of the hydroxy-heterocycle (1 mmol) in dry $CH_2Cl_2$ (10 mL), Dess-Martin periodinane was added (1.5 mmol) and the mixture was stirred for 1 h at rt. The organic solution was washed with 10% aqueous $NaHCO_3$, dried over $Na_2SO_4$ and concentrated under reduced pressure. The residue was purified by column-chromatography using the appropriate mixture of EtOAc: petroleum ether (40-60° C.) as eluent.

C. To a stirred solution of the carboxylic acid (1 mmol) in $CH_2Cl_2$ (7 mL), 4-dimethylaminopyridine (DMAP) (1 mmol), N,O-dimethyl hydroxyamine hydrochloride (1 mmol), N-methylmorpholine (1 mmol) and N-(3-dimethylaminopropyl)-N'-ethyl carbodiimide hydrochloride (WSCI.HCl) (1 mmol) were added consecutively at room temperature. The reaction mixture was left stirring for 18 h. It was then washed with an aqueous solution of 10% citric acid (3×10 mL), brine (10 mL), an aqueous solution of $NaHCO_3$ 5% (3×10 mL) and brine (10 mL). The organic layer was dried ($Na_2SO_4$) and concentrated under reduced pressure. The amide was purified by flash chromatography eluting with the appropriate mixture of EtOAc: petroleum ether (40-60° C.) to afford the desired product.

D. To a stirred solution of acid (1 mmol) in dry $CH_2Cl_2$ (7 mL), DMF (0.5 eq.) was added followed by oxalyl chloride (3 mmol) at room temperature. The reaction mixture was left stirring for 3 h. The solvent was removed and dry $Et_2O$ (7 mL) was added and cooled at 0° C. Pyridine (5 mmol) was added drop-wise, followed by drop-wise addition of morpholine (5 mmol). The reaction mixture was left stirring for 18 h at room temperature. Then, $H_2O$ (8 mL) was added and it was left stirring for 30 min. The layers were separated and the organic layer was washed with an aqueous solution of HCl 1N (3×10 mL), brine (1×10 mL), an aqueous solution of $NaHCO_3$ 5% (3×10 mL) and brine (1×10 mL). The organic layer was dried ($Na_2SO_4$) and concentrated under reduced pressure. Purification by flash chromatography eluting with the appropriate mixture of EtOAc: petroleum ether (40-60° C.) afforded the desired product.

E. To a stirred solution of thiazole or benzothiazole (3 mmol) in dry $Et_2O$ (20 mL) at −78° C. under a dry argon atmosphere was added a solution of n-BuLi (1.6 M in hexanes, 3 mmol) drop-wise over a period of 10 min. The resulting orange solution was stirred for 45 min. Then, a solution of the amide (1 mmol) in dry $Et_2O$ (2 mL) was slowly added giving the mixture a dark brown color. After stirring for 30 min. at −78° C., the mixture was allowed to warm up to room temperature over a period of 2 h. Then, saturated aqueous ammonium chloride solution was added and the mixture was extracted with ether (2×10 mL). The combined extracts were washed with brine and then dried over $Na_2SO_4$ and concentrated under reduced pressure. Purification by flash chromatography eluting with the appropriate mixture of EtOAc: petroleum ether (40-60° C.) afforded the desired product.

F. To a stirred solution of the ester (1 mmol) in dry $Et_2O$ (10 mL) was added dropwise DIBALH (1.1 mL, 1.0 M in hexane, 1.1 mmol) at 0° C. The reaction was stirred for 10 min and then quenched with $H_2O$. The mixture was stirred for 30 min, dried over $Na_2SO_4$, and filtered through a pad of Celite. The solvent was evaporated and the crude product was purified by silica gel column chromatography.

G. To a solution of the alcohol (1 mmol) in a mixture of toluene-EtOAc (6 mL), a solution of NaBr (1.05 mmol) in water (0.5 mL) was added, followed by AcNH-TEMPO (0.01 mmol). To the resulting biphasic system, which was cooled at −5° C., an aqueous solution of 0.35 M NaOCl (3.14 mL, 1.10 mmol) containing $NaHCO_3$ (3 mmol) was added dropwise while stirring vigorously at −5° C. over a period of 1 h. After the mixture had been stirred for a further 15 min at 0° C., EtOAc (6 mL) and $H_2O$ (2 mL) were added. The aqueous layer was separated and washed with EtOAc (4 mL). The combined organic layers were washed consecutively with 5% aqueous citric acid (6 mL) containing 5% KI, 10% aqueous $Na_2S_2O_3$ (6 mL), and brine and dried over $Na_2SO_4$. The solvents were evaporated under reduced pressure, and the residue was used immediately in the next step without any purification.

H. A solution of the aldehyde (1 mmol) in $CH_2Cl_2$ (2 mL) was added to a mixture of tert-butyl dimethylsilylcyanide (1 mmol), potassium cyanide (0.17 mmol) and 18-crown-6 (0.4 mmol) under argon atmosphere. The mixture was stirred for 1 h. The solvent was evaporated and the crude product was purified by silica gel column chromatography eluting with the appropriate mixture of EtOAc: petroleum ether (40-60° C.) to afford the desired product.

I. To a solution of the cyanide (1 mmol) in $CH_2Cl_2$ (20 mL) at 0° C. was added 30% $H_2O_2$ (0.5 mL), tetrabutyammonium hydrogen sulfate (0.2 mmol) and an aqueous solution of 0.5 N NaOH (1.2 mmol). The reaction mixture was stirred in a sealed flask for 18 h during which additional $H_2O_2$ (0.5 mL) were added thrice. $H_2O$ and $CH_2Cl_2$ were added and the organic layer was separated, washed with brine and dried over $Na_2SO_4$. The crude product was purified by silica gel column chromatography eluting with the appropriate mixture of EtOAc: petroleum ether (40-60° C.) to afford the desired product.

J. Lawesson's reagent (0.6 mmol) was added to a solution of the amide (1 mmol) in dry toluene (10 mL) under argon atmosphere. The reaction mixture was stirred for 18 h at room temperature. The solvent was evaporated and the crude product was purified by silica gel column chromatography eluting with the appropriate mixture of EtOAc: petroleum ether (40-60° C.) to afford the desired product.

K. To a solution of the thioamide (1 mmol) in ethanol (3.2 mL) under argon atmosphere, was added ethyl bromopyruvate or ethyl 4-chloroacetoacetate (1 mmol) and concentrated $H_2SO_4$ (10 µL). The reaction mixture was stirred for 18 h. The solvent was evaporated and the crude product was purified by silica gel column chromatography eluting with the appropriate mixture of EtOAc: petroleum ether (40-60° C.) to afford the desired product.

L. To a solution of the hydroxyl heterocyclic ester (1 mmol) in EtOH (25 mL), an aqueous solution of 1 N NaOH (20 mmol, 20 mL) was added. After stirring for 1 h, the solution was acidified with aqueous solution of 1N HCl and the product was extracted with $Et_2O$. The organic layer was separated, washed with brine and dried over $Na_2SO_4$. The product was used in the next step without any purification.

M. To a solution of the oxo heterocyclic ester (1 mmol) in EtOH (25 mL), an aqueous solution of 20% $Cs_2CO_3$ (20 mmol, 20 mL) was added. After stirring for 18 h, the solution was acidified with aqueous solution of 1N HCl and the product was extracted with $Et_2O$. The organic layer was separated, washed with brine and dried over $Na_2SO_4$. The product was purified by recrystallization.

N. To a stirred solution of $LiAlH_4$ (1M in THF, 2.9 mmol) in dry $Et_2O$ (5.5 mL) under argon atmosphere and at −20° C. a solution of the ester (1 mmol) in dry $Et_2O$ (5.5 mL) was added. The reaction was stirred for 20 min at −20° C. and for 20 min at rt. Then, it was cooled at 0° C. and quenched with $H_2O$. The mixture was stirred for 30 min at rt. Then, additional $H_2O$ was added and the mixture was acidified with 1 N HCl to pH 5. The aqueous layer was washed twice with $Et_2O$, and then the combined organic layers were washed with brine, dried over $Na_2SO_4$, and the solvent was evaporated. The crude product was purified by silica gel column chromatography eluting with the appropriate mixture of EtOAc: petroleum ether (40-60° C.) to afford the desired product.

O. To a stirred solution of the alcohol (1 mmol) in acetone (4.2 mL), $K_2CO_3$ (3 mmol) was added followed by a catalytic amount of KI and the appropriate bromide (1.1 mmol). The solution was refluxed for 18 h, the solvent was evaporated, and $H_2O$ and EtOAc were added. The aqueous layer was washed twice with EtOAc and then the combined organic layers were washed with brine, dried over $Na_2SO_4$, and the solvent was evaporated. The crude product was purified by silica gel column chromatography eluting with the appropriate mixture of EtOAc: petroleum ether (40-60° C.) to afford the desired product.

P. A solution of the hydroxy compound (1 mmol) in dry $CH_2Cl_2$ (50 mL) was treated dropwise with a solution of DAST (3 mmol) in dry $CH_2Cl_2$ (2 mL) under argon atmosphere and at −78° C. The reaction mixture was stirred for 2 h at −78° C. and for additional 16 h at rt. Then, a saturated solution of $NaHCO_3$ was added until the bubbling of $CO_2$ stopped. The solution was stirred for 20 min and then $H_2O$ and $CH_2Cl_2$ were added. The organic layer was separated, dried over $Na_2SO_4$, filtered and evaporated, and the crude product was purified by column chromatography on silica gel eluting with EtOAc-petroleum ether (bp 40-60° C.) to yield the desired fluoro derivative.

Q. A solution of oxalyl chloride (4 mmol) in dry $CH_2Cl_2$ (3 mL) under argon atmosphere and at −60° C. was treated dropwise with a solution of dry DMSO (8 mmol) in dry $CH_2Cl_2$ (3.5 mL). After 5 min, a solution of the fluoro alcohol (1 mmol) in dry $CH_2Cl_2$ (20 mL) was added dropwise and after additional 15 min, dry $Et_3N$ (16 mmol) was added. The reaction mixture was stirred for 1 h to reach room temperature. Then, the reaction mixture was poured in ice and the aqueous layer was extracted thrice with $CH_2Cl_2$. The combined organic layers were washed with brine, dried over $Na_2SO_4$, and the solvent was evaporated. The crude product was purified by silica gel column chromatography eluting with the appropriate mixture of EtOAc: petroleum ether (40-60° C.) to afford the desired product.

R. A solution of the aldehyde (1 mmol) and methyl (triphenylphosphanylidene)acetate (1.1 mmol) in dry $CH_2Cl_2$ (3 mL) under argon atmosphere was refluxed for 1 h and then left stirring for 16 h at rt. Saturated solution of $NH_4Cl$ was added and the aqueous layer was extracted thrice with $CH_2Cl_2$. The combined organic layers were washed with brine, dried over $Na_2SO_4$, and the solvent was evaporated. The crude product was purified by silica gel column chromatography eluting with the appropriate mixture of EtOAc: petroleum ether (40-60° C.) to afford the desired product.

S. A mixture of the unsaturated ester (1 mmol) in dry 1,4-dioxane (10 mL) and a catalytic amount of 10% palladium on activated carbon was hydrogenated for 18 h. After filtration through a pad of celite and the solvent was removed in vacuo. The crude product was purified by silica gel column chromatography eluting with the appropriate mixture of EtOAc: petroleum ether (40-60° C.) to afford the desired product.

T. A solution of the aldehyde (1 mmol) and $NaHSO_3$ (1.5 mmol in 1.3 mL $H_2O$) in $CH_2Cl_2$ (1.2 mL) was stirred for 30 min at room temperature. After the formation of a white salt, the organic solvent was evaporated and water (1 mL) was added. The mixture was cooled to 0° C. and an aqueous solution of KCN (1.5 mmol in 1.3 mL $H_2O$) was added dropwise. The reaction mixture was stirred for another 18 h at room temperature and then $CH_2Cl_2$ and water were added. The organic layer was washed with brine and dried ($Na_2SO_4$). The solvent was evaporated under reduced pressure and the residual oil was purified by column chromatography on silica gel eluting with the appropriate mixture of EtOAc: petroleum ether (40-60° C.).

U. The cyanhydrine (1 mmol) was treated with 6N HCl (10 mL) in MeOH for 18 h at room temperature. The organic solvent was evaporated and a saturated aqueous solution of $K_2CO_3$ was added to pH neutralization. After extraction with $CH_2Cl_2$ (3×15 mL), the combined organic phases were washed with brine and dried ($Na_2SO_4$). The solvent was evaporated under reduced pressure and the residual oil was purified by column chromatography on silica gel eluting with the appropriate mixture of EtOAc: petroleum ether (40-60° C.).

V. To a stirred solution of the Z-protected amino compound (1 mmol) in MeOH (8 mL) were added successively a catalytic amount of 10% Pd/C and anhydrous ammonium formate (5 mmol). After stirring for 2 h at rt, the reaction mixture was filtered over celite. The organic layer was then concentrated under reduced pressure to yield the crude product, which was used without any further purification.

W. To a stirred solution of phenylacetic acid (1.0 mmol) and the amino component (1.0 mmol) in dry $CH_2Cl_2$ (10 mL), $Et_3N$ (1.1 mmol) and subsequently 1-(3-dimethylaminopropyl)-3-ethyl carbodiimide (WSCI) (1.1 mmol) and 1-hydroxybenzotriazole (HOBt) (1.0 mmol) were added at 0° C. The reaction mixture was stirred for 1 h at 0° C. and overnight at rt. The solvent was evaporated under reduced pressure and EtOAc (20 mL) was added. The organic layer was washed consecutively with brine, 1N HCl, brine, 5% $NaHCO_3$, and brine, dried over $Na_2SO_4$ and evaporated under reduced pressure. The residue was purified by column chromatography on silica gel eluting with the appropriate mixture of EtOAc: petroleum ether (40-60° C.).

X. A solution of the tert-butyl ester derivative (1 mmol) in 50% $TFA/CH_2Cl_2$ (10 mL) was stirred for 1 h at room temperature. The organic solvent was evaporated under reduced pressure to afford the desired product.

Compounds 1-3

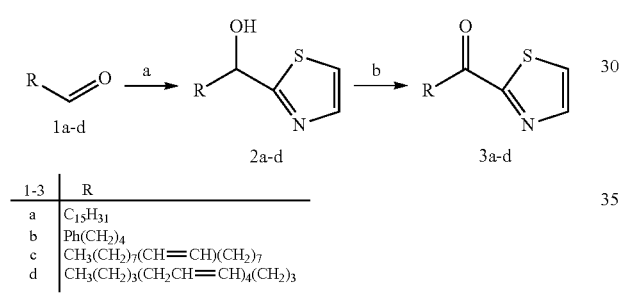

| 1-3 | R |
|---|---|
| a | $C_{15}H_{31}$ |
| b | $Ph(CH_2)_4$ |
| c | $CH_3(CH_2)_7(CH=CH)(CH_2)_7$ |
| d | $CH_3(CH_2)_3(CH_2CH=CH)_4(CH_2)_3$ |

(a) thiazole, n-BuLi, dry THF, -78° C.; (b) Dess-Martin periodinane, dry $CH_2Cl_2$.

Characterising Data 1-(Thiazol-2-yl)hexadecan-1-ol (2a)

Procedure A

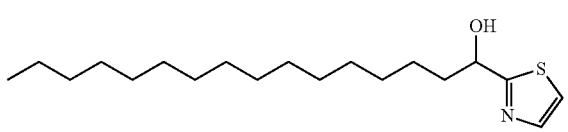 [SMILES: CCCCCCCCCCCCCCCC(O)c1nccs1]

White solid. Yield 51%.
m.p. 69-71° C.
$^1$H NMR: δ 7.68 (d, 1H, J=2.8 Hz, ArH), 7.25 (d, 1H, J=2.8 Hz, ArH), 4.97 (m, 1H, CHOH), 3.14 (br s, 1H, OH), 1.86 (m, 2H, $CH_2$CHOH), 1.48-1.13 (m, 26H, 13×$CH_2$), 0.86 (t, 3H, J=6.2 Hz, $CH_3$).
$^{13}$C NMR: δ 175.6, 142.0, 118.8, 71.8, 38.3, 31.9, 29.7, 29.6, 29.6, 29.5, 29.4, 29.3, 25.2, 22.7, 14.1.

5-Phenyl-1-(thiazol-2-yl)pentan-1-ol (2b)

Procedure A

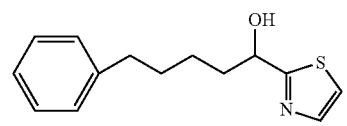 [SMILES: OC(CCCCc1ccccc1)c1nccs1]

Colorless Oil. Yield 42%.
$^1$H NMR: δ 7.65 (d, 1H, J=3.4 Hz, ArH), 7.33-7.16 (m, 6H, Ph, ArH), 4.97 (m, 1H, CHOH), 4.5 (br, 1H, OH), 2.62 (t, 2H, J=7.0 Hz, $CH_2$Ph), 2.05-1.80 (m, 2H, $CH_2$CHOH), 1.74-1.45 (m, 4H, 2×$CH_2$).
$^{13}$C NMR: δ 176.3, 142.3, 141.8, 128.3, 128.2, 125.6, 118.7, 71.4, 37.9, 35.7, 31.1, 24.9.

(Z)-1-(Thiazol-2-yl)octadec-9-en-1-ol (2c)

Procedure A

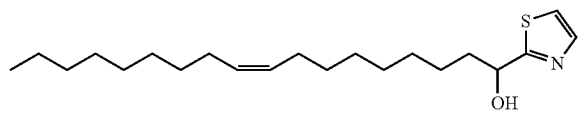 [SMILES: CCCCCCCC/C=C\CCCCCCCC(O)c1nccs1]

$C_{21}H_{37}NOS$
White oil.
$^1$H NMR (CDCl$_3$) δ: 7.69 (d, 1H, J=3.4 Hz, CHN), 7.28 (d, 1H, J=3.4 Hz, CHS), 5.34 (m, 2H, CH=CH), 4.97 (dd, 1H, $J_1$=7.4 Hz, $J_2$=5.2 Hz, CHOH), 3.47 (b, 1H, OH), 2.00 (m, 6H, 3×$CH_2$), 1.60-1.10 (m, 22H, 11×$CH_2$), 0.88 (t, 3H, J=6.2 Hz, $CH_3$).
$^{13}$C NMR (CDCl$_3$) δ: 175.7, 142.0, 129.9, 129.8, 118.7, 71.8, 38.3, 31.9, 29.7, 29.5, 29.3, 29.2, 27.1, 25.2, 22.6, 14.1.

(5Z,8Z,11Z,14Z)-1-(Thiazol-2-yl)icosa-5,8,11,14-tetraen-1-ol (2d)

Procedure A

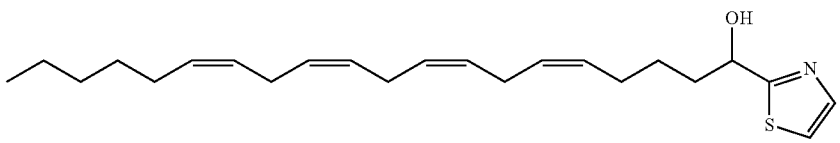 [SMILES: CCCCC/C=C\C/C=C\C/C=C\C/C=C\CCCC(O)c1nccs1]

C₂₃H₃₅NOS
MW: 373.60.
White oil.
¹H NMR (CDCl₃) δ: 7.64 (d, 1H, J=3.0 Hz, ArH), 7.23 (d, 1H, J=3.0 Hz, ArH), 5.56-5.21 (m, 8H, 4×CH=CH), 4.96 (dd, 1H, J₁=6.8 Hz, J₂=5.0 Hz, CHOH), 4.20-3.90 (br, 1H, OH), 2.98-2.63 (m, 6H, 3×CHCH₂CH), 2.18-1.79 (m, 6H, 3×CH₂), 1.69-1.18 (m, 8H, 4×CH₂), 0.90 (t, 3H, J=6.6 Hz, CH₃).
¹³C NMR (CDCl₃) δ: 175.8, 141.9, 130.4, 129.5, 128.5, 128.2, 128.0, 127.9, 127.8, 127.5, 118.7, 71.5, 37.7, 31.4, 29.2, 27.1, 26.8, 25.5, 25.4, 25.1, 22.5, 14.0.
MS (ESI) m/z (%): 373 [M⁺, 100].

1-(Thiazol-2-yl)hexadecan-1-one (3a)

Procedure B

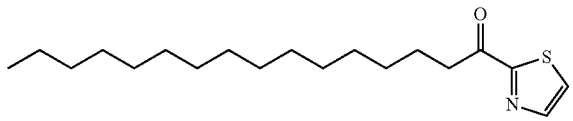 [SMILES: CCCCCCCCCCCCCCCC(=O)c1nccs1]

C₁₉H₃₃NOS
MW: 323.54.
White solid.
m.p.: 39-41° C.
¹H NMR (200 MHz, CDCl₃) δ=7.98 (d, 1H, J=3.0 Hz, ArH), 7.65 (d, 1H, J=3.0 Hz, ArH), 3.14 (t, 2H, J=7.4 Hz, CH₂CO), 1.81-1.68 (m, 2H, CH₂CH₂CO), 1.42-1.10 (m, 24H, 12×CH₂), 0.86 (t, 3H, J=5.0 Hz, CH₃).
¹³C NMR (50 MHz, CDCl₃) δ=194.1, 167.3, 144.6, 126.0, 38.5, 31.9, 29.6, 29.4, 29.3, 29.2, 24.0, 22.7, 14.1.
MS (ESI) m/z (%): 324 [M+H, 100]⁺.

5-Phenyl-1-(thiazol-2-yl)pentan-1-one (3b)

Procedure B

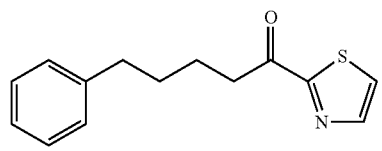 [SMILES: O=C(CCCCc1ccccc1)c1nccs1]

C₁₄H₁₅NOS
MW: 245.34.
Yellow oil.
¹H NMR (200 MHz, CDCl₃) δ=8.00 (d, 1H, J=3.0 Hz, ArH), 7.66 (d, 1H, J=2.8 Hz, ArH), 7.33-7.13 (m, 5H, Ph), 3.21 (t, 2H, J=6.6 Hz, CH₂CO), 2.68 (t, 2H, J=7.6 Hz, PhCH₂), 1.92-1.65 (m, 4H, 2×CH₂).

¹³C NMR (50 MHz, CDCl₃) δ=193.8, 167.1, 144.5, 142.0, 128.3, 128.2, 126.1, 125.6, 38.2, 35.6, 30.9, 23.6.

(Z)-1-(Thiazol-2-yl)octadec-9-en-1-one (3c)

Procedure B

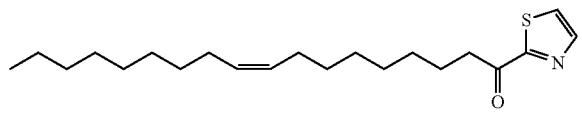 [SMILES: CCCCCCCC/C=C\CCCCCCCC(=O)c1nccs1]

C₂₁H₃₅NOS
Yellowish oil.
¹H NMR (CDCl₃) δ: 8.00 (d, 1H, J=3.0 Hz, CHN), 7.66 (d, 1H, J=3.0 Hz, CHS), 5.34 (m, 2H, CH=CH), 3.16 (t, 2H, J=8.0 Hz, CH₂CO), 2.01 (m, 4H, 2×CH₂CH=), 1.80-1.60 (m, 2H, CH₂), 1.60-1.10 (m, 20H, 10×CH₂), 0.88 (t, 3H, J=6.2 Hz, CH₃). ¹³C NMR (CDCl₃) δ: 194.1, 167.4, 144.6, 130.0, 129.7, 126.0, 38.5, 32.6, 31.9, 29.7, 29.5, 29.3, 29.2, 29.1, 27.2, 24.0, 22.7, 14.1.

(5Z,8Z,11Z,14Z)-1-(Thiazol-2-yl)icosa-5,8,11,14-tetraen-1-one (3d)

Procedure B

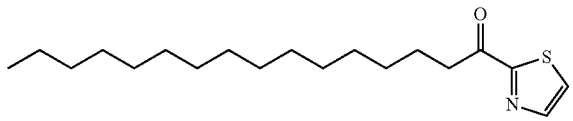 [SMILES: CCCCCCCCCCCCCCCC(=O)c1nccs1]

C₂₃H₃₃NOS
Yellowish oil.
¹H NMR (CDCl₃) δ: 8.00 (d, 1H, J=2.8 Hz, ArH), 7.66 (d, 1H, J=2.8 Hz, ArH), 5.42-5.21 (m, 8H, 4×CH=CH), 3.19 (t, 2H, J=7.2 Hz, CH₂CO), 2.88-2.63 (m, 6H, 3×CHCH₂CH), 2.25-2.20 (m, 4H, 2×CH₂), 1.45-1.17 (m, 2H, CH₂), 1.40-1.20 (m, 6H, 3×CH₂), 0.88 (t, 3H, J=6.4 Hz, CH₃).
¹³C NMR (CDCl₃) δ: 193.9, 167.2, 144.6, 130.4, 129.1, 128.9, 128.5, 128.2, 128.1, 127.9, 127.5, 126.1, 37.8, 31.5, 29.3, 29.2, 27.2, 26.6, 25.6, 23.9, 22.5, 14.0.

Compounds 3 to 5 (Alternative Strategies)

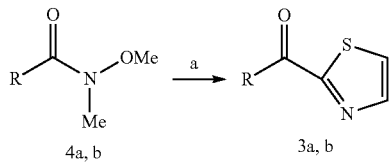

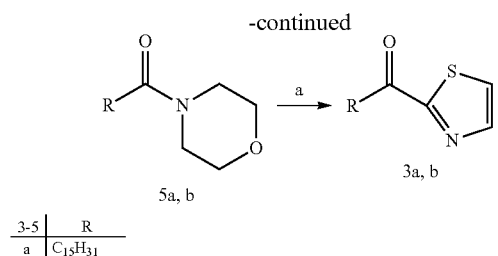

| 3-5 | R |
|---|---|
| a | C₁₅H₃₁ |
| b | Ph(CH₂)₄ |

(a) thiazole, n-BuLi, dry Et₂O, -78° C..

N-Methoxy-N-methyl-palmitamide (4a)

Procedure C

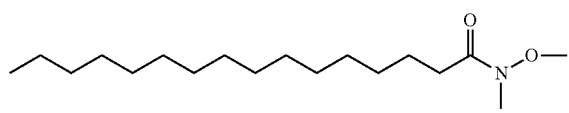 [SMILES: CCCCCCCCCCCCCCCC(=O)N(C)OC]

$C_{18}H_{37}NO_2$
MW: 299.49.
colorless oil. Yield 81%.
$^1$H NMR (200 MHz, CDCl$_3$) δ=3.66 (s, 3H, OMe), 3.16 (s, 3H, NMe), 2.39 (t, 2H, J=7.6 Hz, CH$_2$CO), 1.70-1.57 (m, 2H, CH$_2$CH$_2$CO), 1.23-1.08 (m, 24H, 12×CH$_2$), 0.86 (t, 3H, J=3.8 Hz, CH$_3$).
$^{13}$C NMR (50 MHz, CDCl$_3$) δ=174.6, 61.0, 31.8, 29.5, 29.4, 29.3, 24.8, 24.5, 22.5, 13.9. MS (ESI) m/z (%): 300 [M+H, 100]$^+$.

N-Methoxy-N-methyl-5-phenylpentanamide (4b)
(by the Weinreb method)

Procedure C

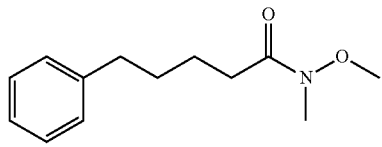 [SMILES: CON(C)C(=O)CCCCc1ccccc1]

$C_{13}H_{19}NO_2$
MW: 221.30.
Colorless oil. Yield 81%.
$^1$H NMR (200 MHz, CDCl$_3$) δ=7.33-7.12 (m, 5H, Ph), 3.65 (s, 3H, OMe), 3.17 (s, 3H, NMe), 2.65 (t, 2H, J=7.2 Hz, PhCH$_2$), 2.44 (t, 2H, J=7.2 Hz, CH$_2$CO), 1.72-1.66 (m, 4H, 2×CH$_2$).
$^{13}$C NMR (50 MHz, CDCl$_3$) δ=174.6, 142.2, 128.2, 128.1, 125.6, 61.0, 35.6, 31.6, 31.1, 24.2.
MS (ESI) m/z (%): 222 [M+H, 100]$^+$.

General Procedure for the Synthesis of Morpholine Amides

To a stirred solution of acid (1 eq.) in dry CH$_2$Cl$_2$ (7 mL), DMF (0.5 eq.) was added followed by oxalyl chloride (3 eq.) at room temperature. The reaction mixture was left stirring for 3 h. The solvent was removed and dry Et$_2$O (7 mL) was added and cooled at 0° C. Pyridine (5 eq.) was added drop-wise, followed by drop-wise adittion of morpholine (5 eq.). The reaction mixture was left stirring for 18 h at room temperature. Then, H$_2$O (8 mL) was added and it was left stirring for 30 min. The layers were separated and the organic layer was washed with an aqueous solution of HCl 1N (3×10 mL), brine (1×10 mL), an aqueous solution of NaHCO$_3$ 5% (3×10 mL) and brine (1×10 mL). The organic layer was dried (Na$_2$SO$_4$) and concentrated under reduced pressure. Purification by flash chromatography eluting with the appropriate mixture of EtOAc: pet. ether (40-60° C.) afforded the desired product.

1-Morpholinohexadecan-1-one (5a)

Procedure D

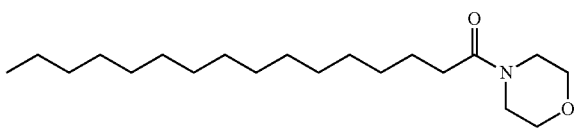 [SMILES: CCCCCCCCCCCCCCCC(=O)N1CCOCC1]

$C_{20}H_{39}NO_2$
MW: 325.53.
White solid. Yield 99%.
m.p.: 45-46° C.
$^1$H NMR (200 MHz, CDCl$_3$) δ=3.66-3.60 (m, 6H, CH$_2$OCH$_2$, CHHNCHH), 3.43-3.38 (m, 2H, CHHNCHH), 2.28 (t, 2H, J=7.2 Hz, CH$_2$CO), 1.63-1.52 (m, 2H, CH$_2$CH$_2$CO), 1.34-1.06 (m, 24H, 12×CH$_2$), 0.85 (t, 3H, J=5.8 Hz, CH$_3$).
$^{13}$C NMR (50 MHz, CDCl$_3$) δ=171.8, 66.8, 66.6, 45.9, 41.7, 33.0, 31.8, 29.6, 29.5, 29.4, 29.3, 29.2, 25.2, 22.6, 14.0.
MS (ESI) m/z (%): 326 [M+H, 100]$^+$.

1-Morpholino-5-phenylpentan-1-one (5b)

Procedure D

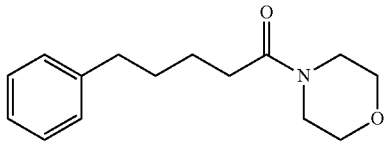 [SMILES: O=C(CCCCc1ccccc1)N1CCOCC1]

$C_{15}H_{21}NO_2$
MW: 247.33.
Colorless oil. Yield 74% (1.025 g).
$^1$H NMR (200 MHz, CDCl$_3$) δ=7.26-7.09 (m, 5H, Ph), 3.64-3.42 (m, 6H, CH$_2$OCH$_2$, CHHNCHH), 3.41-3.23 (m, 2H, CHHNCHH), 2.61 (t, 2H, J=7.0 Hz, PhCH$_2$), 2.27 (t, 2H, J=7.2 Hz, CH$_2$CO), 1.69-1.60 (m, 4H, 2×CH$_2$).
$^{13}$C NMR (50 MHz, CDCl$_3$) δ=171.3, 141.9, 128.2, 128.1, 125.5, 66.7, 66.4, 45.7, 41.6, 35.5, 32.7, 30.9, 24.6.
MS (ESI) m/z (%): 248 [M+H, 100]$^+$, 270 [M+23, 23].

Synthesis of 2-oxo-thiazoles Using the Weinreb and Morpholino Amide Method

To a stirred solution of thiazole (3 eq.) in dry Et$_2$O (20 mL) at −78° C. under a dry argon atmosphere was added a solution of n-BuLi (1.6 M in hexanes, 3 eq.) drop-wise over a period of 10 min. The resulting orange solution was stirred for 45 min. Then a solution of the amide (1 eq.) in dry $Et_2O$ (2 mL) was slowly added giving the mixture a dark brown color. After stirring for 30 min. at −78° C., the mixture was allowed to warm up to room temperature over a period of 2 h. Then, saturated aqueous ammonium chloride solution was added and the mixture was extracted with ether (2×10 mL). The combined extracts were washed with brine and then dried over $Na_2SO_4$ and concentrated under reduced pressure. Purification by flash chromatography eluting with the appropriate mixture of EtOAc: pet. ether (40-60° C.) afforded the desired product.

1-(Thiazol-2-yl)hexadecan-1-one (3a)

Procedure E

Yield when the Weinreb amide was used: 73%.
Yield when the morpholine amide was used: 98%.

5-Phenyl-1-(thiazol-2-yl)pentan-1-one (3b)

Procedure E

Yield when the Weinreb amide was used: 85%.
Yield when the morpholine amide was used: 86%.

Compounds 6 to 9

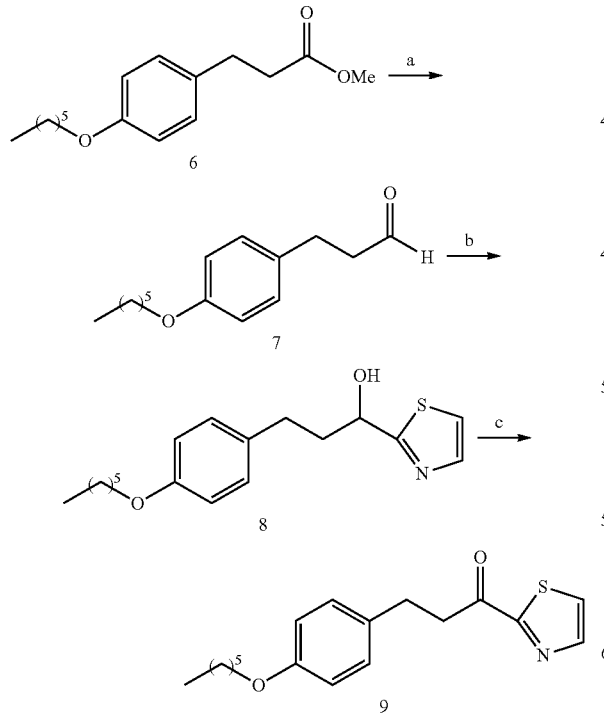

(a) i. DIBALH, $Et_2O$, 0° C., ii. NaOCl, $NaHCO_3$, NaBr, 4-AcNH—TEMPO, toluene, AcOEt, $H_2O$, -5° C.; (b) thiazole, n-BuLi, dry THF, -78° C.; (c) Dess-Martin periodinane, dry $CH_2Cl_2$.

3-(4-(Hexyloxy)phenyl)propanal (7)

Procedure F then G

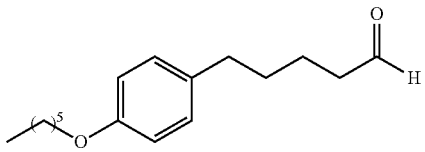

$C_{15}H_{22}O_2$
MW: 234.33
Orange oil. Yield 64%.
$^1$H NMR (200 MHz, $CDCl_3$) δ=9.80 (s, 1H, CHO), 7.09 (d, 2H, J=8.4 Hz, CH), 6.82 (d, 2H, J=8.6 Hz, 2×CH), 3.92 (t, 2H, J=6.4 Hz, $CH_2$), 3.00-2.85 (m, 2H, $CH_2$), 2.80-2.65 (m, 2H, $CH_2$), 1.85-1.65 (m, 2H, $CH_2$), 1.50-1.20 (m, 6H, 3×$CH_2$), 0.92 (m, 3H, $CH_3$).
$^{13}$C NMR (50 MHz, $CDCl_3$) δ=201.7, 157.6, 132.0, 129.1, 114.5, 67.9, 45.5, 31.5, 29.2, 27.2, 25.7, 22.5, 14.0

3-(4-(Hexyloxy)phenyl)-1-(thiazol-2-yl)propan-1-ol (8)

Procedure A

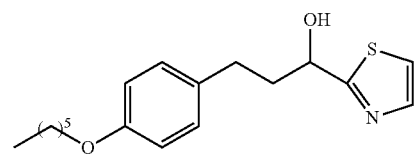

$C_{18}H_{25}NO_2S$
MW: 319.46
Colorless oil. Yield 66%.
$^1$H NMR (200 MHz, $CDCl_3$) δ=7.65 (d, 1H, J=3.2 Hz, ArH), 7.24 (d, 1H, J=3.4 Hz, ArH), 7.07 (d, 2H, J=8.8 Hz, 2×CH), 6.79 (d, 2H, J=8.6 Hz, 2×CH), 4.96 (dd, 1H, J=7.6 Hz, $J_2$=5.0 Hz, CH), 3.90 (t, 2H, J=6.4 Hz, $CH_2O$), 2.80-2.60 (m, 2H, $CH_2$), 2.25-2.05 (m, 2H, $CH_2$), 1.85-1.65 (m, 2H, $CH_2$), 1.50-1.30 (m, 6H, 3×$CH_2$), 0.88 (t, 3H, J=6.2 Hz, $CH_3$).
$^{13}$C NMR (50 MHz, $CDCl_3$) δ=175.9, 157.4, 142.0, 133.0, 129.3, 118.8, 114.4, 70.9, 67.9, 39.9, 31.5, 30.5, 29.2, 25.6, 22.5, 14.0.

3-(4-(Hexyloxy)phenyl)-1-(thiazol-2-yl)propan-1-one (9)

Procedure B

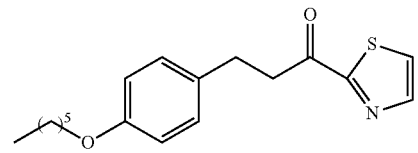

$C_{18}H_{23}NO_2S$
MW: 317.45
Yellowish oil. Yield 78%.

$^1$H NMR (200 MHz, $CDCl_3$) δ=7.95 (d, 1H, J=3.2 Hz, ArH), 7.62 (d, 1H, J=3.4 Hz, ArH), 7.15 (d, 2H, J=8.8 Hz, CH), 6.81 (d, 2H, J=8.4 Hz, CH), 3.90 (t, 2H, J=6.6 Hz, $CH_2O$), 3.45 (t, 2H, J=7.2 Hz, $CH_2$), 3.01 (t, 2H, J=3.8 Hz, $CH_2$), 1.90-1.64 (m, 2H, $CH_2$), 1.58-1.20 (m, 6H, 3×$CH_2$), 0.89 (t, 3H, J=6.6 Hz, $CH_3$).

$^{13}$C NMR (50 MHz, $CDCl_3$) δ=193.1, 167.1, 157.5, 144.6, 132.5, 129.3, 126.1, 114.5, 68.0, 40.3, 31.5, 29.2, 28.9, 25.7, 22.6, 14.0.

MS (ESI) m/z (%): 318 [M+H, 100]$^+$.

Compounds 10 to 15

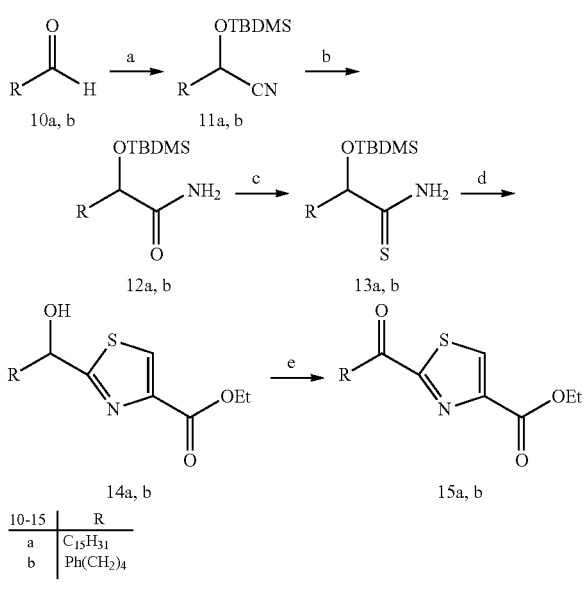

| 10-15 | R |
|---|---|
| a | $C_{15}H_{31}$ |
| b | $Ph(CH_2)_4$ |

(a) TBDMSCN, KCN, 18-crown-6, $CH_2Cl_2$; (b) 30% $H_2O_2$, $Bu_4NHSO_4$, NaOH, $CH_2Cl_2$; (c) Lawesson's reagent, THF; (d) $BrCH_2COCOOEt$, conc. $H_2SO_4$, EtOH, 40° C.; (e) Dess Martin periodinane, dry $CH_2Cl_2$.

2-(tert-Butyldimethylsilyloxy)heptadecanenitrile (11a)

Procedure H

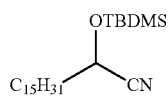

$C_{23}H_{47}NOSi$
MW: 381.71
Colorless oil. Yield 85%.

$^1$H NMR (200 MHz, $CDCl_3$) δ=4.41 (t, 1H, J=6.4 Hz, CH), 1.70-1.90 (m, 2H, $CH_2$), 1.40-1.55 (m, 2H, $CH_2$), 1.30-1.15 (m, 24H, 12×$CH_2$), 1.03-0.82 (m, 12H, 4×$CH_3$), 0.19 (s, 3H, $CH_3$), 0.14 (s, 3H, $CH_3$).

$^{13}$C NMR (50 MHz, $CDCl_3$) δ=120.1, 61.9, 36.3, 31.9, 29.6, 29.5, 29.4, 29.3, 28.9, 25.5, 24.5, 22.7, 18.0, −5.2, −5.4.

2-(tert-Butyldimethylsilyloxy)-6-phenylhexanenitrile (11b)

Procedure H

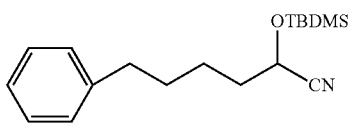 [SMILES: CC(C)(C)[Si](C)(C)OC(C#N)CCCCc1ccccc1]

$C_{18}H_{29}NOSi$
MW: 303.51
Colorless oil. Yield 82%.

$^1$H NMR ($CDCl_3$): δ=7.34-7.20 (m, 5H, Ph), 4.44 (t, 1H, J=6.6 Hz, CH), 2.68 (t, 2H, J=7.4 Hz, 1.88-1.80 (m, 2H, $CH_2$), 1.76-1.69 (m, 2H, $CH_2$), 1.68-1.58 (m, 2H, $CH_2$), 0.97 (s, 9H, 3×$CH_3$), 0.23 (s, 3H, $CH_3$), 0.18 (s, 3H, $CH_3$).

$^{13}$C NMR ($CDCl_3$) δ=142.0, 128.3, 128.0, 125.8, 120.1, 61.8, 36.1, 35.6, 30.8, 25.7, 25.5, 24.1, 18.0, −5.2, −5.4.

2-(tert-Butyldimethylsilyloxy)heptadecanamide (12a)

Procedure I

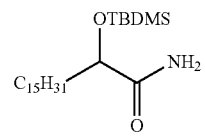

$C_{23}H_{49}NO_2Si$
MW: 399.73
Yellow oil. Yield 63%.

$^1$H NMR (200 MHz, $CDCl_3$) δ=6.49 (s, 1H, NHH), 6.14 (s, 1H, NHH), 4.10 (t, 1H, J=5.0 Hz, CH), 1.80-1.56 (m, 2H, $CH_2$), 1.40-1.10 (m, 26H, 13×$CH_2$), 0.95-0.80 (m, 12H, 4×$CH_3$), 0.17 (s, 3H, $CH_3$), 0.14 (s, 3H, $CH_3$).

$^{13}$C NMR (50 MHz, $CDCl_3$) δ 177.3, 73.4, 35.1, 31.9, 29.7, 29.6, 29.5, 29.4, 29.3, 25.7, 24.1, 22.7, 18.0, 14.1, −4.9, −5.3.

MS (ESI) m/z (%) δ=400 [M+H, 40]$^+$, 422 [M+Na, 100]$^+$.

2-(tert-Butyldimethylsilyloxy)-6-phenylhexanamide (12b)

Procedure I

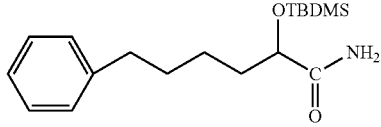 [SMILES: CC(C)(C)[Si](C)(C)OC(CCCCc1ccccc1)C(N)=O]

$C_{18}H_{31}NO_2Si$
MW: 321.53
Colorless oil. Yield 100%.

$^1$H NMR ($CDCl_3$): δ=7.28-7.15 (m, 5H, Ph), 6.51 (s, 1H, NH), 5.61 (s, 1H, NH), 4.16 (t, 1H, J=6.6 Hz, CH), 2.62 (t,

2H, J=7.4 Hz, CH$_2$), 1.77-1.32 (m, 6H, 3×CH$_2$), 0.91 (s, 9H, 3×CH$_3$), 0.06 (s, 6H, 2×CH$_3$).

$^{13}$C NMR (CDCl$_3$): δ=177.4, 142.3, 128.2, 128.1, 125.5, 73.2, 35.6, 34.8, 31.2, 25.6, 23.8, 17.8, −5.0, −5.4.

MS (ESI) m/z (%): 322 [M+H, 100]$^+$.

2-(tert-Butyldimethylsilyloxy)heptadecanethioamide (13a)

Procedure J

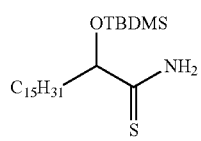

C$_{23}$H$_{49}$NOSSi
MW: 415.79
Yellowish oil. Yield 84%.

$^1$H NMR (200 MHz, CDCl$_3$) δ=7.96 (s, 1H, NHH), 7.74 (s, 1H, NHH), 4.56 (t, 1H, J=5.0 Hz, CH), 1.90-1.70 (m, 2H, CH$_2$), 1.47-1.15 (m, 26H, 13×CH$_2$), 1.00-0.83 (m, 12H, 4×CH$_3$), 0.12 (s, 3H, CH$_3$), 0.09 (s, 3H, CH$_3$).

$^{13}$C NMR (50 MHz, CDCl$_3$) δ=210.3, 80.1, 38.0, 32.1, 29.9, 29.8, 29.7, 29.6, 26.0, 25.7, 24.1, 22.9, 18.3, 14.3, −4.7, −4.9.

MS (ESI) m/z (%): 416 [M+H, 90]$^+$.

2-(tert-Butyldimethylsilyloxy)-6-phenylhexanethioamide (13b)

Procedure J

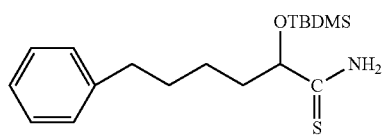 [SMILES: CC(C)(C)[Si](C)(C)OC(CCCCc1ccccc1)C(N)=S]

C$_{18}$H$_{31}$NOSSi
MW: 337.60
Yellowish oil. Yield 64%.

$^1$H NMR (CDCl$_3$): δ=8.28 (s, 1H, NH), 7.98 (s, 1H, NH), 7.24-7.10 (m, 5H, Ph), 4.52 (t, 1H, J=6.6 Hz, CH), 2.57 (t, 2H, J=7.4 Hz, CH$_2$), 1.95-1.80 (m, 2H, CH$_2$), 1.62-1.45 (m, 2H, CH$_2$), 1.42-1.25 (m, 2H, CH$_2$), 0.88 (s, 9H, 3×CH$_3$), 0.06 (s, 3H, SiCH$_3$), 0.04 (s, 3H, SiCH$_3$).

$^{13}$C NMR (CDCl$_3$): 209.6, 142.3, 128.3, 128.1, 125.5, 79.6, 37.4, 35.6, 31.2, 25.6, 23.5, 17.9, −5.1, −5.3.

MS (ESI) m/z (%): 338 [M+H, 100]$^+$.

Ethyl 2-(1-hydroxyhexadecyl)thiazole-4-carboxylate (14a)

Procedure K

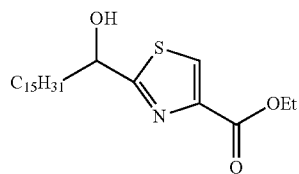

C$_{22}$H$_{39}$NO$_3$S
MW: 397.61
Yellowish solid. Yield 74%.

$^1$H NMR (200 MHz, CDCl$_3$) δ=8.06 (s, 1H, CH), 5.03 (dd, 1H, J$_1$=4.5 Hz, J$_2$=8.1 Hz, CH), 4.36 (q, 2H, J=7.1 Hz, CH$_2$), 3.10-2.90 (br, 1H, OH), 2.00-1.60 (m, 2H, CH$_2$), 1.35 (t, 3H, J=7.1 Hz, CH$_3$), 1.40-1.10 (m, 26H, 13×CH$_2$), 0.85 (t, 3H, J=6.8 Hz, CH$_3$).

$^{13}$C NMR (50 MHz, CDCl$_3$) δ=177.3, 161.4, 146.6, 127.1, 71.8, 61.3, 38.1, 31.8, 29.6, 29.5, 29.4, 29.3, 29.2, 25.5, 25.1, 22.6, 14.2, 14.0.

Ethyl 2-(1-hydroxy-5-phenylpentyl)thiazole-4-carboxylate (14b)

Procedure K

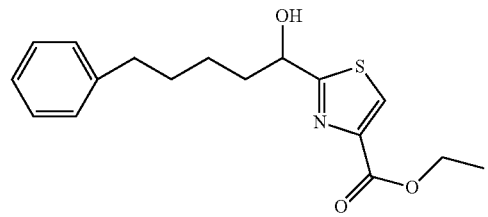 [SMILES: CCOC(=O)c1csc(C(O)CCCCc2ccccc2)n1]

C$_{17}$H$_{21}$NO$_3$S
MW: 319.42
Yellowish oil. Yield 45%.

$^1$H NMR (CDCl$_3$): δ=8.03 (s, 1H, ArH), 7.25-7.10 (m, 5H, Ph), 5.11-5.00 (m, 1H, CH), 4.33 (q, 2H, J=5.8 Hz, OCH$_2$), 4.10-3.95 (m, 1H, OH), 2.56 (t, 2H, J=7.0 Hz, CH$_2$), 1.85-1.78 (m, 2H, CH$_2$), 1.62-1.41 (m, 2H, CH$_2$), 1.32 (t, 3H, J=5.8 Hz, CH$_3$), 1.24-1.20 (m, 2H, CH$_2$).

$^{13}$C NMR (CDCl$_3$): δ=177.4, 161.3, 146.4, 142.2, 128.2, 128.1, 127.2, 125.5, 71.5, 61.3, 37.8, 35.5, 30.9, 24.7, 14.2.

Ethyl 2-palmitoylthiazole-4-carboxylate (15a)

Procedure B

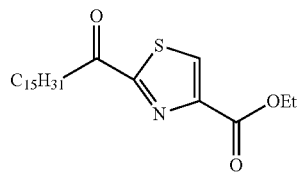

$C_{22}H_{37}NO_3S$
MW: 395.60
White solid. Yield 82%.
$^1$H NMR (200 MHz, CDCl$_3$): δ=8.41 (s, 1H, CH), 4.46 (q, 2H, J=6.8 Hz, CH$_2$), 3.23 (t, 2H, J=7.4 Hz, CH$_2$), 1.85-1.60 (m, 4H, 2×CH$_2$), 1.43 (t, 3H, J=6.8 Hz, CH$_3$), 1.42-1.00 (m, 22H, 11×CH$_2$), 0.88 (t, 3H, J=6.8 Hz, CH$_3$).
$^{13}$C NMR (50 MHz, CDCl$_3$): δ=194.3, 167.9, 161.1, 148.9, 133.2, 62.0, 38.6, 32.1, 29.9-29.8, 29.7, 29.6, 29.5, 29.3, 23.8, 22.9, 14.5, 14.3.
MS (ESI) m/z (%): 418 [M+Na, 100]$^+$.

Ethyl 2-(5-phenylpentanoyl)thiazole-4-carboxylate (15b)

Procedure B

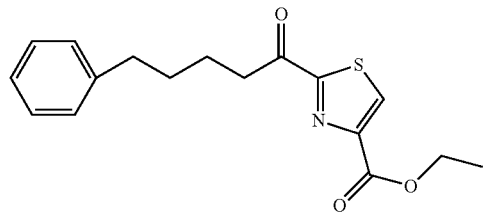 [SMILES: CCOC(=O)c1csc(C(=O)CCCCc2ccccc2)n1]

$C_{17}H_{19}NO_3S$
MW: 317.40
Yellowish oil. Yield 81%
$^1$H NMR (CDCl$_3$): δ=8.38 (s, 1H, ArH), 7.24-7.13 (m, 5H, Ph), 4.42 (q, 2H, J=5.8 Hz, OCH$_2$), 3.23 (t, 2H, J=5.8 Hz, CH$_2$), 2.63 (t, 2H, J=7.0 Hz, CH$_2$CO), 1.81-1.65 (m, 4H, 2×CH$_2$), 1.39 (t, 3H, J=5.8 Hz, CH$_3$).
$^{13}$C NMR (CDCl$_3$): 193.8, 167.4, 160.8, 148.6, 142.0, 133.1, 128.3, 128.2, 125.7, 61.8, 38.1, 35.6, 30.7, 23.2, 14.3.
MS (ESI) m/z (%): 318 [M+H, 100]$^+$.
Compounds 16 to 19

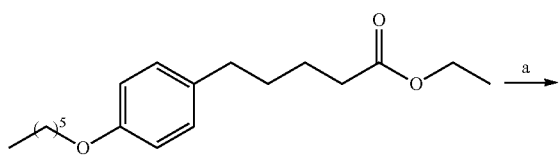

16

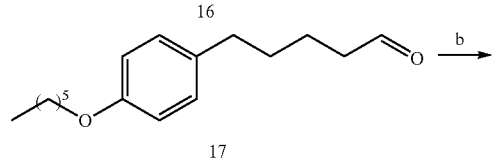

17

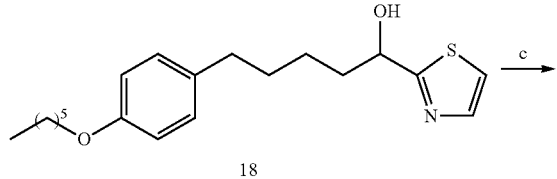

18

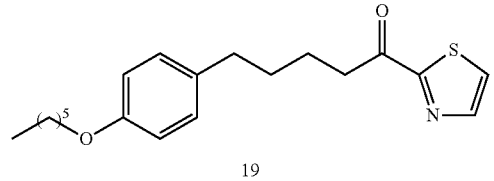

19

-continued
(a) i. LiAlH$_4$, dry Et$_2$O, -20° C., ii. NaOCl, NaHCO$_3$, NaBr, 4-AcNH—TEMPO, toluene, AcOEt, H$_2$O, -5° C.; (b) thiazole, n-BuLi, dry THF, -78° C.; (c) NaOCl, NaHCO$_3$, NaBr, 4-AcNH—TEMPO, toluene, AcOEt, H$_2$O, -5 °C.

5-(4-(Hexyloxy)phenyl)pentanal (17)

Procedure N then G

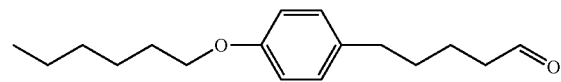 [SMILES: CCCCCCOc1ccc(CCCCC=O)cc1]

$C_{17}H_{26}O_2$
MW: 262.39.
Yellowish oil. Yield 97%.
$^1$H NMR (200 MHz, CDCl$_3$) δ=9.73 (t, 1H, J=1.8 Hz, CHO), 7.06 (d, 2H, J=8.6 Hz, CH, Ph), 6.81 (d, 2H, J=8.6 Hz, CH, Ph), 3.92 (t, 2H, J=6.4 Hz, CH$_2$OPh), 2.56 (t, 2H, J=7.0 Hz, PhCH$_2$), 2.47-2.35 (m, 2H, CH$_2$CHO), 1.81-1.67 (m, 2H, CH$_2$CH$_2$OPh), 1.65-1.57 (m, 4H, 2×CH$_2$), 1.55-1.09 (m, 6H, 3×CH$_2$), 0.90 (t, 3H, J=6.8 Hz, CH$_3$).
$^{13}$C NMR (50 MHz, CDCl$_3$) δ=202.3, 157.2, 133.6, 129.0, 114.2, 67.8, 43.6, 34.6, 31.5, 31.0, 29.2, 25.6, 22.5, 21.5, 20.8, 13.9.

5-(4-(Hexyloxy)phenyl)-1-(thiazol-2-yl)pentan-1-ol (18)

Procedure A

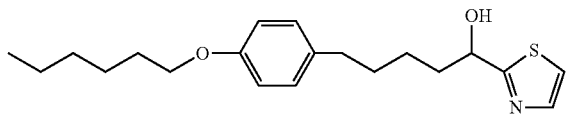 [SMILES: CCCCCCOc1ccc(CCCCC(O)c2nccs2)cc1]

$C_{20}H_{29}NO_2S$
MW: 347.51.
Orange oil. Yield 74%.
$^1$H NMR (200 MHz, CDCl$_3$) δ=7.62 (d, 1H, J=3.2 Hz, ArH), 7.22 (d, 1H, J=3.4 Hz, ArH), 7.03 (d, 2H, J=8.8 Hz, CH, Ph), 6.77 (d, 2H, J=8.6 Hz, CH, Ph), 4.98-4.84 (m, 1H, CHOH), 4.46 (d, 1H, J=5 Hz, CHOH), 3.89 (t, 2H, J=6.4 Hz, CH$_2$OPh), 2.52 (t, 2H, J=7 Hz, PhCH$_2$), 2.48-1.19 (m, 14H, 7×CH$_2$), 0.88 (t, 3H, J=6.6 Hz, CH$_3$).
$^{13}$C NMR (50 MHz, CDCl$_3$) δ=176.3, 157.0, 141.9, 134.2, 129.0, 118.5, 114.1, 71.5, 67.8, 38.0, 34.7, 31.5, 31.3, 29.2, 25.6, 24.7, 22.5, 20.9, 14.0.
MS (ESI) m/z (%): 348 [M+H, 100]$^+$.

5-(4-(Hexyloxy)phenyl)-1-(thiazol-2-yl)pentan-1-one (19)

Procedure G

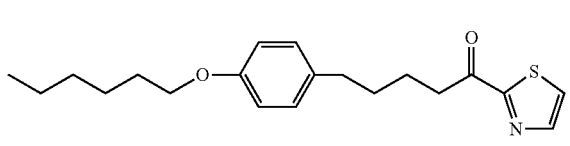 [SMILES: CCCCCCOc1ccc(CCCCC(=O)c2nccs2)cc1]

$C_{20}H_{27}NO_2S$

MW: 345.50.

Yellowish oil. Yield 89%.

$^1$H NMR (200 MHz, CDCl$_3$) δ=7.98 (d, 1H, J=3.2 Hz, ArH), 7.65 (d, 1H, J=3.4 Hz, ArH), 7.08 (d, 2H, J=8.8 Hz, CH, Ph), 6.81 (d, 2H, J=8.4 Hz, CH, Ph), 3.91 (t, 2H, J=6.6 Hz, CH$_2$OPh), 3.18 (t, 2H, J=6.8 Hz, CH$_2$CO), 2.60 (t, 2H, J=7.6 Hz, PhCH$_2$), 1.89-1.61 (m, 6H, 3×CH$_2$), 1.48-1.28 (m, 6H, 3×CH$_2$), 0.90 (t, 3H, J=6.6 Hz, CH$_3$).

$^{13}$C NMR (50 MHz, CDCl$_3$) δ=193.7, 167.1, 157.2, 144.5, 133.9, 129.1, 126.1, 114.2, 67.8, 38.2, 34.6, 31.5, 31.1, 29.2, 25.6, 23.5, 22.5, 14.0.

MS (ESI) m/z (%): 346 [M+H, 100]$^+$

Compounds 20 to 24

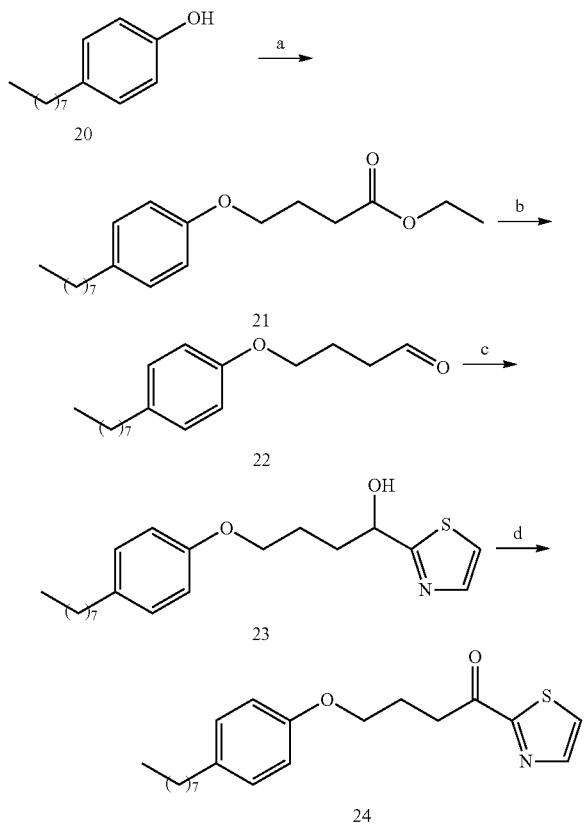

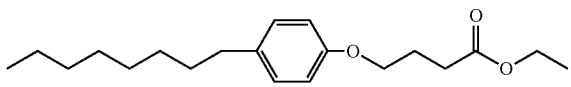 [SMILES: CCCCCCCCc1ccc(OCCCC(=O)OCC)cc1]

(a) Br(CH$_2$)$_3$COOC$_2$H$_5$, K$_2$CO$_3$ KI, acetone, reflux; (b) i. LiAlH$_4$, dry Et$_2$O, -20° C., ii. NaOCl, NaHCO$_3$, NaBr, 4-AcNH—TEMPO, toluene, AcOEt, H$_2$O, -5 ° C.; (c) thiazole, n-BuLi, dry Et$_2$O, -78° C.; (d) NaOCl, NaHCO$_3$, NaBr, 4-AcNH—TEMPO, toluene, AcOEt, H$_2$O, -5° C.

Ethyl 4-(4-octylphenoxy)butanoate (21)

Procedure O $C_{20}H_{32}O_3$

MW: 320.47.

Colorless oil. Yield 100%.

$^1$H NMR (200 MHz, CDCl$_3$) δ=7.08 (d, 2H, J=7.8 Hz, CH, Ph), 6.81 (d, 2H, J=7.6 Hz, CH, Ph), 4.15 (q, 2H, J=7.0 Hz, COOCH$_2$), 3.99 (t, 2H, J=5.8 Hz, PhOCH$_2$), 2.58-2.42 (m, 4H, 2×CH$_2$), 2.17-2.06 (m, 2H, CH$_2$CH$_2$COO), 1.57-1.45 (m, 2H, CH$_2$CH$_2$Ph), 1.27 (br, 13H, 5×CH$_2$, CH$_3$), 0.89 (t, 3H, J=5.2 Hz, CH$_3$).

$^{13}$C NMR (50 MHz, CDCl$_3$) δ=173.2, 156.8, 135.0, 129.1, 114.2, 66.6, 60.3, 35.0, 31.7, 30.8, 29.4, 29.2, 24.6, 22.6, 14.1, 14.0.

MS (ESI) m/z (%): 321 [M+H, 100]$^+$.

4-(4-Octylphenoxy)butanal (22)

Procedure N then G

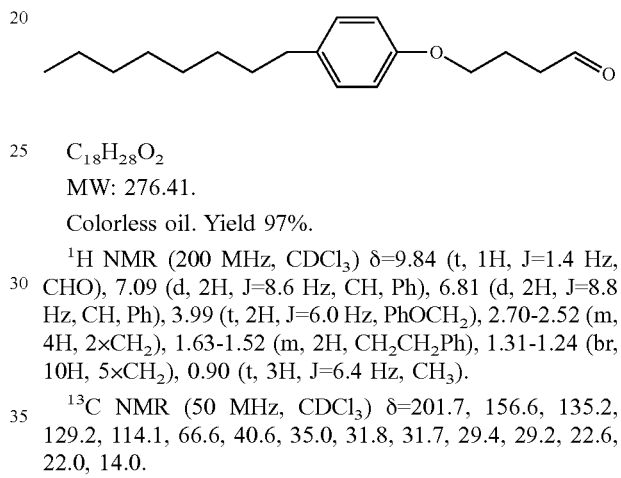

$C_{18}H_{28}O_2$

MW: 276.41.

Colorless oil. Yield 97%.

$^1$H NMR (200 MHz, CDCl$_3$) δ=9.84 (t, 1H, J=1.4 Hz, CHO), 7.09 (d, 2H, J=8.6 Hz, CH, Ph), 6.81 (d, 2H, J=8.8 Hz, CH, Ph), 3.99 (t, 2H, J=6.0 Hz, PhOCH$_2$), 2.70-2.52 (m, 4H, 2×CH$_2$), 1.63-1.52 (m, 2H, CH$_2$CH$_2$Ph), 1.31-1.24 (br, 10H, 5×CH$_2$), 0.90 (t, 3H, J=6.4 Hz, CH$_3$).

$^{13}$C NMR (50 MHz, CDCl$_3$) δ=201.7, 156.6, 135.2, 129.2, 114.1, 66.6, 40.6, 35.0, 31.8, 31.7, 29.4, 29.2, 22.6, 22.0, 14.0.

4-(4-Octylphenoxy)-1-(thiazol-2-yl)butan-1-ol (23)

Procedure A

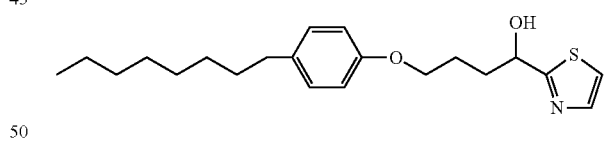

$C_{21}H_{31}NO_2S$

MW: 361.54.

Orange oil. Yield 73%.

$^1$H NMR (200 MHz, CDCl$_3$) δ=7.72 (d, 1H, J=3.2 Hz, ArH), 7.29 (d, 1H, J=3.2 Hz, ArH), 7.08 (d, 2H, J=8.8 Hz, CH, Ph), 6.81 (d, 2H, J=8.6 Hz, CH, Ph), 5.11 (dd, 1H, J$_1$=4.4 Hz, J$_2$=7.6 Hz, CHOH), 4.00 (t, 2H, J=6.0 Hz, PhOCH$_2$), 3.92 (s, 1H, OH), 2.54 (t, 2H, J=7.2 Hz, CH$_2$Ph), 2.32-1.90 (m, 4H, 2×CH$_2$), 1.67-1.48 (m, 2H, CH$_2$CH$_2$Ph), 1.30-1.23 (br, 10H, 5×CH$_2$), 0.88 (t, 3H, J=6.2 Hz, CH$_3$).

$^{13}$C NMR (50 MHz, CDCl$_3$) δ=175.4, 156.6, 142.0, 135.3, 129.2, 118.9, 114.3, 71.5, 67.7, 35.1, 35.0, 31.9, 31.7, 29.5, 29.2, 25.2, 22.6, 14.1.

MS (ESI) m/z (%): 362 [M+H, 100]$^+$.

4-(4-Octylphenoxy)-1-(thiazol-2-yl)butan-1-one (24)

Procedure G

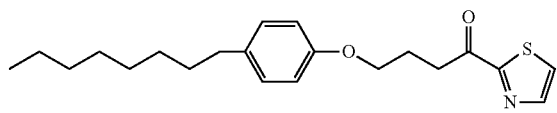 [SMILES: CCCCCCCCc1ccc(OCCCC(=O)c2nccs2)cc1]

C$_{21}$H$_{29}$NO$_2$S
MW: 359.53.
Yellowish oil. Yield 85%.
$^1$H NMR (200 MHz, CDCl$_3$) δ=7.99 (d, 1H, J=3.0 Hz, ArH), 7.65 (d, 1H, J=3.0 Hz, ArH), 7.07 (d, 2H, J=8.6 Hz, CH, Ph), 6.80 (d, 2H, J=8.8 Hz, CH, Ph), 4.06 (t, 2H, J=6.2 Hz, PhOCH$_2$), 3.39 (t, 2H, J=7.2 Hz, CH$_2$C=O), 2.54 (t, 2H, J=7.4 Hz, CH$_2$Ph), 2.26 (quintet, 2H, J=6.2 Hz, CH$_2$CH$_2$C=O), 1.68-1.45 (m, 2H, CH$_2$CH$_2$Ph), 1.30-1.23 (br, 10H, 5×CH$_2$), 0.89 (t, 3H, J=6.2 Hz, CH$_3$).
$^{13}$C NMR (50 MHz, CDCl$_3$) δ=193.2, 166.9, 156.7, 144.6, 135.0, 129.1, 126.0, 114.2, 66.7, 35.1, 35.0, 31.8, 31.7, 29.4, 29.2, 23.6, 22.6, 14.0.
MS (ESI) m/z (%): 360 [M+H, 100]$^+$.

Compounds 25 to 29

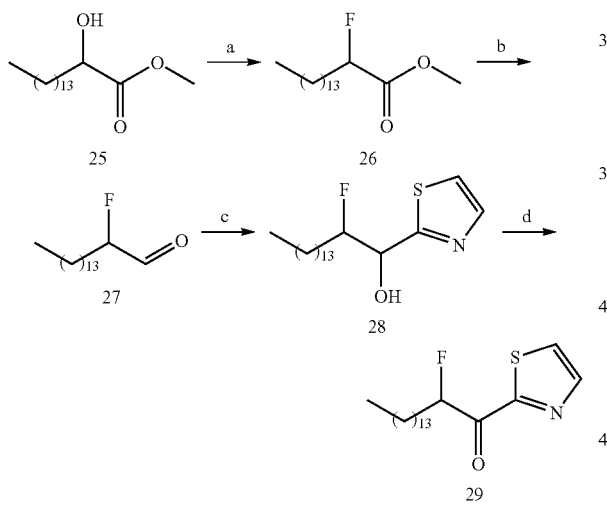

(a) DAST, dry CH$_2$Cl$_2$, -78° C.; (b) i, LiAlH$_4$, dry Et$_2$O, -20° C., ii. (COCl)$_2$, dry Et$_3$N, dry DMSO, dry CH$_2$Cl$_2$, -60° C.; (c) thiazole, n-BuLi, dry THF, -78° C.; (d) Dess-Martin periodinane, dry CH$_2$Cl$_2$.

Methyl 2-fluorohexadecanoate (26)

Procedure P

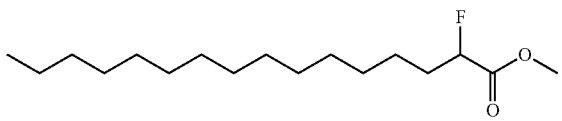 [SMILES: CCCCCCCCCCCCCCC(F)C(=O)OC]

C$_{17}$H$_{33}$FO$_2$
MW: 288.44.
White solid. Yield 78%.
m.p.: 36-38° C.
$^1$H NMR (200 MHz, CDCl$_3$) δ=4.91 (dt, 1H, J$_{H-H}$=6.0 Hz, J$_{H-F}$=48.8 Hz, CHF), 3.80 (s, 3H, COOCH$_3$), 2.00-1.77 (m, 2H, CH$_2$CHF), 1.49-1.18 (m, 24H, 12×CH$_2$), 0.88 (t, 3H, J=6.8 Hz, CH$_3$).
$^{13}$C NMR (50 MHz, CDCl$_3$) δ=170.5 (d, J$_{C-C-F}$=24 Hz, COO), 89.0 (d, J$_{C-C-F}$=183 Hz, CF), 52.2, 32.3 (d, J$_{C-C-F}$=21 Hz, CH$_2$CHF), 31.9, 29.6, 29.5, 29.4, 29.3, 29.0, 24.4, 24.3, 22.7, 14.1.
$^{19}$F NMR (186 MHz, CDCl$_3$) δ=−192.5 (quintet, CHF).

2-Fluorohexadecanal (27)

Procedure N then Q

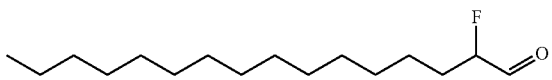 [SMILES: CCCCCCCCCCCCCCC(F)C=O]

C$_{16}$H$_{31}$FO
MW: 258.42.
White solid. Yield 86%.
m.p.: 68-71° C.
$^1$H NMR (200 MHz, CDCl$_3$) δ=9.76 (d, 1H, J=5.8 Hz, CHO), 4.74 (dt, 1H, J$_{H-H}$=4.8 Hz, J$_{H-F}$=49.0 Hz, CHF), 1.86-1.68 (m, 2H, CH$_2$CHF), 1.47-1.10 (m, 24H, 12×CH$_2$), 0.88 (t, 3H, J=5.8 Hz, CH$_3$).
$^{13}$C NMR (50 MHz, CDCl$_3$) δ=200.4 (d, J$_{C-C-F}$=36 Hz, CO), 95.0 (d, J$_{C-F}$=178 Hz, CF), 31.9, 30.3 (d, J$_{C-C-F}$=20 Hz, CH$_2$), 29.6, 29.5, 29.3, 29.2, 24.2, 24.1, 22.7, 14.1.
$^{19}$F NMR (186 MHz, CDCl$_3$) δ=−200.0 (m, CHF).

2-Fluoro-1-(thiazole-2-yl)hexadeca-1-ol (28)

Procedure A

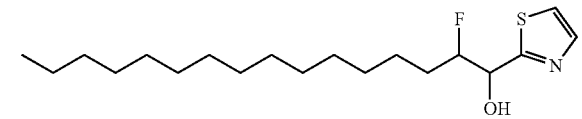 [SMILES: CCCCCCCCCCCCCCC(F)C(O)c1nccs1]

C$_{19}$H$_{34}$FNOS
MW: 343.54.
Yellowish solid. Yield 40%.
m.p.: 46-49° C.
$^1$H NMR (200 MHz, CDCl$_3$) δ=7.89 (d, 1/7H, J=3.2 Hz, ArH), 7.75 (d, 6/7H, J=3.4 Hz, ArH), 7.45 (d, 1/7H, J=3.2 Hz, ArH), 7.35 (d, 6/7H, J=3.2 Hz, ArH), 5.22-5.05 (dm, 1H, J=13.4 Hz, CHOH), 5.01-4.66 (dm, 1H, J=51.6 Hz, CHF), 4.15 (d, 2/3H, J=4.6 Hz, CHOH), 3.91 (d, 1/3H, J=5.6 Hz, CHOH), 1.94-1.08 (m, 26H, 13×CH$_2$), 0.88 (t, 3H, J=6.2 Hz, CH$_3$).
$^{13}$C NMR (50 MHz, CDCl$_3$) δ=170.0, 142.1, 119.7, 95.4 (d, J$_{C-F}$=173 Hz, CF), 73.2 (d, J$_{C-C-F}$=22 Hz, 1/3COH), 73.0 (d, J$_{C-C-F}$=24 Hz, 2/3COH) 31.9, 30.6 (d, J$_{C-C-F}$=21 Hz, CH$_2$), 29.6, 29.5, 29.4, 29.3, 25.0, 24.9, 22.7, 14.1.
$^{19}$F NMR (186 MHz, CDCl$_3$) δ=−190.2 (m, CHF), −194.3 (m, CHF)
MS (ESI) m/z (%): 344 [M+H, 100]$^+$.

37

2-Fluoro-1-(thiazole-2-yl)hexadeca-1-one (29)

Procedure B

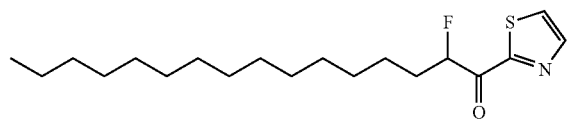 [SMILES: CCCCCCCCCCCCCCC(F)C(=O)c1nccs1]

$C_{19}H_{32}FNOS$
MW: 341.53.
White solid. Yield 60%.
m.p.: 55-56° C.

$^1$H NMR (200 MHz, CDCl$_3$) δ=8.05 (d, 1H, J=3.0 Hz, ArH), 7.76 (d, 1H, J=3.0 Hz, ArH), 6.07 (ddd, 1H, $J_{H-F}$=49.8 Hz, $J_{H-H}$=3.8 Hz, $J_{H-H}$=8.2 Hz, CHF), 2.19-1.91 (m, 2H, CH$_2$CHF), 1.66-1.08 (m, 24H, 12×CH$_2$), 0.87 (t, 3H, J=6.6 Hz, CH$_3$).

$^{13}$C NMR (50 MHz, CDCl$_3$) δ=189.4 (d, $J_{C-C-F}$=19 Hz, CO), 164.1, 145.3, 127.1, 92.9 (d, $J_{C-F}$=182 Hz, CF), 32.8 (d, $J_{C-C-F}$=21 Hz, CH$_2$), 32.1, 29.9, 29.8, 29.7, 29.6, 29.5, 29.3, 24.9, 22.9, 14.3.

$^{19}$F NMR (186 MHz, CDCl$_3$) δ=−196.6 (m, CHF).

MS (ESI) m/z (%): 342 [M+H, 100]$^+$.

Compounds 30 to

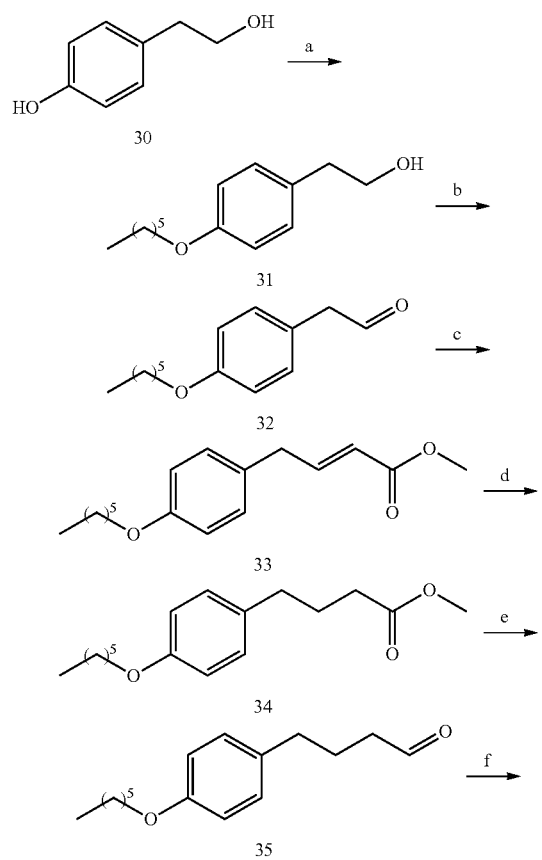

38

-continued

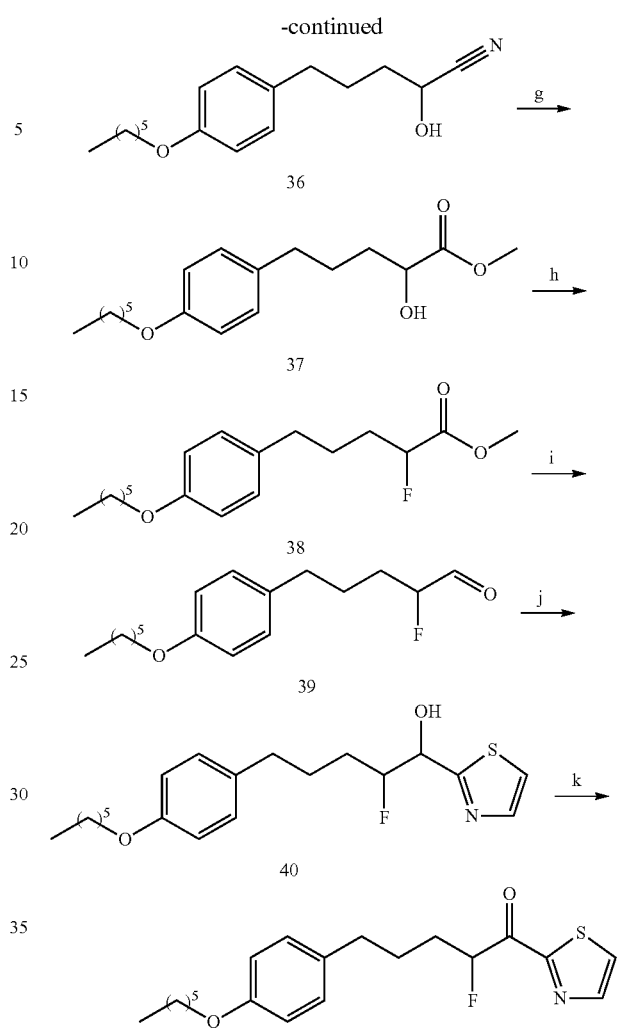

(a) CH$_3$(CH$_2$)$_5$Br, K$_2$CO, KI, acetone, reflux; (b) NaOCl, NaHCO$_3$, NaBr, 4-AcNH—TEMPO, toluene, AcOEt, H$_2$O, -5° C.; (c) Ph$_3$P=CHCOOCH$_3$, dry, THF, reflux; (d) H$_2$, 10% Pd/C, 1,4-dioxane; (e) i. LiAlH$_4$, dry Et$_2$O, -20° C., ii. NaOCl, NaHCO$_3$, NaBr, 4-AcNH—TEMPO, toluene, AcOEt, H$_2$O, -5° C.; (f) NAHSO$_3$, KCN, CH$_2$Cl$_2$, H$_2$O; (g) 6N HCl/MeOH; (h) DAST, dry CH$_2$Cl$_2$, -30° C.; (i) i. LiAlH$_4$, dry Et$_2$O, -20° C., ii. (COCl)$_2$, dry Et$_3$N, dry DMSO, dry CH$_2$Cl$_2$, -65° C.; (j) thiazole, n-BuLi, dry Et$_2$O, -78° C.; (k) Dess-Martin periodinane, dry CH$_2$Cl$_2$.

The following target compounds of the invention are synthesised according to the protocols above:

2-(4-(Hexyloxy)phenyl)ethanol (31)

Procedure O $C_{14}H_{22}O_2$
MW: 222.32.
Colorless oil. Yield 97%.

$^1$H NMR (200 MHz, CDCl$_3$) δ=7.14 (d, 2H, J=8.6 Hz, CH, Ph), 6.85 (d, 2H, J=8.8 Hz, CH, Ph), 3.94 (t, 2H, J=6.4 Hz, CH$_2$OPh), 3.82 (t, 2H, J=5.2 Hz, CH$_2$OH), 2.81 (t, 2H,

J=6.4 Hz, PhCH$_2$), 1.81-1.71 (m, 2H, CH$_2$CH$_2$OPh), 1.50-1.26 (m, 6H, 3×CH$_2$), 0.91 (t, 3H, J=6.8 Hz, CH$_3$).

$^{13}$C NMR (50 MHz, CDCl$_3$) δ=157.8, 130.2, 129.8, 114.6, 68.0, 63.7, 38.2, 31.5, 29.2, 25.6, 22.5, 14.0.

2-(4-(Hexyloxy)phenyl)acetaldehyde (32)

Procedure G

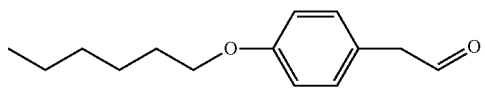 [SMILES: CCCCCCOc1ccc(CC=O)cc1]

C$_{14}$H$_{20}$O$_2$
MW: 220.31.
Yellow oil. Yield 97%.

$^1$H NMR (200 MHz, CDCl$_3$) δ=9.72 (t, 1H, J=2.4 Hz, CHO), 7.13 (d, 2H, J=8.4 Hz, CH, Ph), 6.90 (d, 2H, J=8.6 Hz, CH, Ph), 3.96 (t, 2H, J=6.4 Hz, CH$_2$OPh), 3.63 (d, 2H, J=2.4 Hz, PhCH$_2$), 1.92-1.74 (m, 2H, CH$_2$CH$_2$OPh), 1.54-1.27 (m, 6H, 3×CH$_2$), 0.92 (t, 3H, J=6.8 Hz, CH$_3$).

$^{13}$C NMR (50 MHz, CDCl$_3$) δ=199.4, 158.2, 130.3, 123.1, 114.7, 67.7, 49.4, 31.2, 28.9, 25.4, 22.3, 13.7.

(E)-Methyl 4-(4-(hexyloxy)phenyl)but-2-enoate (33)

Procedure R

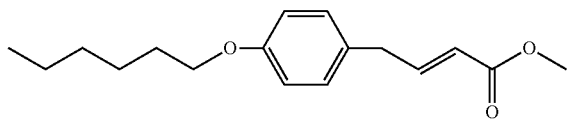 [SMILES: CCCCCCOc1ccc(C/C=C/C(=O)OC)cc1]

C$_{17}$H$_{24}$O$_3$
MW: 276.37.
Yellowish oil. Yield 86%.

$^1$H NMR (200 MHz, CDCl$_3$) δ=7.16-7.05 (m, 3H, CH$_2$CHCH, CH, Ph), 6.84 (d, 2H, J=8.0 Hz, CH, Ph), 5.79 (d, 1H, J=15.6 Hz, CHCOOMe), 3.94 (t, 2H, J=6.4 Hz, CH$_2$OPh), 3.72 (s, 3H, COOCH$_3$), 3.46 (d, 2H, J=6.4 Hz, PhCH$_2$), 1.83-1.64 (m, 2H, CH$_2$CH$_2$OPh), 1.45-1.23 (m, 6H, 3×CH$_2$), 0.91 (t, 3H, J=6.8 Hz, CH$_3$).

$^{13}$C NMR (50 MHz, CDCl$_3$) δ=166.9, 157.9, 148.1, 129.6, 129.3, 121.5, 114.6, 68.0, 51.4, 37.6, 31.5, 29.2, 25.7, 22.5, 14.0.

MS (ESI) m/z (%): 277 [M+H, 100]$^+$.

Methyl 4-(4-(hexyloxy)phenyl)butanoate (34)

Procedure S

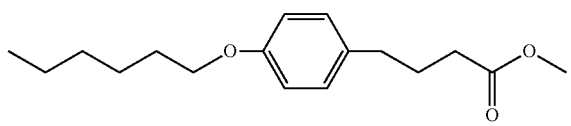 [SMILES: CCCCCCOc1ccc(CCCC(=O)OC)cc1]

C$_{17}$H$_{26}$O$_3$
MW: 278.39.
Colorless oil. Yield 91%.

$^1$H NMR (200 MHz, CDCl$_3$) δ=7.08 (d, 2H, J=8.6 Hz, CH, Ph), 6.83 (d, 2H, J=8.6 Hz, CH, Ph), 3.93 (t, 2H, J=6.6 Hz, CH$_2$OPh), 3.67 (s, 3H, COOCH$_3$), 2.60 (t, 2H, J=7.2 Hz, PhCH$_2$), 2.33 (t, 2H, J=7.2 Hz, CH$_2$COOMe), 2.05-1.89 (m, 2H, CH$_2$CH$_2$COOMe), 1.86-1.71 (m, 2H, CH$_2$CH$_2$OPh), 1.54-1.23 (m, 6H, 3×CH$_2$), 0.92 (t, 3H, J=6.6 Hz, CH$_3$).

$^{13}$C NMR (50 MHz, CDCl$_3$) δ=173.9, 157.4, 133.0, 129.2, 114.3, 67.9, 51.3, 34.1, 33.2, 31.5, 29.2, 26.6, 25.7, 22.5, 13.9.

4-(4-(Hexyloxy)phenyl)butanal (35)

Procedure N then G

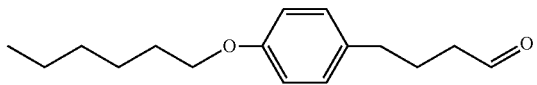 [SMILES: CCCCCCOc1ccc(CCCC=O)cc1]

C$_{16}$H$_{24}$O$_2$
MW: 248.36.
Yellow oil. Yield 99%.

$^1$H NMR (200 MHz, CDCl$_3$) δ=9.76 (t, 1H, J=1.6 Hz, CHO), 7.08 (d, 2H, J=8.6 Hz, CH, Ph), 6.83 (d, 2H, J=8.6 Hz, CH, Ph), 3.94 (t, 2H, J=6.6 Hz, CH$_2$OPh), 2.61 (t, 2H, J=7.4 Hz, PhCH$_2$), 2.49-2.37 (m, 2H, CH$_2$CHO), 2.06-1.90 (m, 2H, CH$_2$CH$_2$CHO), 1.86-1.71 (m, 2H, CH$_2$CH$_2$OPh), 1.49-1.27 (m, 6H, 3×CH$_2$), 0.91 (t, 3H, J=6.8 Hz, CH$_3$).

$^{13}$C NMR (50 MHz, CDCl$_3$) δ=202.4, 157.4, 133.0, 129.2, 114.4, 68.0, 43.1, 34.1, 31.6, 29.3, 25.7, 23.8, 22.6, 14.0.

5-(4-(Hexyloxy)phenyl)-2-hydroxypentanenitrile (36)

Procedure T

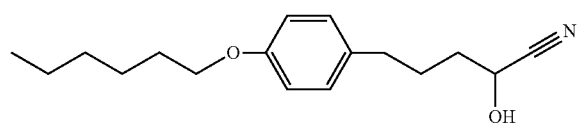 [SMILES: CCCCCCOc1ccc(CCCC(O)C#N)cc1]

C$_{17}$H$_{25}$NO$_2$
MW: 275.39.
Colorless oil. Yield 74%.

$^1$H NMR (200 MHz, CDCl$_3$) δ=7.08 (d, 2H, J=8.8 Hz, CH, Ph), 6.83 (d, 2H, J=8.8 Hz, CH, Ph), 4.43 (t, 1H, J=6.2 Hz, CHOH), 3.94 (t, 2H, J=6.6 Hz, CH$_2$OPh), 2.63 (t, 2H, J=6.4 Hz, PhCH$_2$), 2.28 (br s, 1H, OH), 1.93-1.61 (m, 6H, 3×CH$_2$), 1.53-1.23 (m, 6H, 3×CH$_2$), 0.91 (t, 3H, J=6.8 Hz, CH$_3$).

$^{13}$C NMR (50 MHz, CDCl$_3$) δ=157.4, 132.9, 129.2, 119.9, 114.5, 68.0, 61.0, 34.5, 34.0, 31.5, 29.2, 26.3, 25.7, 22.5, 14.0.

MS (ESI) m/z (%): 293 [M+H$_2$O, 100]$^+$.

Methyl 5-(4-(hexyloxy)phenyl)-2-hydroxypentanoate (37)

Procedure U

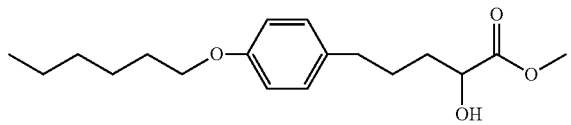 [SMILES: CCCCCCOc1ccc(CCCC(O)C(=O)OC)cc1]

C$_{18}$H$_{28}$O$_4$
MW: 308.41.
Colorless oil. Yield 86%.

$^1$H NMR (200 MHz, CDCl$_3$) δ=7.08 (d, 2H, J=8.6 Hz, CH, Ph), 6.81 (d, 2H, J=8.6 Hz, CH, Ph), 4.20 (t, 1H, J=6.8 Hz, CHOH), 3.93 (t, 2H, J=6.6 Hz, CH$_2$OPh), 3.78 (s, 3H, COOCH$_3$), 3.00 (br s, 1H, CHOH), 2.58 (t, 2H, J=6.6 Hz, PhCH$_2$), 1.86-1.55 (m, 6H, 3×CH$_2$), 1.52-1.17 (m, 6H, 3×CH$_2$), 0.91 (t, 3H, J=6.6 Hz, CH$_3$).

$^{13}$C NMR (50 MHz, CDCl$_3$) δ=175.5, 157.2, 133.7, 129.1, 114.3, 70.3, 67.9, 52.4, 34.5, 33.8, 31.5, 29.2, 26.7, 25.7, 22.5, 14.0.

MS (ESI) m/z (%): 309 [M+H, 100]$^+$.

Methyl 2-fluoro-5-(4-(hexyloxy)phenyl)pentanoate (38)

Procedure P

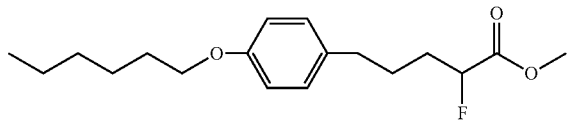

C$_{18}$H$_{27}$FO$_3$
MW: 310.40.
Colorless oil. Yield 37% (182 mg).

$^1$H NMR (200 MHz, CDCl$_3$) δ=7.08 (d, 2H, J=8.6 Hz, CH, Ph), 6.83 (d, 2H, J=8.8 Hz, CH, Ph), 4.93 (dt, 1H, J$_{H-H}$=5.8 Hz, J$_{H-F}$=50.2 Hz, CHF), 3.94 (t, 2H, J=6.6 Hz, CH$_2$OPh), 3.79 (s, 3H, COOCH$_3$), 2.61 (t, 2H, J=7.4 Hz, PhCH$_2$), 2.05-1.62 (m, 6H, 3×CH$_2$), 1.56-1.23 (m, 6H, 3×CH$_2$), 0.91 (t, 3H, J=6.6 Hz, CH$_3$).

$^{13}$C NMR (50 MHz, CDCl$_3$) δ=170.3 (d, J$_{C-C-F}$=23 Hz, COO), 157.4, 133.2, 129.2, 114.4, 88.8 (d, J$_{C-F}$=183 Hz, CF), 68.0, 52.3, 34.3, 32.0, 31.6, 29.3, 26.3, 25.7, 22.6, 14.0.

$^{19}$F NMR (186 MHz, CDCl$_3$) δ=−192.4 (m, CHF).

MS (ESI) m/z (%): 328 [M+H$_2$O, 100]$^+$, 311 [M+H, 15]$^+$.

2-Fluoro-5-(4-(hexyloxy)phenyl)pentanal (39)

Procedure N then Q

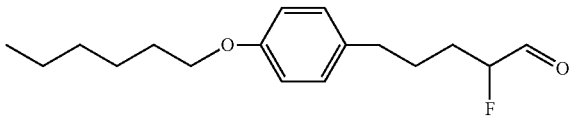 [SMILES: CCCCCCOc1ccc(CCCC(F)C=O)cc1]

C$_{17}$H$_{25}$FO$_2$
MW: 280.38.
Yellow oil. Yield 50%.

$^1$H NMR (200 MHz, CDCl$_3$) δ=9.74 (d, 1H, J=6.2 Hz, CHO), 7.08 (d, 2H, J=8.4 Hz, CH, Ph), 6.84 (d, 2H, J=8.4 Hz, CH, Ph), 4.76 (dm, 1H, J$_{H-F}$=51.4 Hz, CHF), 3.94 (t, 2H, J=6.6 Hz, CH$_2$OPh), 2.62 (t, 2H, J=7.2 Hz, PhCH$_2$), 1.93-1.72 (m, 6H, 3×CH$_2$), 1.54-1.24 (m, 6H, 3×CH$_2$), 0.93 (t, 3H, J=6.6 Hz, CH$_3$).

$^{13}$C NMR (50 MHz, CDCl$_3$) δ=200.0 (d, J$_{C-C-F}$=34 Hz, CHO), 157.4, 133.0, 129.2, 114.4, 94.8 (d, J$_{C-F}$=178 Hz, CF), 67.9, 34.3, 31.5, 29.6 (d, J$_{C-C-F}$=20 Hz, CH$_2$CHF), 29.2, 26.1, 25.7, 22.6, 14.0.

$^{19}$F NMR (186 MHz, CDCl$_3$) δ=−199.8 (m, CHF).

2-Fluoro-5-(4-(hexyloxy)phenyl)-1-(thiazol-2-yl)pentan-1-ol (40)

Procedure A

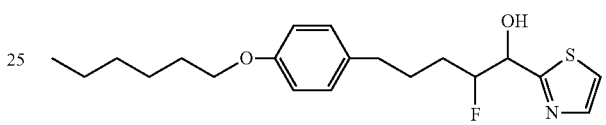

C$_{20}$H$_{28}$FNO$_2$S
MW: 365.51.
Yellow oil. Yield 38%.

$^1$H NMR (200 MHz, CDCl$_3$) δ=7.90 (d, 1/7H, J=3.2 Hz, ArH), 7.83 (d, 6/7H, J=3.2 Hz, ArH), 7.45 (d, 1/7H, J=3.2 Hz, ArH), 7.35 (d, 6/7H, J=3.2 Hz, ArH), 7.05 (d, 2H, J=8.6 Hz, CH, Ph), 6.80 (d, 2H, J=8.6 Hz, CH, Ph), 5.15 (dd, 1H, J$_{H-H}$=4.6 Hz, J$_{H-F}$=12.8 Hz, CHOH), 4.99-4.65 (dm, 1H, J$_{H-F}$=48.2 Hz, CHF), 3.93 (t, 2H, J=6.4 Hz, CH$_2$OPh), 2.56 (t, 2H, J=7.2 Hz, PhCH$_2$), 1.88-1.27 (m, 12H, 6×CH$_2$), 0.91 (t, 3H, J=6.8 Hz, CH$_3$).

$^{13}$C NMR (50 MHz, CDCl$_3$) δ=170.2, 157.2, 142.1, 133.7, 129.1, 119.7, 114.3, 95.1 (d, J$_{C-F}$=174 Hz, CF), 73.0 (d, 1/3C, J$_{C-C-F}$=21 Hz, COH), 72.9 (d, 2/3C, J$_{C-C-F}$=24 Hz, COH), 67.9, 34.5, 31.5, 30.4 (d, J$_{C-C-F}$=20 Hz, CH$_2$), 29.2, 26.9, 25.7, 22.5, 14.0.

$^{19}$F NMR (186 MHz, CDCl$_3$) δ=−190.0 (m, CHF), −194.4 (m, CHF).

MS (ESI) m/z (%): 366 [M+H, 100]$^+$.

2-Fluoro-5-(4-(hexyloxy)phenyl)-1-(thiazol-2-yl)pentan-1-one (41)

Procedure B

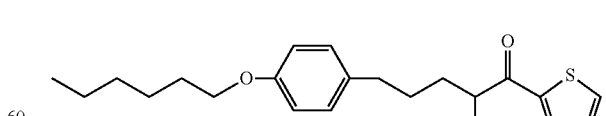

C$_{20}$H$_{26}$FNO$_2$S
MW: 363.49.
Colorless oil. Yield 60%.

$^1$H NMR (200 MHz, CDCl$_3$) δ=8.04 (d, 1H, J=2.8 Hz, ArH), 7.75 (d, 1H, J=3.0 Hz, ArH), 7.07 (d, 2H, J=8.4 Hz,

CH, Ph), 6.80 (d, 2H, J=8.6 Hz, CH, Ph), 5.98 (ddd, 1H, $J_{H\text{-}F}$=49.6 Hz, $J_{H\text{-}H}$=7.6 Hz, $J_{H\text{-}H}$=3.6 Hz, CHF), 3.92 (t, 2H, J=6.6 Hz, CH$_2$OPh), 2.75-2.52 (m, 2H, PhCH$_2$), 2.30-1.70 (m, 6H, 3×CH$_2$), 1.59-1.26 (m, 6H, 3×CH$_2$), 0.91 (t, 3H, J=6.6 Hz, CH$_3$).

$^{13}$C NMR (50 MHz, CDCl$_3$) δ=188.9 (d, $J_{C\text{-}C\text{-}F}$=19 Hz, CO), 163.8, 157.4, 145.1, 133.3, 129.2, 126.9, 114.4, 92.3 (d, $J_{C\text{-}F}$=182 Hz, CF), 68.0, 34.3, 32.0 (d, $J_{C\text{-}C\text{-}F}$=21 Hz, CH$_2$CHF), 31.6, 29.3, 26.6, 25.7, 22.6, 14.0.

$^{19}$F NMR (186 MHz, CDCl$_3$) δ=-196.2 (m, CHF).

MS (ESI) m/z (%): 364 [M+H, 100]$^+$.

The following new target compounds are therefore synthesised

TABLE 1

2-Oxo-thiazoles.

| Number | Corres No. | Structure | MW | ClogP |
|---|---|---|---|---|
| GK146 | 3a | 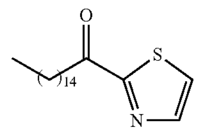 | 323.54 | 8.1 |
| GK147 | 3b | 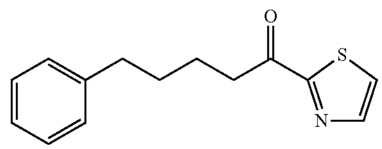 [SMILES: O=C(CCCCc1ccccc1)c1nccs1] | 245.34 | 3.7 |
| GK149 | 3d | 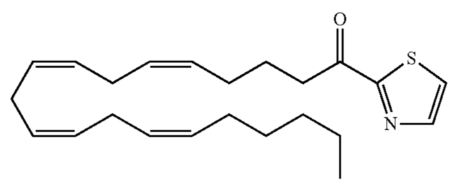 [SMILES: CCCCC/C=C\C/C=C\C/C=C\C/C=C\CCCC(=O)c1nccs1] | 371.58 | 8.3 |
| GK150 | 9 | 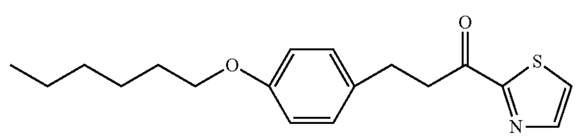 [SMILES: CCCCCCOc1ccc(CCC(=O)c2nccs2)cc1] | 317.45 | 5.4 |
| GK151 | 15a | 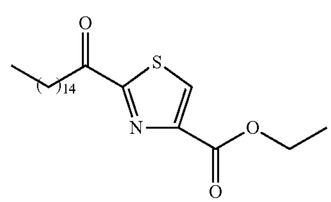 | 395.60 | 8.3 |
| GK152 | 15b | 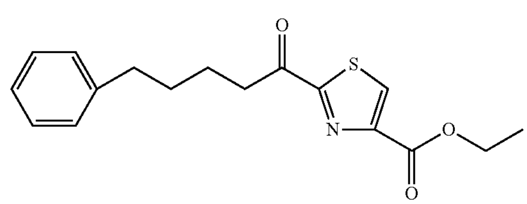 [SMILES: CCOC(=O)c1csc(C(=O)CCCCc2ccccc2)n1] | 317.40 | 3.8 |
| GK153 | 19 | 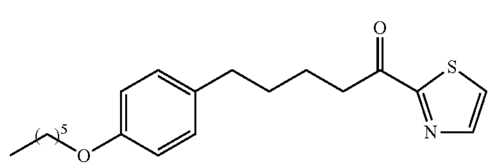 | 345.50 | 6.3 |
| GK154 | 24 | 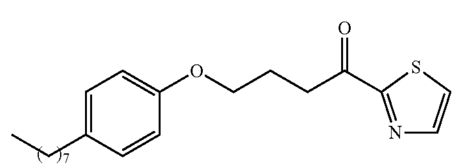 | 359.53 | 7.1 |

TABLE 1-continued
2-Oxo-thiazoles.
| Number | Corres No. | Structure | MW | ClogP |
|---|---|---|---|---|
| GK155 | 29 | 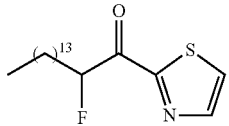 | 341.53 | 7.8 |
| GK156 | 41 | 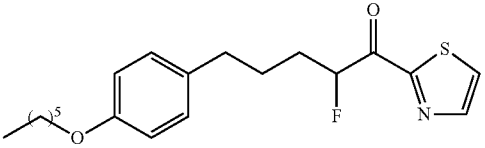 | 363.49 | 6.0 |
A series of further compounds have been synthesised based on the principles outlined above. These are listed in table 2
TABLE 2
GK148 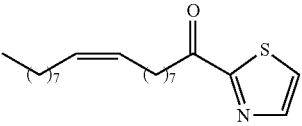
GK157 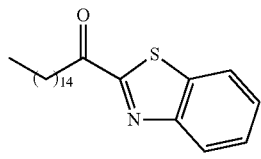
GK158 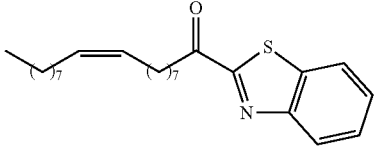
GK159 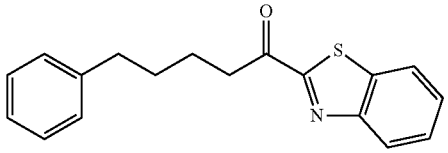 [SMILES: O=C(CCCCc1ccccc1)c1nc2ccccc2s1]
GK160 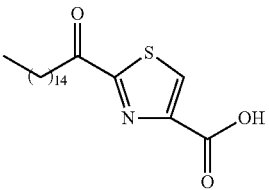
GK162 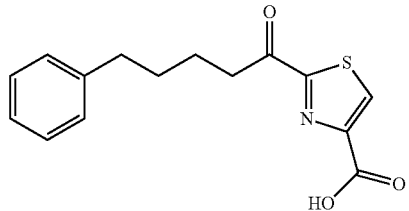 [SMILES: O=C(O)c1csc(C(=O)CCCCc2ccccc2)n1]

TABLE 2-continued
GK179 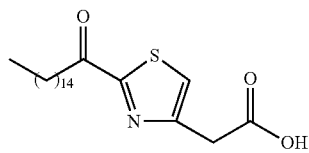
GK180 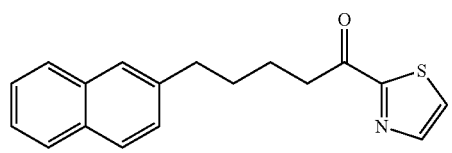 [SMILES: O=C(CCCCc1ccc2ccccc2c1)c1nccs1]
GK181 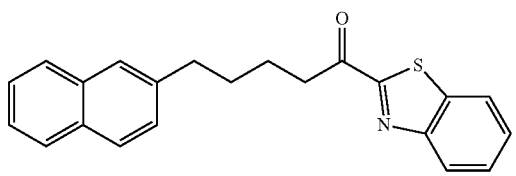
GK182 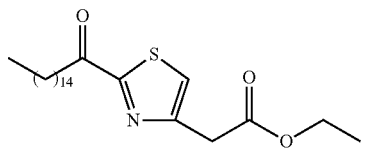
GK183 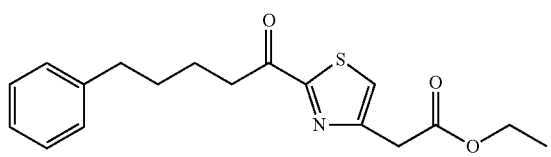 [SMILES: CCOC(=O)Cc1csc(C(=O)CCCCc2ccccc2)n1]
GK184 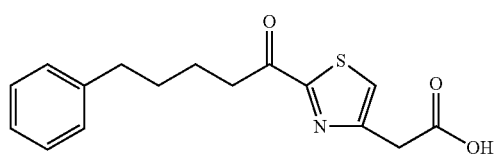 [SMILES: O=C(O)Cc1csc(C(=O)CCCCc2ccccc2)n1]
GK198 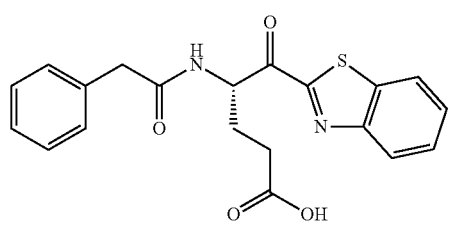 [SMILES: O=C(O)CC[C@H](NC(=O)Cc1ccccc1)C(=O)c1nc2ccccc2s1]
GK199 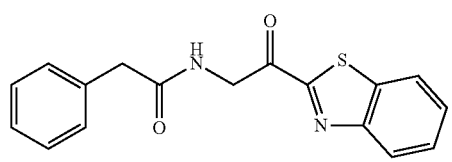 [SMILES: O=C(Cc1ccccc1)NCC(=O)c1nc2ccccc2s1]
GK201 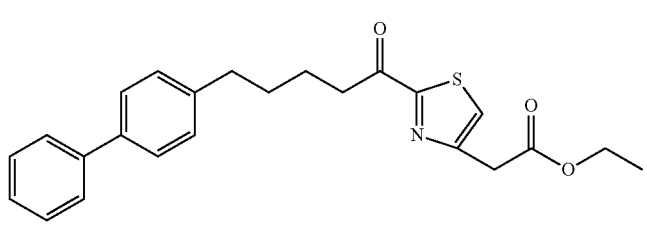 [SMILES: CCOC(=O)Cc1csc(C(=O)CCCCc2ccc(-c3ccccc3)cc2)n1]

TABLE 2-continued
GK202
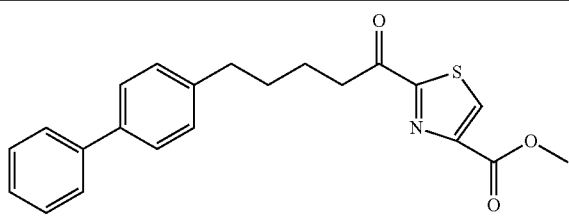
GK203
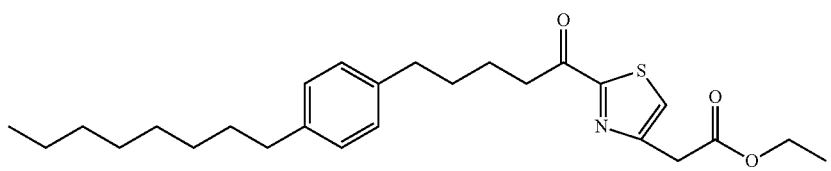 [SMILES: CCCCCCCCc1ccc(CCCCC(=O)c2nc(CC(=O)OCC)cs2)cc1]
GK204
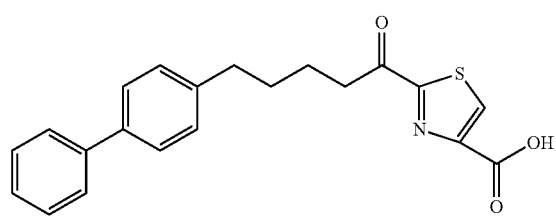 [SMILES: O=C(O)c1csc(C(=O)CCCCc2ccc(-c3ccccc3)cc2)n1]
Synthetic Schemes
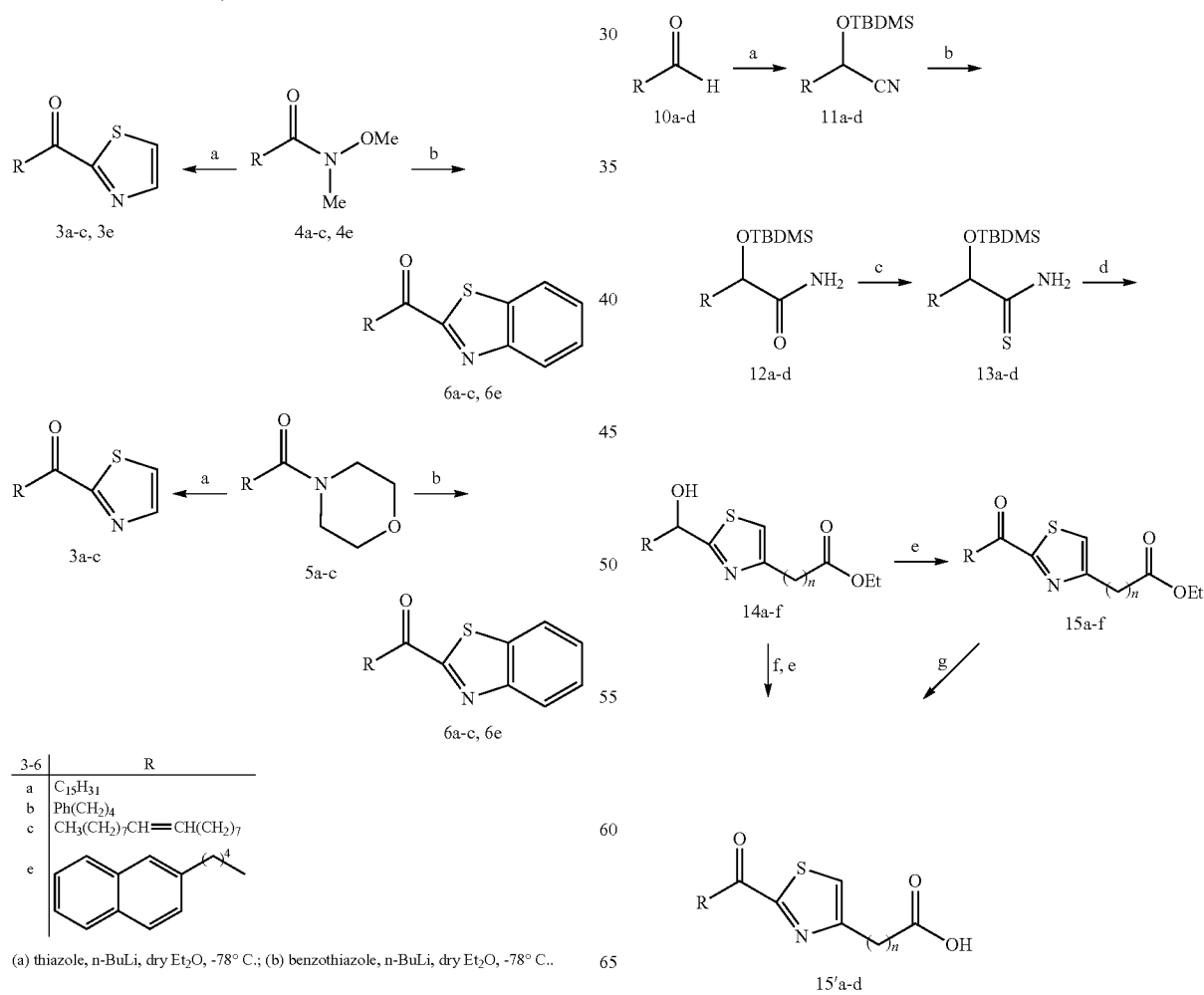
| 3-6 | R |
|---|---|
| a | $C_{15}H_{31}$ |
| b | $Ph(CH_2)_4$ |
| c | $CH_3(CH_2)_7CH=CH(CH_2)_7$ |
| e | 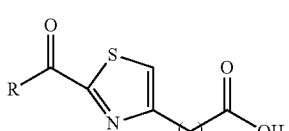 |
(a) thiazole, n-BuLi, dry Et$_2$O, -78° C.; (b) benzothiazole, n-BuLi, dry Et$_2$O, -78° C..

51
-continued

| 10-14 | R |
|---|---|
| a | C₁₅H₃₁ |
| b | Ph(CH₂)₄ |
| c | 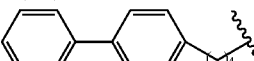 |
| d | 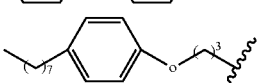 |

| 14-15 | R | n |
|---|---|---|
| a | C₁₅H₃₁ | 0 |
| b | Ph(CH₂)₄ | 0 |
| c | C₁₅H₃₁ | 1 |
| d | Ph(CH₂)₄ | 1 |
| e | 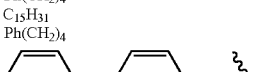 | 1 |
| f | 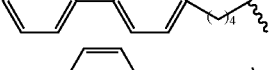 | 1 |

(a) TBDMSCN, KCN, 18-crown-6, CH₂Cl₂; (b) 30% H₂O₂, Bu₄NHSO₄, NaOH, CH₂Cl₂; (c) Lawesson's reagent, THF; (d) Br(CH₂)ₙCOCOOEt, conc. H₂SO₄, EtOH, 40° C.; (e) Dess Martin periodinane, dry CH₂Cl₂; (f) 1N NaOH, EtOH; (g) Cs₂CO₃, EtOH.

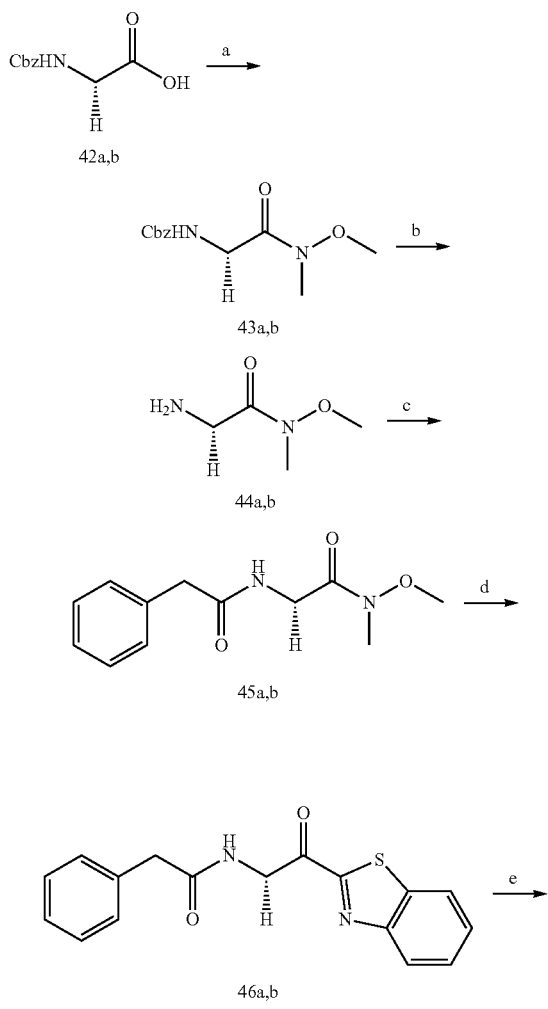

52
-continued

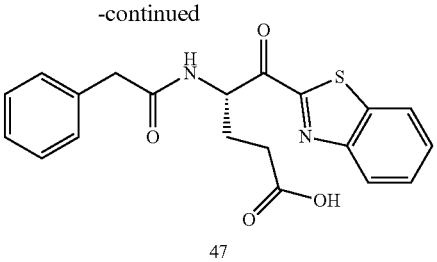

47

| 42-46 | R |
|---|---|
| a | H |
| b | (CH₂)₂COOᵗBu |

(a) N,O-dimethyl hydroxylamine hydrochloride, DMAP, N-methyl morpholine, WSCI.HCl, CH₂Cl₂; (b) ammonium formate; 10% Pd/C, MeOH; (c) PhCH₂COOH, Et₃N, WSCI, HOBt, CH₂Cl₂; (d) benzothiazole, n-BuLi, dry Et₂O, -78° C.; (e) 50% TFA/CH₂Cl₂.

Characterization Data

The following target compounds of the invention are synthesised according to the protocols above:

N-methoxy-N-methyloleamide (4c)

Prepared by Procedure C

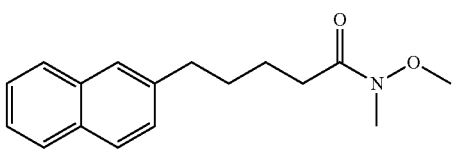 [SMILES: CON(C)C(=O)CCCCc1ccc2ccccc2c1]

$C_{20}H_{39}NO_2$
MW: 325.53
Colorless oil. Yield 86% (985 mg).
$^1H$ NMR (200 MHz, CDCl₃) δ=5.34-5.29 (m, 2H, CH=CH), 3.65 (s, 3H, OMe), 3.15 (s, 3H, NMe), 2.38 (t, 2H, J=7.4 Hz, CH₂CO), 1.99 (m, 4H, CH₂CH=CHCH₂), 1.60 (m, 2H, CH₂CH₂CO), 1.29-1.24 (m, 20H, 10×CH₂), 0.85 (t, 3H, J=5.2 Hz, CH₃).
$^{13}C$ NMR (50 MHz, CDCl₃) δ=174.5, 129.8, 129.6, 61.0, 31.8, 29.6, 29.6, 29.4, 29.3, 29.2, 27.0, 25.5, 24.5, 22.5, 14.0.

N-methoxy-N-methyl-5-(naphthalen-2-yl)pentanamide (4e)

Prepared by Procedure C $C_{17}H_{21}NO_2$
MW: 271.35
Colorless oil. Yield 75% (310 mg).
$^1H$ NMR (CDCl₃): δ=7.90-7.30 (m, 7H, ArH), 3.65 (s, 3H, OMe), 3.18 (s, 3H, NMe), 2.82 (t, 2H, J=7.2 Hz, CH₂), 2.47 (t, 2H, J=7.0 Hz, CH₂), 1.98-1.60 (m, 4H, 2×CH₂).
MS (ESI) m/z (%): 272 [M+H, 100]⁺.

(Z)-1-morpholinooctadec-9-en-1-one (5c)

Prepared by Procedure D $C_{22}H_{41}NO_2$
MW: 351.57

Colorless oil. Yield 98% (1.59 g).

$^1$H NMR (200 MHz, CDCl$_3$) δ=5.31-5.25 (m, 2H, CH=CH), 3.62-3.57 (m, 6H, CH$_2$OCH$_2$, CHHNCHH), 3.40 (t, 2H, J=5.0 Hz, CHHNCHH), 2.25 (t, 2H, J=7.4 Hz, CH$_2$CO), 1.97-1.93 (m, 4H, CH$_2$CH=CHCH$_2$), 1.60-1.53 (m, 2H, CH$_2$CH$_2$CO), 1.26-1.21 (m, 20H, 10×CH$_2$), 0.82 (t, 3H, J=6.2 Hz, CH$_3$).

$^{13}$C NMR (50 MHz, CDCl$_3$) δ=171.6, 129.8, 129.5, 66.8, 66.5, 45.8, 41.7, 32.9, 31.7, 29.6, 29.5, 29.3, 29.2, 29.1, 28.9, 27.0, 25.0, 22.5, 13.9.

(Z)-1-(Thiazol-2-yl)octadec-9-en-1-one (3c)

Prepared by Procedure E

Yield when the Weinreb amide was used: 70%

Yield when the morpholine amide was used: 70%

5-(Naphthalen-2-yl)-1-(thiazol-2-yl)pentan-1-one (3e)

Prepared by Procedure E $C_{18}H_{17}NOS$
MW: 295.40

Yellow solid. Yield 70%

$^1$H NMR (200 MHz, CDCl$_3$) δ=7.97 (d, 1H, J=3.0 Hz, ArH), 7.80-7.75 (m, 3H, ArH), 7.75-7.63 (m, 2H, ArH), 7.50-7.30 (m, 3H, ArH), 3.21 (t, 2H, J=7.0 Hz, CH$_2$), 2.83 (t, 2H, J=6.8 Hz, CH$_2$), 1.98-1.80 (m, 4H, 2×CH$_2$).

$^{13}$C NMR (50 MHz, CDCl$_3$) δ=193.8, 167.1, 144.6, 139.6, 133.5, 131.9, 127.8, 127.5, 127.4, 127.3, 126.3, 126.1, 125.8, 125.0, 38.2, 35.7, 30.8, 23.6.

MS (ESI) m/z (%): 296 [M+H, 100]$^+$.

1-(Benzo[d]thiazol-2-yl)hexadecan-1-one (6a)

Prepared by Procedure E $C_{23}H_{35}NOS$
MW: 373.60

Yellowish solid.

Yield via Weinreb amide 60% (140 mg).

Yield via morpholine amide 85% (180 mg).

m.p.: 74-76° C.

$^1$H NMR (200 MHz, CDCl$_3$) δ=8.19 (d, 1H, J=7.4 Hz, benzothiazole), 7.98 (d, 1H, J=7.4 Hz, benzothiazole), 7.62-7.49 (m, 2H, benzothiazole), 3.27 (t, 2H, J=7.2 Hz, CH$_2$CO), 1.86-1.74 (m, 2H, CH$_2$CH$_2$CO), 1.44-1.21 (m, 24H, 12×CH$_2$), 0.88 (t, 3H, J=6.0 Hz, CH$_3$).

$^{13}$C NMR (50 MHz, CDCl$_3$) δ=195.6, 166.6, 153.5, 137.2, 127.5, 126.8, 125.3, 122.4, 38.5, 31.9, 29.6, 29.6, 29.4, 29.3, 29.3, 29.1, 23.9, 22.6, 14.1.

MS (ESI) m/z (%): 374 [M+H, 100]$^+$.

1-(Benzo[d]thiazol-2-yl)-5-phenylpentan-1-one (6b)

Prepared by Procedure E $C_{18}H_{17}NOS$
MW: 295.40

Yellow solid.

Yield via Weinreb amide 77% (204 mg).

Yield via morpholine amide 72% (126 mg).

m.p.: 66-68° C.

$^1$H NMR (200 MHz, CDCl$_3$) δ=8.19 (d, 1H, J=7.4 Hz, benzothiazole), 7.96 (d, 1H, J=7.6 Hz, benzothiazole), 7.61-7.47 (m, 2H, benzothiazole), 7.34-7.15 (m, 5H, Ph), 3.31 (t, 2H, J=6.8 Hz, CH$_2$CO), 2.70 (t, 2H, J=7.4 Hz, PhCH$_2$), 1.96-1.69 (m, 4H, 2×CH$_2$).

$^{13}$C NMR (50 MHz, CDCl$_3$) δ=195.2, 166.3, 153.4, 142.0, 137.1, 128.3, 128.2, 127.5, 126.8, 125.6, 125.2, 122.3, 38.2, 35.5, 30.8, 23.4.

MS (ESI) m/z (%): 296 [M+H, 100]$^+$.

(Z)-1-(Benzo[d]thiazol-2-yl)octadec-9-en-1-one (6c)

Prepared by Procedure E

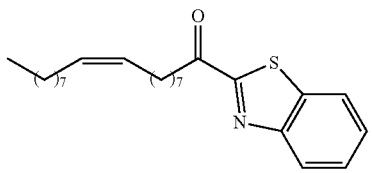

$C_{25}H_{37}NOS$
MW: 399.63
Yellow oil.
Yield via Weinreb amide 70% (170 mg).
$^1$H NMR (200 MHz, CDCl$_3$) δ=8.17 (d, 1H, J=7.0 Hz, benzothiazole), 7.95 (d, 1H, J=6.2 Hz, benzothiazole), 7.60-7.45 (m, 2H, benzothiazole), 5.42-5.27 (m, 2H, CH=CH), 3.26 (t, 2H, J=7.4 Hz, CH$_2$CO), 2.02-2.00 (m, 4H, CH$_2$CH=CHCH$_2$), 1.88-1.73 (m, 2H, CH$_2$CH$_2$CO), 1.43-1.25 (m, 20H, 10×CH$_2$), 0.87 (t, 3H, J=6.4 Hz, CH$_3$).
$^{13}$C NMR (50 MHz, CDCl$_3$) δ=195.4, 166.5, 153.4, 137.1, 129.9, 129.6, 127.4, 126.8, 125.2, 122.3, 38.5, 31.8, 29.7, 29.6, 29.4, 29.2, 29.2, 29.1, 29.0, 27.1, 27.1, 23.8, 22.6, 14.0.
MS (ESI) m/z (%): 400 [M+H, 100]$^+$.

1-(Benzo[d]thiazol-2-yl)-5-(naphthalen-2-yl)pentan-1-one (6e)

Prepared by Procedure E

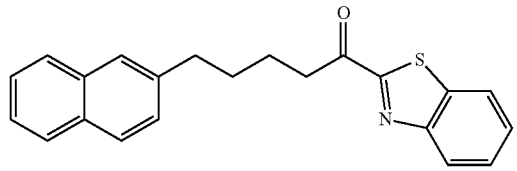 [SMILES: O=C(CCCCc1ccc2ccccc2c1)c1nc2ccccc2s1]

$C_{22}H_{19}NOS$
MW: 345.46
Yellow solid. Yield 72%.
$^1$H NMR (200 MHz, CDCl$_3$) δ=8.20 (d, 1H, J=6.0 Hz, ArH), 7.97 (d, 1H, J=8.0 Hz, ArH), 7.90-7.70 (m, 3H, ArH), 7.70-7.30 (m, 6H, ArH), 3.35 (t, 2H, J=7.0 Hz, CH$_2$), 2.90 (t, 2H, J=6.8 Hz, CH$_2$), 2.05-1.82 (m, 4H, 2×CH$_2$).
$^{13}$C NMR (50 MHz, CDCl$_3$) δ=195.3, 166.4, 153.5, 139.6, 137.2, 133.5, 131.9, 127.8, 127.6, 127.5, 127.4, 127.3, 126.9, 126.4, 125.8, 125.3, 125.0, 122.4, 38.3, 35.8, 30.7, 23.6.
MS (ESI) m/z (%): 246 [M+H, 100]$^+$.

Ethyl 2-(2-(1-hydroxyhexadecyl)thiazol-4-yl)acetate (14c)

Prepared by Procedure K

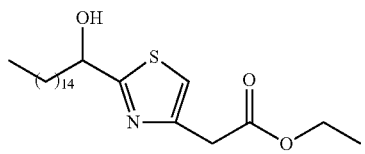

$C_{23}H_{41}NO_3S$
MW: 411.64
White solid.
$^1$H NMR (300 MHz, CDCl$_3$): δ=7.15 (s, 1H, SCH), 4.97 (dd, J$_1$=7.8 Hz, J$_2$=4.5 Hz, 1H, CHOH), 4.20 (q, J=7.2 Hz, 2H, COOCH$_2$), 3.82 (s, 2H, CH$_2$COO), 2.07-1.78 (m, 2H CH$_2$), 1.59-1.20 (m, 29H, 13×CH$_2$, CH$_3$), 0.89 (t, J=6.3 Hz, 3H, CH$_3$).
$^{13}$C NMR (50 MHz, CDCl$_3$): δ=174.98, 170.36, 148.18, 115.97, 71.95, 61.08, 38.32, 36.93, 31.91, 29.68, 29.66, 29.56, 29.49, 29.36, 25.20, 22.69, 14.14.
MS (ESI) m/z (%): 412 [M+H, 100]$^+$.

Ethyl 2-(2-(1-hydroxy-5-phenylpentyl)thiazol-4-yl)acetate (14d)

Prepared by Procedure K

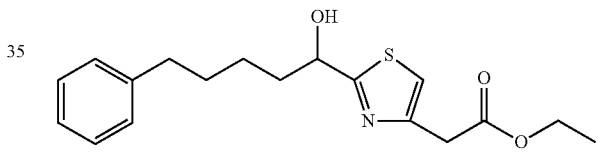

$C_{18}H_{23}NO_3S$
MW: 333.45
Pale yellow solid; Yield 44%.
m.p. 53-55° C.
$^1$H NMR (200 MHz, CDCl$_3$): δ 7.35-7.07 (m, 6H, SCH, Ph), 4.93 (dd, J$_1$=7.8 Hz, J$_2$=4.8 Hz, 1H, CHOH), 4.18 (q, J=7.0 Hz, COOCH$_2$), 3.79 (s, 2H, CH$_2$COO), 2.61 (t, J=7.2 Hz, CH$_2$Ph), 2.06-1.37 (m, 6H, 3×CH$_2$), 1.26 (t, J=7.2 Hz, 3H, CH$_3$).
$^{13}$C NMR (50 MHz, CDCl$_3$) δ 174.95, 170.37, 148.20, 142.38, 128.34, 128.24, 125.65, 116.00, 71.80, 61.08, 38.12, 36.90, 35.74, 31.19, 24.89, 14.15.
MS (ESI) m/z (%): 334 [M+H, 100]$^+$.

Ethyl 2-(2-palmitoylthiazol-4-yl)acetate (15c)

Prepared by Procedure B

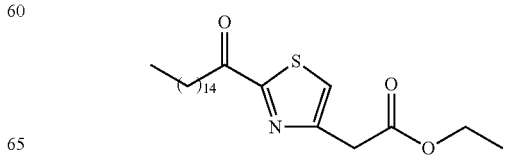

C_{23}H_{39}NO_3S
MW: 409.63
White solid. Yield 90%.
m.p. 46-48° C.
$^1$H NMR (300 MHz, CDCl$_3$): δ=7.54 (s, 1H, SCH), 4.21 (q, J=7.2 Hz, 2H, COOCH$_2$)), 3.90 (s, 2H, CH$_2$COO), 3.12 (t, J=7.5 Hz, 2H, CH$_2$CO), 1.82-1.62 (m, 2H CH$_2$), 1.55-1.19 (m, 27H, 12×CH$_2$, CH$_3$), 0.88 (t, J=7.0 Hz, 3H, CH$_3$).
$^{13}$C NMR (50 MHz, CDCl$_3$): δ=194.09, 170.00, 166.52, 150.95, 123.56, 61.24, 38.43, 37.00, 31.91, 29.65, 29.47, 29.39, 29.35, 29.18, 23.91, 22.68, 14.13.
MS (ESI) m/z (%): 410 [M+H, 100]$^+$.

Ethyl 2-(2-(5-phenylpentanoyl)thiazol-4-yl)acetate (15d)

Prepared by Procedure B

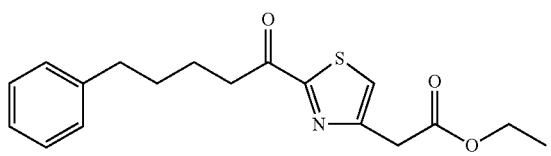 [SMILES: CCOC(=O)Cc1csc(C(=O)CCCCc2ccccc2)n1]

C_{18}H_{21}NO_3S
MW: 331.43
White oil. Yield 81%.
$^1$H NMR (300 MHz, CDCl$_3$): δ=7.55 (s, 1H, SCH), 7.34-7.16 (m, 5H, Ph), 4.22 (q, J=7.2 Hz, 2H, COOCH$_2$), 3.91 (s, 2H, CH$_2$COO), 3.17 (t, J=7.5 Hz, 2H, CH$_2$CO), 2.68 (t, J=7.2 Hz, 2H, CH$_2$Ph), 1.85-1.63 (m, 4H, 2×CH$_2$), 1.30 (t, J=7.2 Hz, 3H, CH$_3$).
$^{13}$C NMR (50 MHz, CDCl$_3$): δ=193.82, 169.99, 166.42, 150.99, 142.17, 128.39, 128.27, 125.71, 123.69, 61.26, 38.17, 36.99, 35.65, 30.92, 23.56, 14.16.
MS (ESI) m/z (%): 332 [M+H, 99]$^+$.

Ethyl 2-(2-(5-(biphenyl-4-yl)pentanoyl)thiazol-4-yl)acetate (15e)

Prepared by Procedure B

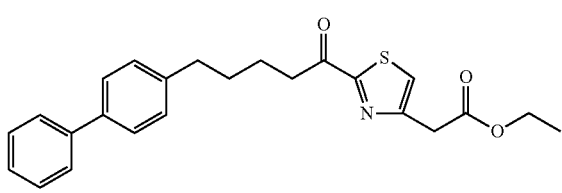 [SMILES: CCOC(=O)Cc1csc(C(=O)CCCCc2ccc(-c3ccccc3)cc2)n1]

C_{24}H_{25}NO_3S
MW: 407.53
White solid.
$^1$H NMR (200 MHz, CDCl$_3$): δ=7.65-7.18 (m, 10H, Ar, SCH), 4.21 (q, J=7.4 Hz, 2H, COOCH$_2$), 3.90 (s, 2H, CH$_2$COO), 3.18 (t, J=6.6 Hz, CH$_2$CO), 2.70 (t, J=7.2 Hz, CH$_2$Ph), 1.94-1.65 (m, 4H, 2×CH$_2$), 1.28 (t, J=7.2 Hz, CH$_3$).
$^{13}$C NMR (50 MHz, CDCl$_3$): δ=193.79, 169.95, 166.40, 151.01, 141.29, 141.06, 138.66, 128.80, 128.66, 127.01, 126.95, 123.67, 61.22, 38.15, 36.97, 35.25, 30.85, 23.57, 14.14.
MS (ESI) m/z (%): 408 [M+H, 100]$^+$.

2-palmitoylthiazole-4-carboxylic acid (15' a)

Prepared by Procedures L, then B

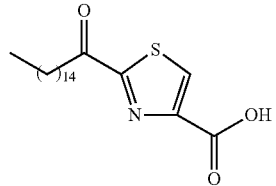

C_{20}H_{33}NO_3S
MW: 367.55
White solid. Yield 50%.
m.p. 98-100° C.
$^1$H NMR (200 MHz, CDCl$_3$): δ=8.39 (s, 1H, CH), 3.25-3.00 (m, 2H, CH$_2$), 1.80-1.55 (m, 2H, CH$_2$), 1.40-1.00 (m, 24H, 12×CH$_2$), 0.88 (t, 3H, J=6.8 Hz, CH$_3$).
$^{13}$C NMR (50 MHz, CDCl$_3$+CD$_3$OD): δ=193.9, 166.4, 164.6, 151.5, 131.8, 37.9, 31.5, 29.2, 29.0, 28.9, 28.7, 23.2, 22.2, 13.4.
MS (ESI) m/z (%): 366 [M−H, 100]−.

2-(5-Phenylpentanoyl)thiazole-4-carboxylic acid (15'b)

Prepared by Procedure M

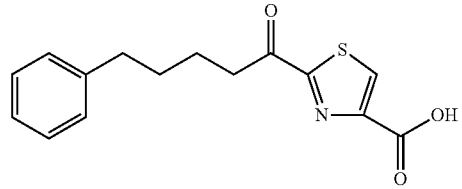 [SMILES: O=C(O)c1csc(C(=O)CCCCc2ccccc2)n1]

C_{15}H_{15}NO_3S
MW: 289.35
White solid. Yield 86% (25 mg).
$^1$H NMR (CDCl$_3$): δ=8.55 (s, 2H, ArH, COOH), 7.30-7.10 (m, 5H, Ph), 3.26 (t, 2H, J=6.8 Hz, CH$_2$), 2.66 (t, 2H, J=7.0 Hz, CH$_2$), 1.90-1.63 (m, 4H, 2×CH$_2$).
$^{13}$C NMR (CDCl$_3$): δ=193.5, 167.8, 164.6, 147.4, 142.0, 134.9, 128.4, 128.3, 125.8, 38.2, 35.6, 30.7, 23.2.
MS (ESI) m/z (%): 290 [M+H, 47]$^+$.

2-(2-Palmitoylthiazol-4-yl)acetic acid (15'c)

Prepared by Procedures L, then B

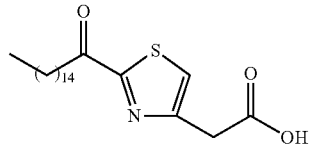

C$_{21}$H$_{35}$NO$_3$S
MW: 381.57
White solid.
$^1$H NMR (300 MHz, CDCl$_3$): δ 7.55 (s, 1H, SCH), 3.98 (s, 2H, CH$_2$COO), 3.13 (t, J=7.6 Hz, 2H, CH$_2$CO), 1.82-1.69 (m, 2H, CH$_2$), 1.43-1.18 (m, 24H, 12×CH$_2$), 0.89 (t, J=6.9 Hz, 3H, CH$_3$).
MS (ESI) m/z (%): 336 [M-COOH—H, 100]$^-$, 380 [M−H, 46]$^-$.

2-(2-(5-Phenylpentanoyl)thiazol-4-yl)acetic acid (15' d)

Prepared by Procedure M

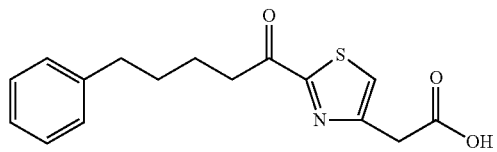 [SMILES: O=C(O)Cc1csc(C(=O)CCCCc2ccccc2)n1]

C$_{16}$H$_{17}$NO$_3$S
MW: 303.38
White oil. Yield 89%.
$^1$H NMR (300 MHz, CDCl$_3$): δ 7.49 (s, 1H, SCH), 7.35-7.08 (m, 5H, Ph), 3.88 (s, 2H, CH$_2$COO), 3.11 (t, J=7.5 Hz, 2H, CH$_2$CO), 2.63 (t, J=7.0 Hz, 2H, CH$_2$Ph), 1.85-1.63 (m, 4H, 2×CH$_2$).
MS (ESI) m/z (%): 304 [M+H, 77]$^+$.

(S)-tert-Butyl 4-(benzyloxycarbonylamino)-5-(methoxy(methyl)amino)-5-oxopentanoate (43b)

Prepared by Procedure C

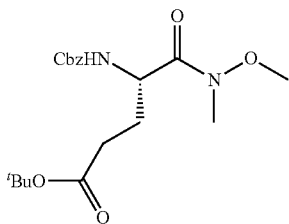 [SMILES: CON(C)C(=O)[C@H](CCC(=O)OC(C)(C)C)NC(=O)OCc1ccccc1]

C$_{19}$H$_{28}$N$_2$O$_6$
MW: 380.44
Colorless oil. Yield 100%.
$^1$H NMR (200 MHz, CDCl$_3$) δ=7.35-7.20 (m, 5H, ArH), 5.67 (d, 1H, J=8.0 Hz, NH), 5.06 (s, 2H, CH$_2$), 4.80-4.60 (m, 1H, CH), 3.73 (s, 3H, OMe), 3.15 (s, 3H, NMe), 2.40-1.70 (m, 4H, CH$_2$), 1.38 (s, 9H, $^t$Bu).
$^{13}$C NMR (50 MHz, CDCl$_3$) δ=171.9, 155.9, 136.1, 128.3, 127.9, 127.8, 80.3, 66.6, 61.4, 50.3, 31.9, 31.0, 27.9, 27.4.
MS (ESI) m/z (%): 381 [M+H, 100]$^+$.

(S)-tert-Butyl 5-(methoxy(methyl)amino)-5-oxo-4-(2-phenylacetamido)pentanoate (45b)

Prepared by Procedures V, then W

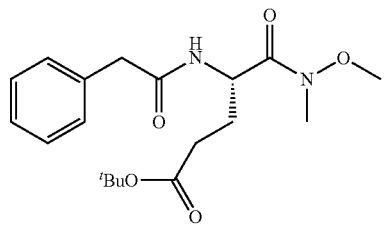 [SMILES: CON(C)C(=O)[C@H](CCC(=O)OC(C)(C)C)NC(=O)Cc1ccccc1]

C$_{19}$H$_{28}$N$_2$O$_5$
MW: 364.44
Colorless oil.
$^1$H NMR (200 MHz, CDCl$_3$) δ=7.40-7.20 (m, 5H, ArH), 6.38 (d, 1H, J=8.0 Hz, NH), 5.02-4.90 (m, 1H, CH), 3.65 (s, 3H, OMe), 3.55 (s, 2H, CH$_2$), 3.18 (s, 3H, NMe), 2.25-1.70 (m, 4H, CH$_2$), 1.40 (s, 9H, $^t$Bu).
$^{13}$C NMR (50 MHz, CDCl$_3$) δ=172.1, 170.9, 166.3, 134.6, 129.3, 128.9, 127.2, 80.5, 61.6, 48.7, 43.6, 31.1, 28.0, 27.2.
MS (ESI) m/z (%): 365 [M+H, 100]$^+$.

N-(2-(Benzo[d]thiazol-2-yl)-2-oxoethyl)-2-phenylacetamide (46a)

Prepared by Procedure E

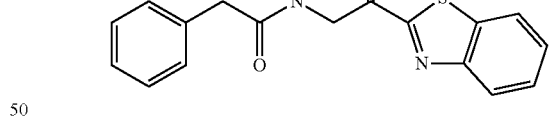

C$_{17}$H$_{14}$N$_2$O$_2$S
MW: 310.37
Orange solid.
$^1$H NMR (200 MHz, CDCl$_3$) δ=8.11 (d, 1H, J=8.0 Hz, ArH), 7.94 (d, 1H, J=8.0 Hz, ArH), 7.65-7.40 (m, 2H, ArH), 7.39-7.20 (m, 5H, ArH), 6.34 (b, 1H, NH), 4.95 (d, 2H, J=5.2 Hz, CH$_2$), 3.67 (s, 2H, CH$_2$).
$^{13}$C NMR (50 MHz, CDCl$_3$) δ=189.7, 171.4, 163.1, 153.3, 136.9, 134.4, 129.5, 129.0, 128.1, 127.4, 127.1, 125.6, 122.3, 46.8, 43.5.
MS (ESI) m/z (%): 311 [M+H, 100]$^+$.

(S)-tert-Butyl 5-(benzo[d]thiazol-2-yl)-5-oxo-4-(2-phenylacetamido)pentanoate (46b)

Prepared by Procedure E

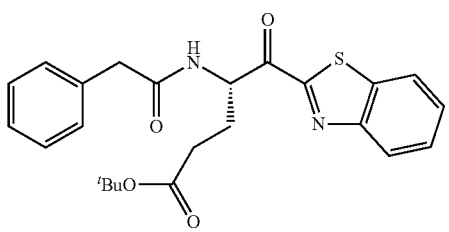 [SMILES: CC(C)(C)OC(=O)CC[C@H](NC(=O)Cc1ccccc1)C(=O)c1nc2ccccc2s1]

$C_{24}H_{26}N_2O_4S$
MW: 438.54
Colorless Oil. Yield 50%.
$^1$H NMR (200 MHz, CDCl$_3$) δ=8.10 (d, 1H, J=8.0 Hz, ArH), 7.91 (d, 1H, J=8.0 Hz, ArH), 7.62-7.20 (m, 7H, ArH), 6.77 (d, 1H, J=8.0 Hz, NH), 5.68-5.70 (m, 1H, CH), 3.61 (s, 2H, CH$_2$), 2.50-1.98 (m, 4H, CH$_2$), 1.38 (s, 9H, $^t$Bu).
$^{13}$C NMR (50 MHz, CDCl$_3$) δ=192.5, 172.1, 170.9, 163.5, 153.2, 137.0, 134.4, 129.3, 128.8, 127.9, 127.2, 127.0, 125.8, 122.2, 80.7, 55.1, 43.4, 30.3, 30.6, 27.9, 27.3.
MS (ESI) m/z (%): 439 [M+H, 55]$^+$.

(S)-5-(Benzo[d]thiazol-2-yl)-5-oxo-4-(2-phenylacetamido)pentanoic acid (47)

Prepared by Procedure X

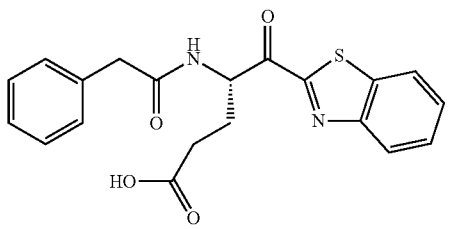 [SMILES: O=C(O)CC[C@H](NC(=O)Cc1ccccc1)C(=O)c1nc2ccccc2s1]

$C_{20}H_{18}N_2O_4S$
MW: 382.43
Yellow solid. Yield 50%.
$^1$H NMR (200 MHz, CDCl$_3$) δ=8.11 (d, 1H, J=8.0 Hz, ArH), 7.94 (d, 1H, J=8.0 Hz, ArH), 7.65-7.40 (m, 2H, ArH), 7.38-7.10 (m, 5H, ArH), 6.71 (d, 1H, T=8.0 Hz, NH), 5.90-5.60 (m, 1H, CH), 3.63 (s, 2H, CH$_2$), 2.55-2.25 (m, 3H, CH$_2$), 2.20-1.90 (m, 1H, CH$_2$).
$^{13}$C NMR (50 MHz, CDCl$_3$) δ=192.3, 177.0, 171.6, 163.3, 153.3, 137.1, 134.2, 129.4, 129.0, 128.2, 127.5, 127.2, 126.1, 125.8, 122.3, 55.2, 43.5, 30.1, 27.5.
MS (ESI) m/z (%): 381 [M−H, 100]$^-$.

Some of the compounds above were tested using an in vitro cPLA$_2$ enzyme activity assay.

In Vitro cPLA2 Assay

Assay for cPLA2 activity was performed by the use of sonicated vesicles of 1-palmitoyl-2-arachidonoyl-sn-glycerol-3-phosphorylcholine (100 μM) containing 100,000 cpm of 1-palmitoyl-2-[1 14C]arachidonoylsn-glycerol-3-phosphorylcholine in 100 mM Hepes, pH 7.5, 80 μM Ca2, 2 mM dithiothreitol, and 0.1 mg/ml BSA as described. Following a 35-mM incubation at 37° C., the reaction was terminated (derived from Wijkander et al). The lower phase was separated by thin layer chromatography, and the spot corresponding to free [1-14C]arachidonic acid was visualized by digital imaging and quantified with a PhosphorImager (Fuji Instruments). The source of cPLA$_2$ enzyme was recombinant overexpression of the human gene for group IVa PLA2 in baculovirus insect cell expression system, as described in Abdullah et al.

Wijkander, J., and Sundler, R. (1991) *Eur. J. Biochem.* 202, 873-880

Abdullah, K., et al. (1995) Human cytosolic phospholipase A2 expressed in insect cells is extensively phosphorylated on Ser-505. Biochim Biophys Acta. 1995 May 11; 1244 (1):157-64.

The results are presented below:

| Compound No. | Enzyme Assay IC 50 |
|---|---|
| 3b | 3050 nM |
| 24 | 3650 nM |
| 41 | 3700 nM |

Further Testing was Carried Out as Follows

Reagents

The Cell Culture SW982 model cell line at a confluent or spheroid state (Wada Y, 2005) was used since gene expression and generation of proinflammatory cytokines resemble RA-derived synovial fibroblast-like cells.

AA release assay: 1 h preincubation at 50 and 25 μM-4 h IL-1B stimulation, repeated 2-3 times. Only inhibitors that showed a ~50% inhibition in either of the initial two concentrations were further tested in a dose-response. IC50 is evaluated from dose-response inhibitions curves.

PGE2 Analysis

PGE$_2$ Detection

Samples and controls were slowly thawed and diluted (between 1:1 and 1:2500) in the standard diluent. The maximal dilution was 1:10 for one step. That is why several intermediate dilutions were prepared. In the beginning all values were determined from duplicates. After having minimized technical errors, samples were only analyzed as individuals. All further steps, except for some minor corrections, were performed according to the manufacturer's recommendations as can be found in the manual of the EIA kit. In order to optimize the results, the incubation time of the alkaline phosphatase substrate was prolonged by 15 minutes. During the incubation, the plates were kept in the dark. An example of the arrangements of the samples and controls is illustrated in the appendix. The read-out was carried out with a Multiscan plate reader (Ascent Labsystems) at wavelengths of 414 and 595 nm after 10 seconds shaking at 120 rpm. The corresponding software to obtain the data was the Ascent software for Multiscan, Version 2.4.1.

Data were processed using Microsoft Office Excel 2003 and SigmaPlot 10.0.

| Code | Structure | AA release SW982 cells IC50 (μM) | cPLA2 in vitro assay IC50 (μM) | PGE2-assay % inhibition |
|---|---|---|---|---|
| GK150 | 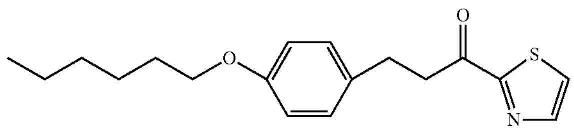 [SMILES: CCCCCCOc1ccc(CCC(=O)c2nccs2)cc1] | 5.8 | | Not yet known |
| GK152 | 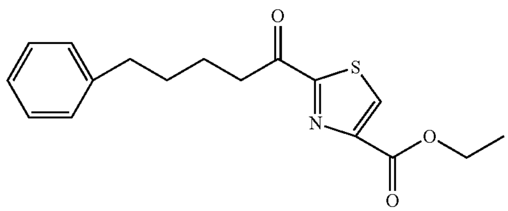 [SMILES: CCOC(=O)c1csc(C(=O)CCCCc2ccccc2)n1] | 7.4 (2 h) >25 (4 h) | >5 | 0.1 uM: 41% 3 uM:: 38% 10 uM:: 30% 30 uM: 31% |
| GK159 | 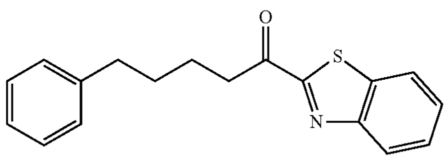 [SMILES: O=C(CCCCc1ccccc1)c1nc2ccccc2s1] | <2 (2 h) ~25 (4 h) | >5 | 0.3 uM:: 76% 3 uM: 18% 10 uM: 23% 30 uM: 10% |
| GK160 | 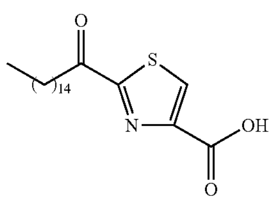 | 4.9 | 7.2 | 10 uM: 12% 30 uM: 30% |
| GK181 | 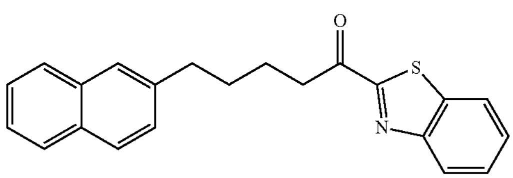 [SMILES: O=C(CCCCc1ccc2ccccc2c1)c1nc2ccccc2s1] | 1.4 | | 10 uM: 16.3% 30 uM: 22.5% |
| GK185 | 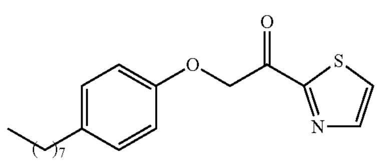 | 2.8 | 2 | Not yet known |

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:
1. A compound of formula (I')

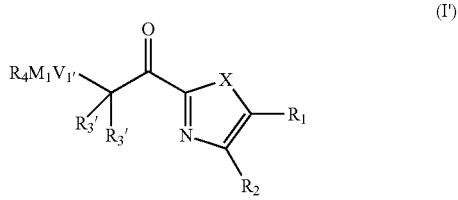

wherein X is S;
R$_1$ is H;
R$_2$ is H, OH, SH, nitro, NH$_2$, NHC$_{1-6}$alkyl, N(C$_{1-6}$alkyl)$_2$, halo, haloC$_{1-6}$alkyl, CN, C$_{1-6}$-alkyl, OC$_{1-6}$alkyl, C$_{2-6}$-alkenyl, C$_{3-10}$cycloalkyl, C$_{6-10}$aryl, C$_{1-6}$alkylC$_{6-10}$aryl, heterocyclyl, heteroaryl, CONH$_2$, CONHC$_{1-6}$alkyl, CON(C$_{1-6}$alkyl)$_2$, OCOC$_{1-6}$alkyl, —COOH, COOC$_{1-6}$alkyl, C$_{1-6}$alkylCOOH, C$_{1-6}$alkylCOOC$_{1-6}$alkyl, or is a phosphate, phosphinate, sulfate, sulfonate, or tetrazolyl group;
each R$_{3'}$ is the same or different and is H, C$_{1-6}$alkylCOOR$_a$ where R$_a$ is H or C$_{1-6}$ alkyl, halo, or CHal$_3$;
V$_{1'}$ is a C$_{1-20}$alkyl group, or C$_{2-20}$-mono or multiply unsaturated alkenyl group;
M$_1$ is a C$_{5-10}$ cycloalkyl or cycloalkenyl group or a C$_{5-15}$ aromatic group; and
R$_4$ is H, haloC$_{1-6}$alkyl, a linear C$_{1-20}$alkyl group, C$_{1-10}$ alkoxy or C$_{2-20}$-mono or multiple unsaturated alkenyl group, and
V$_{1'}$M$_1$R$_4$ provides at least 10 backbone atoms from the C(R$_{3'}$) group;
or a salt, ester, solvate, N-oxide, or prodrug thereof;
with the proviso that R$_4$M$_1$V$_{1'}$C(R$_{3'}$)$_2$ is not oleyl or —(CH$_2$)$_6$Ph.

2. A compound as claimed in claim 1, of formula (II)

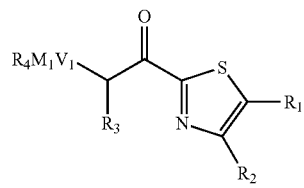

(II)

wherein R$_1$, R$_2$, R$_4$, and M$_1$ are as hereinbefore defined;
R$_3$ is H, halo, or CHal$_3$;
V$_1$ is a C$_{1-20}$alkyl group, or C$_{2-20}$-mono or multiply unsaturated alkenyl group; with the proviso that the group V$_1$M$_1$R$_4$ as a whole provides at least 10 backbone atoms from the C(R$_3$) group;
or a salt, ester, solvate, N-oxide, or prodrug thereof;
with the proviso that R$_4$M$_1$V$_1$C(R$_3$) is not oleyl or —(CH$_2$)$_6$Ph.

3. A compound as claimed in claim 1 in which R$_2$ is COOH, COOC$_{1-6}$alkyl or C$_{1-6}$alkylCOOH.

4. A compound as claimed in claim 1 in which each R$_{3'}$ is hydrogen or halo.

5. A compound as claimed in claim 1 in which V$_{1'}$ is a C$_{1-15}$-alkyl group, or C$_{2-20}$-alkenyl group.

6. A compound as claimed in claim 1 in which M$_1$ is a C$_{6-10}$aryl group.

7. A compound as claimed in claim 1 in which R$_4$ is an H atom or a C$_{1-10}$alkyl group.

8. A pharmaceutical composition comprising a compound of claim 1 and a pharmaceutically acceptable carrier.

9. A method of treating a chronic inflammatory disorder comprising administering to a patient in need thereof an effective amount of a compound of claim 1;
or a salt, ester, solvate, N-oxide, or prodrug thereof;
such that the chronic inflammatory condition is treated, and wherein the compound or salt, ester, solvate, N-oxide or prodrug thereof is a cPLA$_2$ inhibitor.

10. A method as claimed in claim 9, the method comprising administration of a compound of claim 2;
or a salt, ester, solvate, N-oxide, or prodrug thereof.

11. A method as claimed in claim 9 wherein said chronic inflammatory disorder is glomerulonephritis, rheumatoid arthritis or psoriasis.

12. A method of treating atopic dermatitis, allergic contact dermatitis, seborrheic dermatitis, pityriasis rosea, lichen planus or drug eruptions, the method comprising administering to a patient in need thereof an effective amount of a compound of claim 1, wherein the compound is a cPLA$_2$ inhibitor.

13. A method of treating arthritis, dermatoses, inflammatory CNS diseases, multiple sclerosis, chronic obstructive pulmonary disease, chronic lung inflammatory conditions, inflammatory bowel disease or cardiovascular disease, the method comprising administering to a patient in need thereof an effective amount of a compound of claim 1, wherein the compound is a cPLA$_2$ inhibitor.

14. A compound

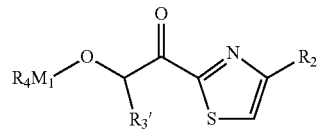

M is phenyl;
R$_2$ is COOH, COOC$_{1-6}$alkyl and C$_{1-6}$alkylCOOH;
R$_{3'}$ is C$_{1-6}$ alkyl;
R$_4$ is H, haloC$_{1-6}$alkyl, a linear C$_{1-20}$ alkyl group, C$_{1-10}$ alkoxy, —SC$_{1-20}$ alkyl group or C$_{2-20}$ mono or multiple unsaturated alkenyl group;
or a salt, ester, solvate or prodrug thereof.

15. A compound of the structure:

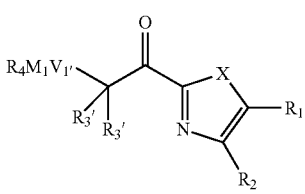

wherein M$_1$ is phenyl;
R$_2$ is COOC$_{1-6}$alkyl or C$_{1-6}$alkylCOOC$_{1-6}$alkyl;
R$_{3'}$ is H;
R$_4$ is H, a linear C$_{1-20}$ alkyl group, C$_{1-10}$ alkoxy, or —SC$_{1-20}$ alkyl group or C$_{2-20}$ mono or multiple unsaturated alkenyl group;
or a salt, ester, solvate or prodrug thereof.

16. The compound of claim 14 wherein R$_4$ is a linear C$_{1-20}$ alkyl group or C$_{1-10}$ alkoxy.

17. A compound of formula (I')

(I')

wherein X is S;
R$_1$ is H;
R$_2$ is COOH, COOC$_{1-6}$alkyl or C$_{1-6}$alkylCOOH;

each $R_{3'}$ is the same or different and is H, $C_{1-6}$alkyl-COOR$_a$ where $R_a$ is H or $C_{1-6}$ alkyl, halo, or CHal$_3$;

$V_{1'}$ is a $C_{1-20}$alkyl group, or $C_{2-20}$-mono or multiply unsaturated alkenyl group;

$M_1$ is a $C_{5-10}$ cycloalkyl or cycloalkenyl group or a $C_{5-15}$ aromatic group; and $R_4$ is H, halo$C_{1-6}$alkyl, a linear $C_{1-20}$alkyl group, $C_{1-10}$ alkoxy or $C_{2-20}$-mono or multiple unsaturated alkenyl group, and or a salt, ester, solvate, N-oxide, or prodrug thereof;

with the proviso that $R_4M_1V_{1'}C(R_{3'})_2$ is not oleyl or —(CH$_2$)$_6$Ph.

18. A compound as claimed in claim 1, wherein the compound is selected from the group consisting of:

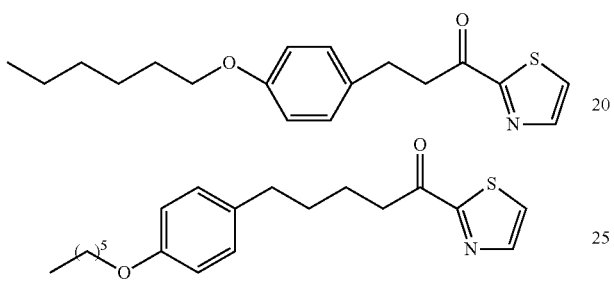

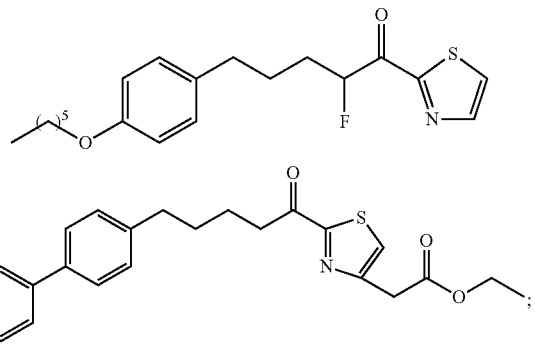

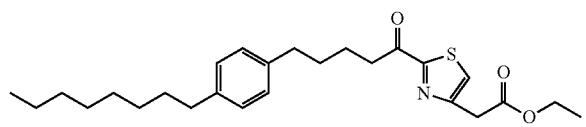

and or a salt, ester, solvate, N-oxide, or prodrug thereof.

* * * * *